US006462176B1

(12) United States Patent
Ashkenazi

(10) Patent No.: US 6,462,176 B1
(45) Date of Patent: Oct. 8, 2002

(54) APO-3 POLYPEPTIDE

(75) Inventor: Avi J. Ashkenazi, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 08/928,069

(22) Filed: Sep. 11, 1997

Related U.S. Application Data

(60) Provisional application No. 60/026,943, filed on Sep. 23, 1996.

(51) Int. Cl.[7] ......................... C07K 14/47; C07K 17/14
(52) U.S. Cl. ..................... 530/350; 530/300; 530/387.1
(58) Field of Search ............................... 530/350, 300, 530/387.1

(56) References Cited

U.S. PATENT DOCUMENTS

| | | | |
|---|---|---|---|
| 3,691,016 A | 9/1972 | Petal | 435/181 |
| 3,969,287 A | 7/1976 | Jaworek et al. | 526/238.1 |
| 4,179,337 A | 12/1979 | Davis et al. | 435/181 |
| 4,195,128 A | 3/1980 | Hildebrand et al. | 435/178 |
| 4,229,537 A | 10/1980 | Hodgins et al. | 435/177 |
| 4,247,642 A | 1/1981 | Hirohara et al. | 435/178 |
| 4,301,144 A | 11/1981 | Iwashita et al. | 514/6 |
| 4,330,440 A | 5/1982 | Ayers et al. | 525/54.31 |
| 4,342,566 A | 8/1982 | Theofilopoulos et al. | 436/507 |
| 4,399,216 A | 8/1983 | Axel et al. | 435/6 |
| 4,419,446 A | 12/1983 | Howley et al. | 435/69.1 |
| 4,496,689 A | 1/1985 | Mitra | 525/54.1 |
| 4,601,978 A | 7/1986 | Karin | 435/69.1 |
| 4,640,835 A | 2/1987 | Shimizu et al. | 424/94.63 |
| 4,670,417 A | 6/1987 | Iwasaki et al. | 514/6 |
| 4,676,980 A | 6/1987 | Segal et al. | 424/136.1 |
| 4,736,866 A | 4/1988 | Leder et al. | 800/10 |
| 4,791,192 A | 12/1988 | Nakagawa et al. | 530/399 |
| 4,816,567 A | 3/1989 | Cabilly et al. | 530/387.3 |
| 4,870,009 A | 9/1989 | Evans et al. | 435/69.4 |
| 4,965,199 A | 10/1990 | Capon et al. | 435/69.6 |
| 5,010,182 A | 4/1991 | Brake et al. | 536/23.7 |
| 5,364,934 A | 11/1994 | Drayna et al. | 536/23.2 |
| 6,153,402 A | 11/2000 | Yu et al. | 435/69.1 |

FOREIGN PATENT DOCUMENTS

| | | |
|---|---|---|
| DE | 266710 | 4/1989 |
| EP | 003089 | 7/1979 |
| EP | 036776 | 9/1981 |
| EP | 073657 | 3/1983 |
| EP | 117058 | 8/1984 |
| EP | 117060 | 8/1984 |
| EP | 125023 A1 | 11/1984 |
| EP | 173494 | 3/1986 |
| EP | 278776 | 8/1988 |
| EP | 307247 | 3/1989 |
| EP | 321196 | 6/1989 |
| EP | 362179 | 4/1990 |
| EP | 417563 | 3/1991 |
| EP | 911633.00 | 4/1999 |
| GB | 2211504 | 7/1989 |
| WO | WO 87/05330 | 9/1987 |
| WO | WO 89/02922 | 4/1989 |
| WO | WO 89/05859 | 6/1989 |
| WO | WO 90/13646 | 11/1990 |
| WO | WO 91/00358 | 1/1991 |
| WO | WO 91/00360 | 1/1991 |
| WO | WO 91/08291 | 6/1991 |
| WO | WO 92/20373 | 11/1992 |
| WO | WO 93/08829 | 5/1993 |
| WO | WO 94/04679 | 3/1994 |
| WO | WO 94/04690 | 3/1994 |
| WO | WO 94/29348 | 12/1994 |
| WO | WO 95/10540 | 4/1995 |
| WO | WO 95/11301 | 4/1995 |
| WO | WO 95/31544 | 11/1995 |
| WO | WO 97/33904 | 9/1997 |
| WO | 97/37020 | 10/1997 |
| WO | 98/14565 | 4/1998 |
| WO | 00/64465 | 11/2000 |

OTHER PUBLICATIONS

Harlow et al. Antibodies: a laboratory manual. Cold Spring Harbor:Cold Spring Harbor Laboratory Press. p. 76, 1988.*

The Merck Index, eighth edition. Stecher et al. (eds.) NJ: Merck & Co, Inc. p. 497, 1968.*

Grenet et al., "Duplication of the DR3 Gene on Human Chromosome 1p36 and Its Deletion in Human Neuroblastoma," *Genomics*, 49, 385–393 (1998).

Tan et al., "Characterization of a novel TNF–like ligand and recently described TNF ligand and TNF receptor superfamily genes and their constitutive and inducible expression in hematopoietic and non–hematopoietic cells," *Gene*, 204, 35–46 (1997).

Warzocha et al., "A New Death Receptor 3 Isoform: Expression in Human Lymphoid Cell Lines and Non–Hodgkin's Lymphomas," *Biochemical and Biophysical Research Communications*, 242, 376–379 (1998).

Hillier et al., Genbank Sequence Accession No. H–41522, Publicly avail. Jul. 31, 1995.

Bodmer et al., "TRAMP, a Novel Apoptosis–Mediating Receptor with Sequence Homology to Tumor Necrosis Factor Receptor 1 and Fas(Apo–1/CD95)," *Immunity*, 6:79–88 (1997).

Brojatsch et al., "CAR1, a TNFR–Related Protein, Is a Cellular Receptor for Cytopathic Avian Leukosis–Sarcoma Virsuses and Mediates Apoptosis," *Cell*, 87:845–855 (1996).

Degli–Esposti et al., "Cloning and Characterization of TRAIL–R3, a Novel Member of the Emerging TRAIL Receptor Family," *j. Exp. Med.*, 186:1165–1170 (1997).

(List continued on next page.)

*Primary Examiner*—Gabrielle Bugaisky
(74) *Attorney, Agent, or Firm*—Diane L. Marschang

(57) ABSTRACT

Novel polypeptides, designated Apo-3, which are capable of stimulating or inducing apoptosis are provided. Compositions including Apo-3 chimeras, nucleic acid encoding Apo-3, and antibodies to Apo-3 are also provided.

9 Claims, 16 Drawing Sheets

OTHER PUBLICATIONS

MacFarlane et al., "Identification and Molecular Cloning of Two Novel Receptors for the Cytotoxic Ligand TRAIL," *J. Biol. Chem.*, 272:25417–25420 (1997).

Marsters et al., "Apo–3, a new member of the tumor necrosis factor receptor family, contains a death domain and activates apoptosis and NF–κB," *Current Biology*, 1669–1676 (1996).

Montgomery et al., "Herpes Simplex Virus–1 Entry into Cells Mediated by a Novel Member of the TNF/NGF Receptor Family," *Cell*, 87:427–436 (1996).

Screaton et al., "LARD: A new lymphoid–specific death domain containing receptor regulated by alternative pre–mRNA splicing," *Proc. Natl. Acad. Sci.*, 94:4615–4619 (1997).

Simonet et al., "Osteoprotegerin: A Novel Secreted Protein Involved in the Regulation of Bone Density," *Cell*, 89:309–319 (1997).

von Bölow et al., "NF–AT Activation Induced by a CAML–Interacting Member of the Tumor Necrosis Factor Receptor Superfamily," *Science*, 278:138–141 (1997).

Wong et al., "TRANCE Is a Novel Ligand of the Tumor Necrosis Factor Receptor Family That Activates c–Jun N–terminal Kinase in T Cells," *J. Biol. Chem.*, 272:25190–25194 (1997).

Walczak et al., "TRAIL–R2: a novel apoptosis–mediating receptor for TRAIL," *EMBO J.*, 16:5386–5397 (1997).

Adams et al., "Molecular cloning of mouse immunoglobulin heavy chain messenger ribonucleic acids coding for $\mu$, $\alpha$, $\gamma 1$, $\gamma 2a$, and $\gamma 3$ chains" *Biochemistry* 19:2711–2719 (1980).

Amakawa et al., "The Hodgkin Disease Antigen CD30 is Crucial for Antigen–induced Death of Developing T Cells" *Cold Spring Harbor Laboratory Symposium on Programmed Cell Death* (Abstr. No. 10) (1995).

Aplin et al., "Preparation, Properties, and Applications of Carbohydrate Conjugates of Proteins and Lipids" *CRC Crit. Rev. Biochem.* 10(4):259–306 (1981).

Ashkenazi and Chamow, "Immunoadhesins: An Alternative to Human Monoclonal Antibodies" *Methods: A Companion to Methods in Enzymology* 8:104–115 (1995).

Ashkenazi et al., "Protection Against Endotoxic Shock by a Tumor Necrosis Factor Receptor Immunoadhesin" *Proc. Natl. Acad. Sci.* 88:10535–10539 (1991).

Banerji et al., "A Lymphocyte–specific Cellular Enhancer Is Located Downstream of the Joining Region in Immunoglobulin Heavy Chain Genes" *Cell* 33:729–740 (Jul. 1983).

Banner, "Crystal Structure of the Soluble Human 55 kd TNF Receptor–Human TNFβ Complex: Implications for TNF Receptor Activation" *Cell* 73:431–445 (1993).

Barr et al., "Apoptosis and Its Role in Human Disease" *Bio/Technology* 12:487–493 (1994).

Bianchi et al., "Transformation of the yeast Kluyveromyces lactis by New Vectors Derived from the 1.6 $\mu$m Circular Plasmid pKD1" *Curr. Genet.* 12:185–192 (1987).

Boerner et al., "Production of Antigen–Specific Human Monoclonal Antibodies From In Vitro–Primed Human Splenocytes" *The Journal of Immunology* 147(1):86–95 (1991).

Boldin et al., "Involvement of MACH, a Novel MORT1/FADD–Interacting Protease, in Fas/APO–1– and TNF Receptor–Induced Cell Death" *Cell* 85:803–815 (1996).

Boldin et al., "Self–Association of the "Death Domains" of the p55 Tumor Necrosis Factor (TNF) Receptor and Fas/APO1 Prompts Signaling for TNF and Fas/APO1 Effects" *Journal of Biological Chemistry* 270:387–391 (1995).

Boulianne et al., "Production of functional chimaeric mouse/human antibody" *Nature* 312:643–646 (Dec. 13, 1984).

Bradley,, "Production and Analysis of Chimaeric Mice" *Teratocarcinomas and Embryonic Stem Cells: A Practical Approach*, E. J. Robertson, ed., IRL, Oxford, Chapter 5, pp. 113–151 (1987).

Brockhaus et al., "Identification of two types of tumor necrosis factor receptors on human cell lines by monoclonal antibodies" *Proc. Natl. Acad. Sci. USA* 8:3127–3131 (1990).

Brodeur et al., "Mouse–Human Myeloma Partners for the Production of Heterohybridomas" *Monoclonal Antibody Production Techniques and Applications*, New York:Marcel Dekker, Inc. pp. 51–63 (1987).

Browning et al., "Lymphotoxin β, a Novel Member of the TNF Family That Forms a Heteromeric Complex with Lymphotoxin on the Cell Surface" *Cell* 72:847–856 (1993).

Bruggemann et al., "Designer Mice: The Production of Human Antibody Repertoires in Transgenic Animals" *Year in Immunology* 7:33–40 (1993).

Byrn et al., "Biological Properties of a CD4 Immunoadhesin" *Nature* 344:667–670 (Apr. 12, 1990).

Canaani et al., "Regulated Expression of Human Interferon $\beta_1$ Gene After Transduction into Cultured Mouse and Rabbit Cells" *Proc. Natl. Acad. Sci. USA* 79:5166–5170 (Sep. 1982).

Capon et al., "Designing CD4 Immunoadhesins for AIDS Therapy" *Nature* 337:525–531 (Feb. 9, 1989).

Carter et al., "Humanization of an anti–p185$^{HER2}$ antibody for human cancer therapy" *Proc. Natl. Acad. Sci.* 89:4285–4289 (1992).

Chamow et al., "A Humanized, Bispecific Immunoadhesin–Antibody That Retargets CD3$^+$ Effectors to Kill HIV–1–Infected Cells" *Journal of Immunology* 153:4268–4280 (1994).

Chang et al., "Phenotypic Expression in *E. coli* of a DNA Sequence Coding for Mouse Dihydrofolate Reductase" *Nature* 275:617–624 (Oct. 19, 1978).

Chinnaiyan and Dixit, "The Cell–Death Machine" *Current Biology* 6:555–562 (1996).

Chinnaiyan et al., "FADD, a novel death domain–containing protein, interacts with the death domain of Fas and initiates apoptosis" *Cell* 81:505–512 (1995).

Chinnaiyan et al., "FADD/MORT1 Is a Common Mediator of CD95 (Fas/APO–1) and Tumor Necrosis Factor Receptor–induced Apoptosis" *Journal of Biological Chemistry* 271:4961–4965 (1996).

Chinnaiyan et al., "Signal Transduction by DR3, a Death Domain–Containing Receptor Related to TNFR–1 and CD95" *Science* 274:990–992 (1996).

Chothia and Lesk, "Canonical structures for the hypervariable regions of immunoglobulins" *J. Mol. Biol.* 196(4):901–917 (1987).

Cleveland and Ihle, "Contenders in FasL/TNF Death Signaling" *Cell* 81:479–482 (1995).

Cohen, "Programmed Cell Death in the Immune System" *Advances in Immunol.* 50:55–85 (1991).

Cole et al., "The EBV–Hybridoma Technique and Its Application to Human Lung Cancer" *Monoclonal Antibodies and Cancer Therapy*, Reisfeld et al., New York:Alan R. Liss, Inc. pp. 77–96 (1985).

Creighton,, "Protein Biosynthesis" *Proteins: Structures and Molecular Principles*, San Francisco:W.H. Freeman & Co. pp. 79–86 (1983).

Darzynkiewicz et al., "Assays of Cell Viability: Discrimination of Cells Dying by Apoptosis" *Methods in Cell Biol.* 41:15–38 (1994).

David et al., "Protein Iodination with Solid State Lactoperoxidase" *Biochemistry* 13(5):1014–1021 (1974).

Dealtry et al., "DNA Fragmentation and Cytotoxicity Caused by Tumor Necrosis Factor is Enhanced by Interferon–γ" *European Journal of Immunology* 17:689–693 (1987).

deBoer et al., "The TAC Promoter: A functional Hybrid Derived From the TRP and LAC Promoters" *Proc. Natl. Acad. Sci. USA* 80:21–25 (1983).

Depicker et al., "Nopaline Synthase: Transcript Mapping and DNA Sequence" *J. Mol. Appl. Gen.* 1:561–573 (1982).

Dieffenbach et al., *PCR Primer: A Laboratory Manual*, Cold Spring Harbor Laboratory Press pp. 1–16;133–142 (1995).

Dolby et al., "Cloning and partial nucleotide sequence of human immunoglobulin μ chain cDNA from B cells and mouse–human hybridomas" *Proc. Natl. Acad. Sci. USA* 77(10):6027–6031 (1980).

Duksin et al., "Relationship of the Structure and Biological Activity of the Natural Homologues of Tunicamycin" *Journal of Biological Chemistry* 257:3105–3109 (1982).

Eck and Sprang, "The structure of tumor necrosis factor–α at 2.6 A resolution" *Journal of Biological Chemistry* 264(29):17595–17604 (1989).

Eck et al., "The Structure of Human Lymphotoxin (Tumor Necrosis Factor–β) at 1.9–A Resolution" *J. Bio. Chem.* 267:2119–2122 (1992).

Edge et al., "Deglycosylation of glycoproteins by trifluoromethanesulfonic acid" *Analytical Biochemistry* 118:131–137 (1981).

Enari et al., "Involvement of an ICE–like protease in Fas–mediated Apoptosis" *Nature* 375:78–81 (1995).

Evan et al., "Isolation of Monoclonal Antibodies Specific for Human c–myc Proto–Oncogene Product" *Molecular & Cellular Biology* 5:3610–3616 (1985).

Fadok et al., "Exposure of Phosphatidylserine on the Surface of Apoptotic Lymphocytes Triggers Specific Recognition and Removal by Macrophages" *J. Immunol.* 148:2207–2216 (1992).

Falkner and Zachau, "Expression of mouse immunoglobulin genes in monkey cells" *Nature* 298:286–288 (1982).

Field et al., "Purification of a RAS–Responsive Adenylyl Cyclase Complex from *Saccharomyces cerevisiae* by Use of an Epitope Addition Method" *Molecular & Cellular Biology* 8:2159–2165 (1988).

Fiers et al., "Complete Nucleotide Sequence of SV40 DNA" *Nature* 273:113(May 11, 1978).

Fleer et al., "Stable Multicopy Vectors for High–Level Secretion of Recombinant Human Serum Albumin by Kluyveromyces Yeasts" *Bio/Technology* 9:968–975 (1991).

Fraser and Evan, "A License to Kill" *Cell* 85:781–784 (1996).

Gething et al., "Cell–surface Expression of Influenza Haemagglutinin from a Cloned DNA Copy of the RNA Gene" *Nature* 293:620–625 (Oct. 22, 1981).

Goding, "Production of Monoclonal Antibodies" *Monoclonal Antibodies: Principles and Practice*, Academic Press, pp. 59–103 (1986).

Goeddel et al., "Direct Expression in *Escherichia coli* of a DNA Sequence Coding for Human Growth Hormone" *Nature* 281:544–548 (Oct. 18, 1979).

Goeddel et al., "Synthesis of Human Fibroblast Interferon by *E. coli* " *Nucleic Acids Research* 8(18):4057–4074 (1980).

Goodwin et al., "Molecular cloning and expression of the type 1 and type 2 murine receptors for tumor necrosis factor" *Molecular & Cellular Biology* 11:3020–3026 (1991).

Gorman et al., "The Rous Sarcoma Virus Long Terminal Repeat is a Strong Promoter When Introduced into a Variety of Eukaryotic Cells by DNA–Mediated Transfection" *Proc. Natl. Acad. Sci. USA* 79:6777–6781 (Nov. 1982).

Gough et al., "Molecular cloning of seven mouse immunoglobulin κ chain messenger ribonucleic acids" *Biochemistry* 19:2702–2710 (1980).

Graham et al., "Characteristics of a Human Cell Line Transformed by DNA from Human Adenovirus Type 5" *J. Gen. Virol.* 36:59–72 (1977).

Graham et al., "A New Technique for the Assay of Infectivity of Human Adenovirus 5 DNA" *Virology* 52:456–467 (1973).

Gray et al., "Expression of Human Immune Interferon cDNA in *E. coli* and Monkey Cells" *Nature* 295:503–508 (Feb. 11, 1982).

Greenaway et al., "Human Cytomegalovirus DNA: BamHI, EcoRI and PstI Restriction Endonuclease Cleavage Maps" *Gene* 18:355–360 (1982).

Gruss and Dower, "Tumor Necrosis Factor Ligand Superfamily: Involvement in the Pathology of Malignant Lymphomas" *Blood* 85:3378–3404 (1995).

Hale et al., "Demonstration of in vitro and in vivo efficacy of two biologically active human soluble TNF receptors expressed in *E. coli* " *J. Cell. Biochem.* (abstract only Supplement 15F; P 424) pp. 113 (1991).

Hess et al., "Cooperation of Glycolytic Enzymes" *Advances in Enzyme Regulation*, George Weber, New York:Pergamon Press vol. 7:149–167 (1968).

Hitzeman et al., "Isolation and Characterization of the Yeast 3–Phosphoglycerokinase Gene (PGK) by an Immunological Screening Technique" *Journal of Biological Chemistry* 255(24):12073–12080 (Dec. 25, 1980).

Hohmann et al., "Two different cell types have different major receptors for human tumor necrosis factor (TNF alpha)" *Journal of Biological Chemistry* 264(25):14927–14934 (1989).

Holland et al., "Isolation and Identification of Yeast Messenger Ribonucleic Acids Coding for Enolase, Glyceraldehyde–3–phosphate Dehydrogenase, and Phosphoglycerate Kinase" *Biochemistry* 17(23):4900–4907 (1978).

Hoogenboom and Winter, "By–passing immunisation: human antibodies from synthetic repertoires of germline $V_H$ gene segments rearranged in vitro" *J. Mol. Biol.* 227:381–388 (1992).

Hopp et al., "A Short Polypeptide Marker Sequence Useful for Recombinant Protein Identification and Purification" *Bio/Technology* 6:1204–1210 (1988).

Hsiao et al., "High–frequency Transformation of Yeast by Plasmids Containing the Cloned Yeast Arg4 Gene" *Proc. Natl. Acad. Sci. USA* 76:3829–3833 (1979).

Hsu et al., "TRADD–TRAF2 and TRADD–FADD interactions define two distinct TNF receptor 1 signal transduction pathways" *Cell* 84:299–308 (1996).

Hunter et al., "Preparation of Iodine 131 Labelled Human Growth Hormone of High Specific Activity" *Nature* 194:495–496 (1962).

Itoh et al., "The polypeptide encoded by the cDNA for human cell surface antigen Fas can mediate apoptosis" *Cell* 66:233–243 (1991).

Jakobovits et al., "Analysis of Homozygous Mutant Chimeric Mice: Deletion of the Immunoglobulin Heavy–Chain Joining Region Blocks B–cell Development and Antibody Production" *Proc. Natl. Acad. Sci. USA* 90:2551–2555 (Mar. 1993).

Jakobovits et al., "Germ–line Transmission and Expression of a Human–Derived Yeast Artificial Chromosome" *Nature* 362:255–258 (Mar. 18, 1993).

Johnson et al., "Expression and Structure of the Human NGF Receptor" *Cell* 47:545–554 (Nov. 21, 1986).

Jones et al., "Replacing the Complementarity–determining Regions in a Human Antibody with Those From a Mouse" *Nature* 321:522–525 (May 29, 1986).

Jones, E., "Proteinase Mutants of *Saccharomyces Cerevisiae*" *Genetics* 85(1):23–33 (1977).

Keown et al., "Methods for Introducing DNA into Mammalian Cells" *Methods in Enzymology* 185:527–537 (1990).

Kingsman et al., "Replication in *Saccharomyces Cerevisiae* of Plasmid pBR313 Carrying DNA from the Yeast trp1 Region" *Gene* 7;141–152 (1979).

Kitson et al., "A Death–Domain–Containing Receptor that Mediates Apoptosis" *Nature* 384:372–375 (1996).

Kohler et al., "Continuous Cultures of Fused Cells Secreting Antibody of Predefined Specificity" *Nature* 256:495–497 (Aug. 7, 1975).

Kohno et al., "A second tumor necrosis factor receptor gene product can shed a naturally occurring tumor necrosis factor inhibitor" *Proc. Natl. Acad. Sci. USA* 87:8331–8335 (1990).

Koopman et al., "Annexin V for Flow Cytometric Detection of Phosphatidylserine Expression on B Cells Undergoing Apoptosis" *Blood* 84:1415–1420 (1994).

Kozak, "An analysis of vertebrate mRNA sequences: intimations of translational control" *Journal of Cell Biology* 115:887–903 (1991).

Kozbor et al., "A Human Hybrid Myeloma for Production of Human Monoclonal Antibodies" *The Journal of Immunology* 133(6):3001–3005 (1984).

Krammer et al., "Regulation of Apoptosis in the Immune System" *Curr. Op. Immunol.* 6:279–289 (1994).

Laimins et al., "Osmotic Control of kdp Operon Expression in *Escherichia Coli* " *Proc. Natl. Acad. Sci. USA* 78(1):464–468 (Jan. 1981).

Lasky et al., "DNA sequence analysis of the type–common glycoprotein–D genes of herpes simplex virus types 1 and 2" *DNA* 3(1):23–29 (1984).

Lasky et al., "Neutralization of the AIDS Retrovirus by Antibodies to a Recombinant Envelope Glycoprotein" *Science* 233:209–212 (1986).

Lenardo, "Interleukin-2 Programs Mouse $\alpha\beta$ T Lymphocytes for Apoptosis" *Nature* 353:858–861 (1991).

Lesslauer et al., "Bioactivity of recombinant human TNF receptor fragments" *J. Cell. Biochem.* (abstract only, Supplement 15F; P432) p. 115 (1991).

Lewis et al., "Cloning and expression of cDNAs for two distinct murine tumor necrosis factor receptors demonstrate one receptor is species specific" *Proc. Natl. Acad. Sci. USA* 88:2830–2834 (1991).

Li et al., "Targeted mutation of the DNA methyltransferase gene results in embryonic lethality" *Cell* 69:915–926 (1992).

Loetscher et al., "Molecular Cloning and Expression of the Human 55 kd Tumor Necrosis Factor Receptor" *Cell* 61:351–359 (Apr. 20, 1990).

Luckow et al., "Trends in the Development of Baculovirus Expression Vectors" *Bio/Technology* 6:47–55 (1988).

Lusky et al., "Bovine Papilloma Virus Contains an Activator of Gene Expression at the Distal End of the Early Transcription Unit" *Molecular & Cellular Biology* 3(6):1108–1122 (Jun. 1983).

Lutz–Freyermuth et al., "Quantitative Determination That One of Two Potential RNA–binding Domains of the A Protein Component of the U1 Small Nuclear Ribonucleoprotein Complex Binds with High Affinity to Stem–loop II of U1 RNA" *Proc. Natl. Acad. Sci. USA* 87:6393–6397 (1990).

MacKay et al., "Differential Responses of Fibroblasts from Wild–Type and TNF–R55–Deficient Mice to Mouse and Human TNF–Alpha Activation" *J. Immunol.* 153:5274–5284 (1994).

Maeda et al., "Production of Human $\alpha$–interferon in Silkworm Using a Baculovirus Vector" *Nature* 315:592–594 (Jun. 13, 1985).

Mage et al., "Preparation of Fab and F(ab')$_2$ Fragments from Monoclonal Antibodies" *Monoclonal Antibody Production Techniques and Applications*, New York:Marcel Dekker, Inc. pp. 79–97 (1987).

Mallett et al., "Characterization of the MRC OX40 Antigen of Activated CD4 Positive T Lymphocytes—a Molecule Related to Nerve Growth Factor Receptor" *EMBO Journal* 9:1063–1068 (1990).

Mansour et al., "Disruption of the Proto–oncogene int–2 in Mouse Embryo–derived Stem Cells: a General Strategy for Targeting Mutations to Non–selectable Genes" *Nature* 336:348–352 (1988).

Mantei et al., "Rabbit $\beta$–globin mRNA Production in Mouse L Cells Transformed with Cloned Rabbit $\beta$–globin Chromosomal DNA" *Nature* 281:40–46 (Sep. 6, 1979).

Marks et al., "By–passing immunization: human antibodies from V–gene libraries displayed on phage" *J. Mol. Biol.* 222:581–597 (1991).

Marsters et al., "Interferon Gamma Signals Via a High–Affinity Multisubunit Receptor Complex That Contains Two Types of Polypeptide Chain" *Proc. Natl. Acad. Sci. USA* 92:5401–5405 (1995).

Martin et al., "Cell–free Reconstitution of Fas–, UV Radiation– and Ceramide–induced Apoptosis" *EMBO Journal* 14(21):5191–5200 (1995).

Martin et al., "GAP Domains Responsible for Ras p21–Dependent Inhibition of Muscarinic Atrial K$^+$ Channel Currents" *Science* 255:192–194 (1992).

Mather et al., "Culture of Testicular Cells in Hormone–Supplemented Serum–Free Medium" *Annals N.Y. Acad. Sci.* 383:44–68 (1982).

Mather et al., "Establishment and Characterization of Two Distinct Mouse Testicular Epithelial Cell Lines" *Biol. Reprod.* 23:243–252 (1980).

Maxam et al., "Sequencing End–labeled DNA with Base–Specific Chemical Cleavages" *Methods in Enzymology* 65:499–560 (1980).

McCafferty et al., "Phage antibodies: filamentous phage displaying antibody variable domains" *Nature* 348:552–554 (1990).

Messing et al., "A System for Shotgun DNA Sequencing" *Nucleic Acids Research* 9(2):309–321 (1981).

Miller et al., "An Insect Baculovirus Host–Vector System for High–Level Expression of Foreign Genes" *Genetic Engineering*, Setlow et al., Plenum Publishing vol. 8:277–298 (1986).

Milstein et al., "Hybrid Hybridomas and Their Use in Immunohistochemistry" *Nature* 305:537–540 (1983).

Moore et al., "Apoptosis in CHO Cell Batch Cultures: Examination by Flow Cytometry" *Cytotechnology* 17:1–11 (1995).

Mordenti et al., "Interspecies Scaling of Clearance and Volume of Distribution Data for Five Therapeutic Proteins" *Pharmaceutical Research* 8(11):1351–1359 (1991).

Morrison et al., "Chimeric Human Antibody Molecules: Mouse Antigen–binding Domains with Human Constant Region Domains" *Proc. Natl. Acad. Sci. USA* 81:6851–6855 (Nov. 1984).

Morrison et al., "Transfer and expression of immunoglobulin genes" *Annual Review of Immunology* 2:239–256 (1984).

Morrison, S. L., "Transfectomas Provide Novel Chimeric Antibodies" *Science* 229:1202–1207 (Sep. 20, 1985).

Mulligan et al., "Expression of a Bacterial Gene in Mammalian Cells" *Science* 209:1422–1427 (Sep. 1980).

Munro, "Uses of chimaeric antibodies" *Nature* 312:597 (1984).

Munson et al., "LIGAND: A Versatile Computerized Approach for Characterization of Ligand–Binding Systems" *Analytical Biochemistry* 107:220–239 (1980).

Muzio et al., "FLICE, A Novel FADD–Homologous ICE/CED–3–like Protease, Is Recruited to the CD95 (Fas/APO–1) Death–Inducing Signaling Complex" *Cell* 85:817–827 (1996).

Nagata et al., "The Fas Death Factor" *Science* 267:1449–1456 (1995).

Neuberger et al., "Recombinant Antibodies Possessing Novel Effector Functions" *Nature* 312:604–608 (Dec. 13, 1984).

Nophar et al., "Soluble forms of tumor necrosis factor receptors (TNF–Rs). The cDNA for the type I TNF–R, cloned using amino acid sequence data of its soluble form, encodes both the cell surface and a soluble form of the receptor" *EMBO Journal* 9:3269–3278 (1990).

Nygren, H., "Conjugation of Horseradish Peroxidase to Fab Fragments with Different Homobifunctional and Heterobifunctional Cross–Linking Reagents" *The Journal of Histochemistry and Cytochemistry* 30(5):407–412 (1982).

O'Reilley et al. *Baculovirus Expression Vectors: A Laboratory Manual*, Oxford:Oxford University Press (1994).

Osborne et al., "Transcription Control Region Within the Protein–coding Portion of Adenovirus E1A Genes" *Molecular & Cellular Biology* 4(7):1293–1305 (Jul. 1984).

Paborsky et al., "Mammalian Cell Transient Expression of Tissue Factor for the Production of Antigen" *Protein Eng.* 3(6):547–553 (1990).

Pain et al., "Preparation of Protein A–Peroxidase Monoconjugate Using a Heterobifunctional Reagent, and its Use in Enzyme Immunoassays" *Journal of Immunological Methods* 40:219–230 (1981).

Pavlakis et al., "Expression of Two Human Growth Hormone Genes in Monkey Cells Infected by Simian Virus 40 Recombinants" *Proc. Natl. Acad. Sci. USA* 78(12):7398–7402 (Dec. 1981).

Peetre et al., "A tumor necrosis factor binding protein is present in human biological fluids" *Eur. J. Haemotol.* 41:414–419 (1988).

Pennica et al., "Expression Cloning of Cardiotrophin 1, a Cytokine That Induces Cardiac Myocyte Hypertrophy" *Proceedings of the National Academy of Sciences, USA* 92:1142–1146 (Feb. 1995).

Pennica et al., "Human Tumour Necrosis Factor: Precursor Structure, Expression and Homology to Lymphotoxin" *Nature* 312:724–729 (1984).

Peppel and Beutler, "Chimaeric TNF–Receptor–IgG Molecule Acts as Soluble Inhibitor of TNF Mediated Cytotoxicity" *J. Cell. Biochem.* (abstract only, Supplement 15F; P439) p. 118 (1991).

Pitti et al., "Induction of Apoptosis by Apo–2 Ligand, a New Member of the Tumor Necrosis Factor Cytokine Family" *Journal of Biological Chemistry* 271:12687–12690 (1996).

Presta et al., "Humanization of an Antibody Directed Against IgE" *J. Immunol.* 151(5):2623–2632 (Sep. 1, 1993).

Presta, L., "Antibody Engineering" *Curr. Op. Struct. Biol.* 2:593–596 (1992).

Radeke et al., "Gene transfer and molecular cloning of the rat nerve growth factor receptor" *Nature* 325:593–597 (Feb. 12, 1987).

Raff, "Social Controls on Cell Survival and Cell Death" *Nature* 356:397–400 (1992).

Raven et al., "Cloning and Functional Analysis of a Novel Protein Which Binds to the p55 TNF Receptor Death Domain" *Programmed Cell Death Meeting* (abstract only) pp. 127 (Sep. 20–24 1995).

Raven et al., "Cloning and Functional Analysis of a Novel Protein Which Binds To The p55 TNF Receptor Death Domain" *Euro. Cytokine Network* (abstract No. 82) 7:210 (Apr.–Jun. 1996).

Ray et al., "Viral Inhibition of Inflammation: Cowpox Virus Encodes an Inhibitor of the Interleukin–1beta Converting Enzyme" *Cell* 69:597–604 (1992).

Reyes et al. "Expression of Human Beta–interferon cDNA Under the Control of a Thymidine Kinase Promoter from Herpes Simplex Virus" *Nature* 297:598–601 (Jun. 17, 1982).

Rice and Baltimore, "Regulated expression of an immunoglobulin κ gene introduced into a mouse lymphoid cell line" *Proc. Natl. Acad. Sci. USA* 79:7862–7865 (1982).

Riechmann et al., "Reshaping Human Antibodies for Therapy" *Nature* 332:323–327 (Mar. 24, 1988).

Ruppert et al., "Cloning and Expression of Human $TAF_{11}250$: a TBP–associated Factor Implicated in Cell–cycle Regulation" *Nature* 362:175–179 (1993).

Sachs et al., "Control of Programmed Cell Death in Normal and Leukemic Cells: New Implications for Therapy" *Blood* 82:15–21 (1993).

Schall et al., "Molecular Cloning and Expression of a Receptor for Human Tumor Necrosis Factor" *Cell* 61:361–370 (Apr. 20, 1990).

Schmid et al., "DNA Fragmentation: Manifestation of Target Cell Destruction Mediated by Cytotoxic T–cell Lines, Lymphotoxin–secreting Helper T–cell Clones, and Cell–free Lymphotoxin–containing Supernatant" *Proc. Natl. Acad. Sci. USA* 83:1881–1885 (1986).

Seckinger et al., "Purification and biologic characterization of a specific tumor necrosis factor α Inhibitor" *Journal of Biological Chemistry* 264:11966–11973 (1989).

Sharon et al., "Expression of a $V_H C_\kappa$ chimaeric protein in mouse myeloma cells" *Nature* 309:364–367 (1984).

Shaw et al., "A General Method for the Transfer of Cloned Genes to Plant Cells" *Gene* 23:315–330 (1983).

Siebenlist et al., "*E. Coli* RNA Polymerase Interacts Homologously with Two Different Promoters" *Cell* 20:269–281 (Jun. 1980).

Sims et al., "A Humanized CD18 Antibody Can Block Function Without Cell Destruction" *The Journal of Immunology* 151(4):2296–2308 (Aug. 1993).

Skinner et al., "Use of the Glu–Glu–Phe C–terminal Epitope for Rapid Purification of the Catalytic Domain of Normal and Mutant ras GTPase–activating Proteins" *Journal of Biological Chemistry* 266:14163–14166 (1991).

Smith et al., "A Receptor for Tumor Necrosis Factor Defines an Unusual Family of Cellular and Viral Proteins" *Science* 248:1019–1023 (May 25, 1990).

Smith et al. "T2 Open reading frame from the shope fibroma virus encodes a soluble form of the TNF receptor" *Biochem. & Biophys. Res. Comm.* 176:335–342 (1991).

Sojar et al., "A Chemical Method for the Deglycosylation of Proteins" *Archives of Biochemistry & Biophysics* 259(1):52–57 (1987).

Southern et al., "Transformation of Mammalian Cells to Antibiotic Resistance with a Bacterial Gene Under Control of the Sv40 Early Region Promoter" *J. Molec. Appl. Genet.* 1:327–341 (1982).

Stamenkovic et al., "A B–lymphocyte activation molecule related to the nerve growth factor receptor and induced by cytokines in carcinomas" *EMBO Journal* 8(5):1403–1410 (1989).

Steller, "Mechanisms and Genes of Cellular Suicide" *Science* 267:1445–1449 (1995).

Stinchcomb et al., "Isolation and Characterisation of a Yeast Chromosomal Replicator" *Nature* 282:39–43 (Nov. 1, 1979).

Suda et al., "Molecular Cloning and Expression of the Fas Ligand, a Novel Member of the Tumor Necrosis Factor Family" *Cell* 75:1169–1178 (1993).

Sugden et al., "A Vector that Replicates as a Plasmid and Can Be Efficiently Selected in B–Lymphoblasts Transformed by Epstein–Barr Virus" *Molecular & Cellular Biology* 5:410–413 (1985).

Suresh et al., "Bispecific Monoclonal Antibodies from Hybrid Hybridomas" *Methods in Enzymology* 121:210–228 (1986).

Suva et al., "A parathyroid hormone–related protein implicated in malignant hypercalcemia: cloning and expression" *Science* 237(4817):893–896 (Aug. 1987).

Takao et al., "Novel DNA Polymorphism in the Mouse Tumor Necrosis Factor Receptors Type 1 and Type 2" *Immunogenetics* 37;199–203 (1993).

Tartaglia et al., "A novel domain within the 55kd TNF receptor signals cell death" *Cell* 74(5):845–853 (1993).

Tewari et al., "Fas– and Tumor Necrosis Factor–induced Apoptosis Is Inhibited by the Poxvirus crmA Gene Product" *Journal of Biological Chemistry* 270:3255–3260 (1995).

Tewari et al., "Yama/CPP32beta, a Mammalian Homolog of CED–3, Is a CrmA–Inhibitable Protease That Cleaves the Death Substrate Poly(ADP–Ribose) Polymerase" *Cell* 81:801–809 (1995).

Thomas et al., "Site–Directed Mutagenesis by Gene Targeting in Mouse Embryo–Derived Stem Cells" *Cell* 51:503–512 (1987).

Thomas, P., "Hybridization of Denatured RNA and Small DNA Fragments Transferred to Nitrocellulose" *Proc. Natl. Acad. Sci. USA* 77(9):5201–5205 (Sep. 1980).

Thompson, "Apoptosis in the Pathogenesis and Treatment of Disease" *Science* 267:1456–1462 (1995).

Thotakura et al., "Enzymatic Deglycosylation of Glycoproteins" *Meth. Enzymol.* 138:350–359 (1987).

Traunecker et al., "Bispecific Single Chain Molecules (Janusins) Target Cytotoxic Lymphocytes on HIV Infected Cells" *EMBO Journal* 10(12):3655–3659 (1991).

Traunecker et al., "Highly Efficient Neutralization of HIV with Recombinant CD4–Immunoglobulin Molecules" *Nature* 339:68–70 (1989).

Tschumper et al., "Sequence of a Yeast DNA Fragment Containing a Chromosomal Replicator and the TRP1 Gene" *Gene* 10:157–166 (1980).

Upton et al., "Myxoma virus expresses a secreted protein with homology to the tumor necrosis factor receptor gene family that contributes to viral virulence" *Virology* 184:370–382 (1991).

Upton et al., "Tumorigenic poxviruses: genomic organization and DNA sequence of the telomeric region of the shope fibroma virus genome" *Virology* 160:20–29 (1987).

Urlaub et al., "Isolation of Chinese Hamster Cell Mutants Deficient in Dihydrofolate Reductase Activity" *Proc. Natl. Acad. Sci. USA* 77(7):4216–4220 (Jul. 1980).

Van den Berg et al., "Kluyveromyces as a Host for Heterologous Gene Expression: Expression and Secretion of Prochymosin" *Bio/Technology* 8:135–139 (1990).

Van Solingen et al., "Fusion of Yeast Spheroplasts" *J. Bact.* 130:946–947 (1977).

Verhoeyen et al., "Reshaping Human Antibodies: Grafting an Antilysozyme Activity" *Science* 239:1534–1536 (Mar. 25, 1988).

Watanabe–Fukunaga et al., "Lymphoproliferation Disorder in Mice Explained by Defects in Fas Antigen that mediates Apoptosis" *Nature* 356:314–317 (1992).

Welcher et al., "Nerve growth factor binding domain of the nerve growth factor receptor" *Proc. Natl. Acad. Sci. USA* 88:159–163 (1991).

Wiley et al., "Identification and Characterization of a New Member of the TNF Family that Induces Apoptosis" *Immunity* 3:673–682 (1995).

Yan and Chao, "Disruption of Cysteine–rich repeats of the p75 nerve growth factor receptor leads to loss of ligand binding" *Journal of Biological Chemistry* 266:12099–12104 (1991).

Yaniv, M., "Enhancing Elements for Activation of Eukaryotic Promoters" *Nature* 297(6):17–18 (May 1982).

Yonehara et al., "A cell–killing monoclonal antibody (anti–Fas) to a cell surface antigen co–downregulated with the receptor of tumor necrosis factor" *Journal of Experimental Medicine* 169:1747–1756 (1989).

Zheng et al., "Induction of Apoptosis in Mature T Cells by Tumor Necrosis Factor" *Nature* 377:348–351 (1995).

Zola, "Using Monoclonal Antibodies: Soluble Antigens" *Monoclonal Antibodies: A Manuel of Techniques*, CRC Press, Chapter 6, pp. 147–158 (1987).

Zoller et al., "Oligonucleotide–directed Mutagenesis Using M13–derived Vectors: An Efficient and General Procedure for the Production of Point Mutations in Any Fragment of DNA" *Nucl. Acids Res.* 10(20):6487–6500 (1982).

* cited by examiner

```
   1 GAATTCCGGCGGGAGGCCGAGAGAGAAGTCACTTGCCCTGCTCTACCTTGAAGTGTTCTCAGGGTTGGGCGAGAGAGTCGGGGTGGGGACCGAGATGC
 101 AGCTCTATCCTGTGCCCCTGGTCGCAGACAGGCAGCCCAGCGCCTTCGCTGTCCTGTTCTACTTGGCCTGTCCGCTGCCGCTGCCGCTGCCGCTGCCGCTGCTGAG
 201 CAGAGGGGCCACCTGGTCGGACTCGGTTGGGCTCGGGGACCCTCCCGGCCGGCCGCCCCTTCTCGACGGCGGGCCCTTCTCGACGGCGGGCCCTGCGG
 301 GCGCGGGGGCTGAAGGCGGAACGGGGAGAGCGCACGGAGCCGGGAAGCCCCCTGGGCGCGCCCCTGGGAGGCTATGAGCAGCCGCGGGGGCTGC
     1                                                                 M  E  Q  R  P  R  G  C
 401 GCGGCGGTGGCGGCGGCGCTCCTCGTTGTGCTGCTGGGGGCCCGGGCCCAGGGCGGCACTCGTAGCCCCAGGTGTGACTGTCCGGTGACTTCCACAAGA
   9  A  A  V  A  A  A  L  L  L  V  L  L  G  A  R  A  Q  G  G  T  R  S  P  R  C  D  C  A  G  D  F  H  K
 501 AGATTGGTCTGTTTTGTTGCAGAGGCTGCCCAGCGGGCACTACTGAAGGCCCCTTGCACGGAGCCCTGTGCACTGAGCCTCCAGGTGCGCTGAGAACTGTTCA
  43  I  G  L  F  C  C  R  G  C  P  A  G  H  Y  L  K  A  P  C  T  E  P  C  G  N  S  T  C  L  V  C  P  Q
 601 AGACACCTTCTTTGGCTTGGGAGAACCACCATAATTCTGAATGTGCCCGCTGCCAGGCCCAGTGCGCTGAGAACTGTTCA
  76  D  T  F  F  L  A  W  E  N  H  H  N  S  E  C  A  R  C  Q  A  C  D  E  Q  A  S  Q  V  A  L  E  N  C  S
 701 GCAGTGGCCGACACCCGCTGTGGCTGTAAGCCAGGCTGGTTTGTGGAGTGCCAGGTGCAGGTGCAGTTCACCCTTCACGTTGTCAGCAGTTCAGCGAGTGTCAGCAGTGCCAATGTGTCAGCAGTTCACCCTTCTACTGCCAACCATGCC
 109  A  V  A  D  T  R  C  G  C  K  P  G  W  F  V  E  C  Q  V  S  S  Q  C  V  S  S  P  F  Y  C  Q  P  C  L
 801 TAGACTGCGGGGCCCTGCACCGGCACCCGCTAAGACAGGCTGCGACCTGCAGAGATACTGACTGTGGACGTGAGCTTCTATGAACATGGCGATGG
 143  D  C  G  A  L  H  R  H  T  R  L  L  C  S  R  R  D  T  D  C  G  T  C  L  P  G  F  Y  E  H  G  D  G
 901 CTGCCGTGTCCTGCCCCACGTAATTCCTAGCTGTCGTGGATGAGGAGCGAAGGGCGTGGAGACAGAGCAGGCCTGGGGCTGGGGCCAGGTGCTGTGGTT
 176  C  V  S  C  P  T
1001 CAGGAATAGGAAGAGGGATAGGAGGAGGAGGGAGCCTTGGCCCTGTGATGGTGGCCCCCACTTCAGGCAAACTTAGATGCAAAAGAGCAATCTGGATCC
1101 GCCTTAGCCAGATACATAAGGGTATTGCCTTCACTTCAGCCAGCATTCCCCCAGCGATCCTAGCCAGATATTACAGATGATTGTCACTTACACAGA
1201 GAGTCACATTGATATAGCTTTAAAACTTGGGCTGAAGGAGGTTGAGGCTGCACTTCAGCCTGCCACTGCGTCCAGTGAGCTATGATCGTCGCCAACAGAGCCGAG
1301 ACCTATTAAATAAATAAATATTAAATCTATTAAATATTAAATCTATTAAATATTAAATCTATTAAATCTATTAAATAAATAAATACAAGGGCTGAGAGTCAGGACTCAGGACTGTGCTGC
1401 TAGTTCTCTAGGGATCTTGGGCAAGTGCAGAGAATTC
```

```
   1 TTTCCCTCACTGACTATAAAGAATAGAAGGAAGGGCTTCAGTGACCGGCTGCCTGCTGACTTACAGCAGTCAGACTCTGACAGGATC

91 ATGGCTATGATGGAGGTCCAGGGGGGACCCAGCCTGGGACAGACCTGCCTGCTGCTGCCTGATCGTGCTGATCTTCACAGTGCTGCCTGCAGTCTCTGT
   1 MetAlaMetMetGluValGlnGlyGlyProSerLeuGlyValGlnThrCysValLeuIlePheThrValLeuLeuGlnSerLeuCys

181 GTGGCTGTGTAACTTACGTGTACTTTAACCAACGAGCTGAAGCAGATGCAGGACAAGACTACTCCAAAAGTGCTTGTTTCTTAAAAGAA
  31 ValAlaValThrTyrValTyrPheThrAsnGluLysGlnMetGlnAspLysThrThrProLysValLeuValSerPheLeuLysGlu

271 GATGACAGTTATTGGGACCCCAATGACGAAGAGTATGAACAGCCCCTGCTGCAAGTCAAGTGGCAACTCCGTCAGCTCGTTAGAAAAG
  61 AspAspSerTyrTrpAspProAsnAspGluGluTyrGluGlnProLeuLeuGlnValLysTrpGlnLeuArgGlnLeuValArgLys

361 ATGATTTTGAGAACCTCTGAGGAAACCATTTCTACAGTTCAAGAAAAACAAAAAATATTTCTCCCCTAGTGAGAGAAGAGGTCCTCAG
  91 MetIleLeuArgThrSerGluGluThrIleSerThrValGlnGluLysGlnAsnIleSerProLeuValArgGluArgGlyProGln

451 AGAGTAGCAGCTCACATAACTGGACCAGAGGAAGAAGCAACACATTGTCTTCTCCAAACTCCAAGAATGAAAAGGCTCTGGGCCGCAAA
 121 ArgValAlaAlaHisIleThrGlyThrArgGlyGluGluAlaThrHisCysLeuLeuGlnThrProArgAsnGluLysAlaLeuGlyArgLys

541 ATAAACTCCTGGGAATCATCAAGGAGTGGGCATTCATTCCTGAGCAACTTGCACTTGAGGAATGGTGAACTGGTCATCCATGAAAAGGG
 151 IleAsnSerTrpGluSerSerArgSerGlyHisSerPheLeuSerAsnLeuHisLeuArgAsnGlyGluLeuValIleHisGluLysGly

631 TTTTACATCTATTCCAAACATACTTTCGATTTCTATATATTGTTGAAGAGAAAAACACAAAGAACGACAAAGAACACACAATGGTCCAATATATT
 181 PheTyrTyrIleTyrIleThrTyrProPheArgPheLeuTyrIleLeuLeuGluValGluLysAsnThrLysGluAsnThrLysGlnMetValGlnTyrIle

721 TACAAATACACAAGTTATCCTGACCCTATATTGTTGATGAAAAGTGCTAGAAATGCTAAAGATGCAGAATATGACTCTAT
 211 TyrLysTyrThrSerTyrProAspProIleLeuLeuMetLysSerAlaArgAsnSerCysTrpSerLysAspAlaGluTyrGlyLeuTyr

811 TCCATCTATCAAGGGGAATATTTGAGCTTAAGGAAAATGACAGAATTTTTGTTTTCTGTAACAAATGAGCACTTGATAGACATGGACCAT
 241 SerIleTyrGlnGlyIleGlyIlePheGluLysGluLysGluAsnAspArgIlePheValSerValThrAsnGluHisLeuIleAspMetAspHis

901 GAAGCCAGTTTTTTCGGGGCCTTTTAGTTGGCTAACTGACCTGGAAAGAAAAAGCAATAACCTCAAAGTGACTATTCAGTTTTCAGGAT
 271 GluAlaSerPhePheGlyAlaPheLeuValGlyStp

991 GATACACTATGAAGATGTTTCAAAAAATCTGACCAAAAACAAAACAGAAA
```

FIG. 4

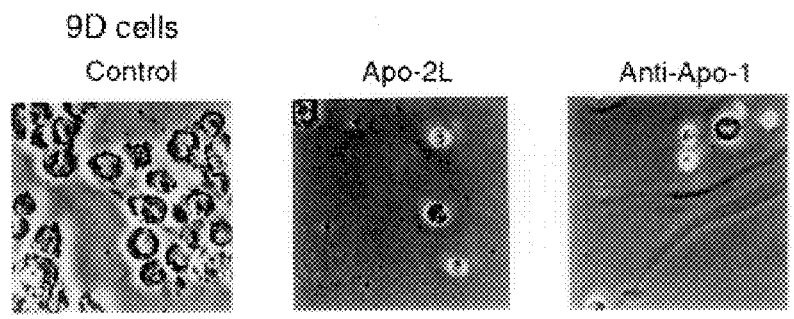
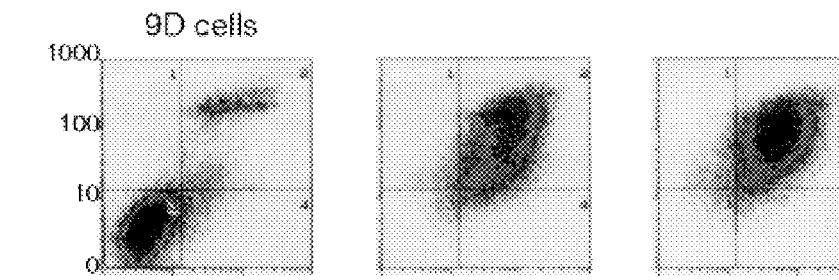
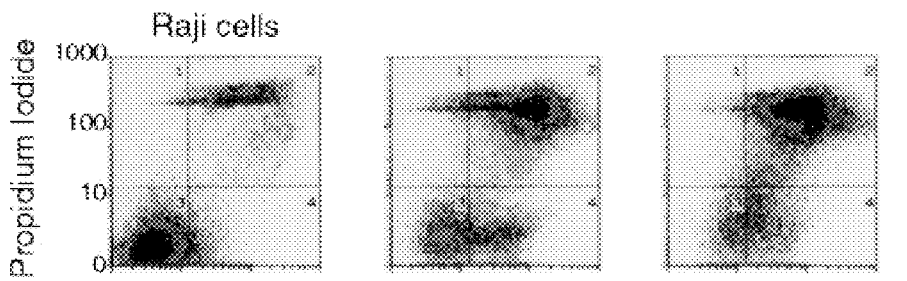
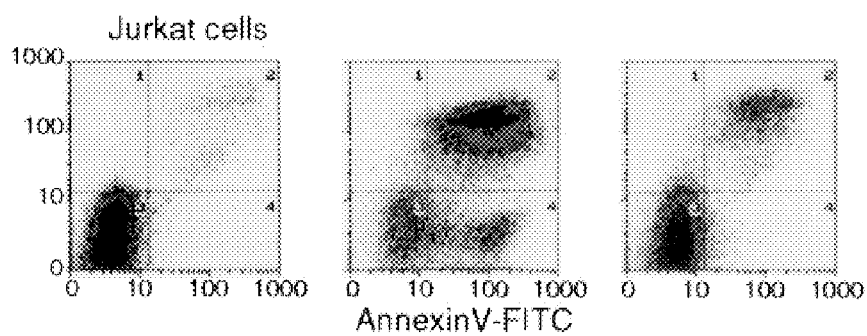
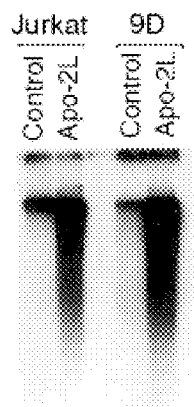
FIG. 6A
FIG. 6B
FIG. 6C
FIG. 6D
FIG. 6E

```
  1 CGGGCCCTGC GGGCGGCGGGG CTGAAGGCGG AACCACGACG GGCAGAGAGC ACGGAGCCGG

61 GAAGCCCCTG GGCGCCCGTC GGAGGGCTAT GGAGCAGCGG CCGCGGGGCT CCGGGGGCGT
  1                                  M  E  Q  R  P  R  G   A  A  V

121 GGCGGGGGCG CTCCTCCTGG TGCTGCTGGG GGCCCCGGGC CAGGGGCGGCA CTCGTAGCCC
 12  A  A  L  L  L  V  L  L  G  A  R  A   Q  G  G  T  R  S  P

181 CAGGTGTGAC TGTGCCGGTG ACTTCCACAA GAAGATTGGT CTGTTTTGTT GCAGAGGCTG
 32  R  C  D  C  A  G  D  F  H  K  K  I  G  L  F  C  C  R  G  C

241 CCCAGCGGGG CACTACCTGA AGGCCCCTTG CACGGAGCCC TGCGGCAACT CCACCTGCCT
 52  P  A  G  H  Y  L  K  A  P  C  T  E  P  C  G  N  S  T  C  L

301 TGTGTGTCCC CAAGACACCT TCTTGGCCTG CATAATTCTG AATGTGCCCG
 72  V  C  P  Q  D  T  F  L  A  W  *  H  N  S  E  C  A  R

361 CTGCCAGGCC TGTGATGAGC AGGCCTCCCA GGTGGCGCTG GAGAACTGTT CAGCAGTGGC
 92  C  Q  A  C  D  E  Q  A  S  Q  V  A  L  E  N  C  S  A  V  A

421 CGACACCCGC TGTGGCTGTA AGCCAGGCTG GTTTGTGGAG TGCCAGGTCA GCCAATGTGT
112  D  T  R  C  G  C  K  P  G  W  F  V  E  C  Q  V  S  Q  C  V

481 CAGCAGTTCA CCCTTCTACT GCCAACCATG CCTAGACTGC GGGCCCCTGC ACCGCCACAC
132  S  S  S  P  F  Y  C  Q  P  C  L  D  C  G  A  L  H  R  H  T
```

FIG. 8A

```
541  ACGGCTACTC TGTTCCCGCA GAGATACTGA CTGTGGGACC TGCCTGCCTG GCTTCTATGA
152   R  L  L   C  S  R  R   D  T  D    C  G  T    C  L  P  G    F  Y  E

601  ACATGGCGAT GGCTGCCTGT CCTGCCCCAC GAGCACCCTG GGGAGCTGTC CAGAGCGGCTG
172   H  G  D   G  C  V  S   C  P  T    S  T  L    G  S  C  P    E  R  C

661  TGCCGCTGTC TGTGGCTGGA GGCAGATGTT CTGGGTCCAG GTGCTCCTGG CTGGCCTTGT
192   A  A  V   C  G  W  R   Q  M  F    W  V  Q    V  L  L  A    G  L  V

721  GGTCCCCCTC CTGCTTGGGG CCACCCTGAC CTACACATAC CGCCACTGCT GGCCTCACAA
212   V  P  L   L  L  G  A   T  L  T    Y  T  Y    R  H  C  W    P  H  K

781  GCCCCTGGTT ACTGCAGATG AAGCTGGGAT GGAGGCTCTG ACCCCACCAC CGGCCACCCA
232   P  L  V   T  [A] D  E   A  G  M    E  A  L    T  P  P  P    A  T  H

841  TCTGTCACCC TTGGACAGCG CCCACACCCT TCTAGCACCT CCTGACAGCA GTGAGAAGAT
252   L  S  P   L  D  S  A   H  T  L    A  P  P    D  S  S  E    K  I

901  CTGCACCGTC CAGTTGGTGG GTAACAGCTG GACCCCTGGC TACCCCGAGA CCCAGGAGGC
272   C  T  V   Q  L  V  G   N  S  W    T  P  G    Y  P  E  T    Q  E  A

961  GCTTCTGCCG CAGGTGACAT GGTCCTGGGA CCAGTTGCCC AGCAGAGCTC TTGGCCCCGC
292   L  C  P   Q  V  T  W   S  W  D    Q  L  P    S  R  A  L    G  P  A

1021 TGCTGGGCCC ACACTCTCGC CAGAGTCCCC AGCCGGCTCG CCAGCCATGA TGCTGCAGCC
312   A  A  P   T  L  S  P   E  S  P    A  G  S    P  A  M  M    L  Q  P
```

FIG. 8B

```
1081  GGGCCCCGCAG CTCTACGACG TGATGGACGC GGTCCCAGCG CGGGGCTTGA AGGAGTTCGT
 332       G  P  Q   L  Y  D  V  M  D  A  V  P  A  R  R  W  K  E  F  V

1141  GCGCACGCTG GGGCTGCGCG AGGCAGAGAT CGAAGCCGTG GAGGTGGAGA TCGGCCGCTT
 352   R  T  L  G  L  R  E  A  E  I  E  A  V  E  V  E  I  G  R  F

1201  CCGAGACCAG CAGTACGAGA TGCTCAAGCG CTGGCGCCAG CAGCAGCCCG CGGGCCTCGG
 372   R  D  Q  Q  Y  E  M  L  K  R  W  R  Q  Q  Q  P  A  G  L  G

1261  AGCCGTTTAC GCGGCCCTGG AGCGCATGGG GCTGGACGGC TGCGTGGAAG ACTTGCGCAG
 392   A  V  Y  A  A  L  E  R  M  G  L  D  G  C  V  E  D  L  R  S

1321  CCGGCCTGCAG CGCGGCCCGT GACACGGCGC CCACTTGCCA CCTAGGCGCT CTGGTGGCCC
 412   R  L  Q  R  G  P

1381  TTGCAGAAGC CCTAAGTACG GTTACTTATG CGTGTAGACA TTTTATGTCA CTTATTAAGC

1441  CGCTGGCACG GCCCTGCGTA GCAGCACCAG CCGGCCCCAC CCCTGCTCGC CCCTATGCT

1501  CCAGCCAAGG CGAAGAAGCA CGAACGAATG TCGAGAGGGG GTGAAGACAT TTCTCAACTT

1561  CTCGGCCCGGA GTTTGGCTGA GATCGCGGTA TTAAATCTGT GAAAGAAAAC AAAAAAAAA

1621  AAAAAAAAA AAAA
```

FIG. 8C

```
po3       1                                      MEQRPRGCAAVAAALLVLLGARAQGGTRSPR------
NFR1      1                                      MGLSTVPDLLLPL-VLLELLVGIYPSGVIGLVPHLGDREKRDSV
as/Apo1   1                                      MLGIWTLLPLVLTSVARLSSKSVNAQVTDINSKGLELRKTVTTV po3      33   CDCAGDFHKKIGLFCCRGCPAGHYLKAPCTEPCGNSTCLV
NFR1     44   CPQGKYIHPQNNSICCTKCHKGTYLYNDCPGPGQDTDCRE
as/Apo1  45   ETQNLEGLHHDGQFCHKPCEPGERKARDCTVNGDEPDCVP po3      73   CPQDTFLAWENHHNSECARCQACDEQASQVALENCSAVADTRCG
NFR1     85   CESGSFTASENHLRH-CLSCRKCRKEMGQVEISSCTVDRDTVCG
as/Apo1  85   CQEGKEYTDKAHFSSKCRRCRLCDEGHGLEVEINCTRTQNTKCR po3     117   CKPGWFVECQVSSSPFYCQPCLDCGALHRHTRLLCSRRD-TDCGT
NFR1    127   CRKNQYRHYWSENLFQ--CFNCSLCLNGTVHLS--CQEKQNTVCT-
as/Apo1 129   CKPNFF--CNSTVCEH--CDPCTKCEHGIIKE--CTLTSNTKCKE po3     165   CLPGFYEHGDGCVSCPTSTLGSCP--ERCAAVCGW
NFR1    168   CHAGFFLRENECVSCS-----NCKKSLECTKLCLP
```

FIG. 9

|  |  |  |
|---|---|---|
| Apo3 | 338 | VMDAVPARRWKEFVRTLGLREAEIEAVEVEIGR--FRDQQYE |
| TNFR1 | 333 | VVENVPPLRWKEFVRRLGLSDHEIDRLELQNGR-CLREAQYS |
| Fas/Apo1 | 220 | IAGVMTLSQVKGFVRKNGVNEAKIDEIKNDNVQDTAEQKV-Q |
| FADD | 104 | ICDNVGK-DWRRLARQLKVSDTKIDSIEDRYPRN-LTERVRE |
| TRADD | 211 | NRPLSLK-DQQTEARSVGLKWRKVGR-SLQRGCRALRDPALD |
| RIP | 291 | IRENLGK-HWKNCARKLGFTQSAIDEIDHDYERDGLKEKVYQ |
| Reaper | 1 | MAVAFYIPDQATLLREAEQKEQILR-LRESQWR |

|  |  |  |
|---|---|---|
| Apo3 | 378 | MLKRWRQQQP---AGLGAVYAALERMGL-DGCVEDLRS |
| TNFR1 | 374 | MLATWRRRTPRREATLELLGRVLRDMDL-LGCLEDIEE |
| Fas/Apo1 | 261 | LLRNWHQLHG-KKEAYDTLIKDLKKANLCTLA-EKIQT |
| FADD | 144 | SLRIWKNTE-KENATVAHLVGALRSC--QMNLVADLV |
| TRADD | 251 | SLAYEYEREGLYEQAFQLLRRFV-QAEGRRATLQRLVE |
| RIP | 332 | MLQKWVMREGIKGATVGKLAQALHQC--SRIDLSSLT |
| Reaper | 34 | FLATVVLETLKQYTSCHPKTGRKSGKYRKP |

FIG. 10

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 181 amino acids
      (B) TYPE: Amino Acid
      (D) TOPOLOGY: Linear (xi) SEQUENCE DESCRIPTION: SEQ ID NO:1:

```
Met Glu Gln Arg Pro Arg Gly Cys Ala Ala Val Ala Ala Ala Leu
 1               5                  10                  15

Leu Leu Val Leu Leu Gly Ala Arg Ala Gln Gly Gly Thr Arg Ser
                20                  25                  30

Pro Arg Cys Asp Cys Ala Gly Asp Phe His Lys Lys Ile Gly Leu
                35                  40                  45

Phe Cys Cys Arg Gly Cys Pro Ala Gly His Tyr Leu Lys Ala Pro
                50                  55                  60

Cys Thr Glu Pro Cys Gly Asn Ser Thr Cys Leu Val Cys Pro Gln
                65                  70                  75

Asp Thr Phe Leu Ala Trp Glu Asn His His Asn Ser Glu Cys Ala
                80                  85                  90

Arg Cys Gln Ala Cys Asp Glu Gln Ala Ser Gln Val Ala Leu Glu
                95                  100                 105
```

```
Asn Cys Ser Ala Val Ala Asp Thr Arg Cys Gly Cys Lys Pro Gly
                110                 115                 120

Trp Phe Val Glu Cys Gln Val Ser Gln Cys Val Ser Ser Pro
            125                 130                 135

Phe Tyr Cys Gln Pro Cys Leu Asp Cys Gly Ala Leu His Arg His
            140                 145                 150

Thr Arg Leu Leu Cys Ser Arg Arg Asp Thr Asp Cys Gly Thr Cys
                155                 160                 165

Leu Pro Gly Phe Tyr Glu His Gly Asp Gly Cys Val Ser Cys Pro
                170                 175                 180

Thr
181
```

(2) INFORMATION FOR SEQ ID NO:2:

(i) SEQUENCE CHARACTERISTICS:
        (A) LENGTH: 433 base pairs
        (B) TYPE: Nucleic Acid
        (C) STRANDEDNESS: Single
        (D) TOPOLOGY: Linear (xi) SEQUENCE DESCRIPTION: SEQ ID NO:2:

```
CTGCTGGGGG CCCGGGCCAG NGGCGGCACT CGTAGCCCCA GGTGTGACTG          50

TGCCGGTGAC TTCCACAAGA AGATTGGTCT GTTTTGTTGC AGAGGCTGCC         100

CAGCGGGGCA ACTACCTGAA GGCCCCTTGC ACGGAGCCCT GCGCAACTCC         150

ACCTGCCTTG TGTGTCCCCA AGACACCTTC TTGGCCTGGG AGAACCACCA         200

TAATTCTGAA TGTGCCCGCT GCCAGGCCTG TGATGAGCAG GCCTCCCAGG         250

TGGCGCTGGA GAACTGTTCA GCAGTGGCCG ACACCCGCTG TGGCTGTAAG         300

CAGGGCTGGT TTGTGGAGTG CCAGGGTCAG CCAATGTGTC AGCAGTTTCA         350

CCCTTCTAAT GCCAACCATG CCTAGACTGC GGGGCCCTGC AACGCAACAC         400

ACGGCTAATN TGTTTCCCGC AGAGATNATT GTT                           433
```

(2) INFORMATION FOR SEQ ID NO:3:

(i) SEQUENCE CHARACTERISTICS:
        (A) LENGTH: 28 base pairs
        (B) TYPE: Nucleic Acid
        (C) STRANDEDNESS: Single
        (D) TOPOLOGY: Linear (xi) SEQUENCE DESCRIPTION: SEQ ID NO:3:

```
CCCGCTGCCA GGCCTGTGAT GAGCAGGC                                  28
```

(2) INFORMATION FOR SEQ ID NO:4:

(i) SEQUENCE CHARACTERISTICS:
        (A) LENGTH: 28 base pairs
        (B) TYPE: Nucleic Acid
        (C) STRANDEDNESS: Single
        (D) TOPOLOGY: Linear (xi) SEQUENCE DESCRIPTION: SEQ ID NO:4:

```
CAGGGCCCCG CAGTCTAGGC ATGGTTGG                                  28
```

(2) INFORMATION FOR SEQ ID NO:5:

(i) SEQUENCE CHARACTERISTICS:
        (A) LENGTH: 1438 base pairs
        (B) TYPE: Nucleic Acid (C) STRANDEDNESS: Single
            (D) TOPOLOGY: Linear (xi) SEQUENCE DESCRIPTION: SEQ ID NO:5:

| | |
|---|---:|
| GAATTCCGGC GCGGAGGCCG AGAGAGAAGT CACTTGCCCT GGCTCTACCT | 50 |
| TGAAGTGGTT CTCAGGGTTG GGGCGAGAGT CGGGGTGGGG ACCGAGATGC | 100 |
| AGCTCTATCC TGTGCCCCTG GTCGCAGCAG GCAGCCCAGC GCTTCGCGTG | 150 |
| TTCTACTTGG CCTGTCCGCT GCCGCCTAAT GAGCTCAGGT CTAGGCCGAG | 200 |
| CAGAGGGGGC ACCTGGTCGG ACTCGGTTGG GCTCGGGCGG CCCCGCCTCC | 250 |
| CCCCGCCCGC CAGGCGGGCC CTTCTCGACG GCGCGGGGCG GGCCCTGCGG | 300 |
| GCGCGGGGCT GAAGGCGGAA CCACGACGGG CAGAGAGCAC GGAGCCGGGA | 350 |
| AGCCCCTGGG CGCCCGTCGG AGGGCTATGG AGCAGCGGCC GCGGGGCTGC | 400 |
| GCGGCGGTGG CGGCGGCGCT CCTCCTGGTG CTGCTGGGGG CCCGGGCCCA | 450 |
| GGGCGGCACT CGTAGCCCCA GGTGTGACTG TGCCGGTGAC TTCCACAAGA | 500 |
| AGATTGGTCT GTTTTGTTGC AGAGGCTGCC CAGCGGGGCA CTACCTGAAG | 550 |
| GCCCCTTGCA CGGAGCCCTG CGGCAACTCC ACCTGCCTTG TGTGTCCCCA | 600 |
| AGACACCTTC TTGGCCTGGG AGAACCACCA TAATTCTGAA TGTGCCCGCT | 650 |
| GCCAGGCCTG TGATGAGCAG GCCTCCCAGG TGGCGCTGGA GAACTGTTCA | 700 |
| GCAGTGGCCG ACACCCGCTG TGGCTGTAAG CCAGGCTGGT TTGTGGAGTG | 750 |
| CCAGGTCAGC CAATGTGTCA GCAGTTCACC CTTCTACTGC CAACCATGCC | 800 |
| TAGACTGCGG GGCCCTGCAC CGCCACACAC GGCTACTCTG TTCCCGCAGA | 850 |
| GATACTGACT GTGGGACCTG CCTGCCTGGC TTCTATGAAC ATGGCGATGG | 900 |
| CTGCGTGTCC TGCCCCACGT AATTCCTAGC TGTCGTGGGA TGGAGGGAAG | 950 |
| GGCGGCTGGG AGCAGAGCAG GGGCCTGGGG TGGGGCAGGT GCTGCTGGTT | 1000 |
| CAGGAATAGG AAGAGGGGAT AGGGAGGAGG GAGCCTTGGC CCTGTGATGG | 1050 |
| GTGGGCCCCA CTTCAGGCAA ACTTAGATGG CAAAAGAGCA ATCTGGATCC | 1100 |
| GCCTTAGCCA GATACATAAG GGTATTTGCC TTCACTTTCA GCCAGCATTC | 1150 |
| CCCCCAGCGA TCCTAGCCAG ATATTACAGA TGATTTGTCA CTTACACAGA | 1200 |
| GAGTCACATT GATATAGCTT TAAAACTTGG GCTGAAGGAG GTTGAGGCTG | 1250 |
| CAGTGAGCTA TGATCGTGCC ACTGCACTTC AGCCTGGGCA ACAGAGCGAG | 1300 |
| ACCTATTAAA TAAATAAATA AATATTAAAT CTATTAAATA TTAAATATTA | 1350 |
| AATCTATTAA ATAAATAAAT ACAAAGGGCT GAGAGTCAGG ACTGTGCTGC | 1400 |
| TAGTTCTCTA GGGGATCTTG GGCAAGTGCA GAGAATTC | 1438 |

(2) INFORMATION FOR SEQ ID NO:6:

(i) SEQUENCE CHARACTERISTICS:
        (A) LENGTH: 390 base pairs
        (B) TYPE: Nucleic Acid
        (C) STRANDEDNESS: Single
        (D) TOPOLOGY: Linear (xi) SEQUENCE DESCRIPTION: SEQ ID NO:6:

| | |
|---|---:|
| GGGACCCCAA TGACGAAGAG AGTATGAACA GCCCCTGCTG GCAAGTCAAG | 50 |
| TGGCAACTCC GTCAGCTCGT TAGAAAGATG ATTTTGAGAA CCTCTGAGGA | 100 |
| AACCATTTCT ACAGTTCAAG AAAAGCAACA AAATATTTCT CCCCTAGTGA | 150 |

```
GAGAAAGAGG TCCTCAGAGA GTAGCAGCTC ACATAACTGG GACCAGAGGA          200

AGAAGCAACA CATTGTCTTC TCCAAACTCC AAGAATGAAA AGGCTCTGGG          250

CCGCAAAATA AACTCCTGGG AATCATCAAG GAGTGGGCAT TCATTCCTGA          300

GCAACTTGCA CTTGAGGAAT GGTGAACTGG TCATCCATGA AAAAGGGTTT          350

TACTACATCT ATTCCCAAAC ATACTTTCGA TTTCAGGAGG                    390
```

(2) INFORMATION FOR SEQ ID NO:7:

(i) SEQUENCE CHARACTERISTICS:
        (A) LENGTH: 60 base pairs
        (B) TYPE: Nucleic Acid
        (C) STRANDEDNESS: Single
        (D) TOPOLOGY: Linear (xi) SEQUENCE DESCRIPTION: SEQ ID NO:7:

```
TGACGAAGAG AGTATGAACA GCCCCTGCTG GCAAGTCAAG TGGCAACTCC          50

GTCAGCTCGT                                                     60
```

(2) INFORMATION FOR SEQ ID NO:8:

(i) SEQUENCE CHARACTERISTICS:
        (A) LENGTH: 60 base pairs
        (B) TYPE: Nucleic Acid
        (C) STRANDEDNESS: Single
        (D) TOPOLOGY: Linear (xi) SEQUENCE DESCRIPTION: SEQ ID NO:8:

```
GGTGAACTGG TCATCCATGA AAAAGGGTTT TACTACATCT ATTCCCAAAC          50

ATACTTTCGA                                                     60
```

(2) INFORMATION FOR SEQ ID NO:9:

(i) SEQUENCE CHARACTERISTICS:
        (A) LENGTH: 24 amino acids
        (B) TYPE: Amino Acid
        (D) TOPOLOGY: Linear (xi) SEQUENCE DESCRIPTION: SEQ ID NO:9:

```
Met Gly His His His His His His His His His His Ser Ser Gly
 1               5                  10                  15

His Ile Asp Asp Asp Asp Lys His Met
                20              24
```

(2) INFORMATION FOR SEQ ID NO:10:

(i) SEQUENCE CHARACTERISTICS:
        (A) LENGTH: 417 amino acids
        (B) TYPE: Amino Acid
        (D) TOPOLOGY: Linear (xi) SEQUENCE DESCRIPTION: SEQ ID NO:10:

```
Met Glu Gln Arg Pro Arg Gly Cys Ala Ala Val Ala Ala Ala Leu
 1               5                  10                  15

Leu Leu Val Leu Leu Gly Ala Arg Ala Gln Gly Gly Thr Arg Ser
                20                  25                  30

Pro Arg Cys Asp Cys Ala Gly Asp Phe His Lys Lys Ile Gly Leu
                35                  40                  45

Phe Cys Cys Arg Gly Cys Pro Ala Gly His Tyr Leu Lys Ala Pro
                50                  55                  60
```

```
Cys Thr Glu Pro Cys Gly Asn Ser Thr Cys Leu Val Cys Pro Gln
                 65                  70                  75

Asp Thr Phe Leu Ala Trp Glu Asn His His Asn Ser Glu Cys Ala
                 80                  85                  90

Arg Cys Gln Ala Cys Asp Glu Gln Ala Ser Gln Val Ala Leu Glu
                 95                 100                 105

Asn Cys Ser Ala Val Ala Asp Thr Arg Cys Gly Cys Lys Pro Gly
                110                 115                 120

Trp Phe Val Glu Cys Gln Val Ser Gln Cys Val Ser Ser Ser Pro
                125                 130                 135

Phe Tyr Cys Gln Pro Cys Leu Asp Cys Gly Ala Leu His Arg His
                140                 145                 150

Thr Arg Leu Leu Cys Ser Arg Arg Asp Thr Asp Cys Gly Thr Cys
                155                 160                 165

Leu Pro Gly Phe Tyr Glu His Gly Asp Gly Cys Val Ser Cys Pro
                170                 175                 180

Thr Ser Thr Leu Gly Ser Cys Pro Glu Arg Cys Ala Ala Val Cys
                185                 190                 195

Gly Trp Arg Gln Met Phe Trp Val Gln Val Leu Leu Ala Gly Leu
                200                 205                 210

Val Val Pro Leu Leu Leu Gly Ala Thr Leu Thr Tyr Thr Tyr Arg
                215                 220                 225

His Cys Trp Pro His Lys Pro Leu Val Thr Ala Asp Glu Ala Gly
                230                 235                 240

Met Glu Ala Leu Thr Pro Pro Pro Ala Thr His Leu Ser Pro Leu
                245                 250                 255

Asp Ser Ala His Thr Leu Leu Ala Pro Pro Asp Ser Ser Glu Lys
                260                 265                 270

Ile Cys Thr Val Gln Leu Val Gly Asn Ser Trp Thr Pro Gly Tyr
                275                 280                 285

Pro Glu Thr Gln Glu Ala Leu Cys Pro Gln Val Thr Trp Ser Trp
                290                 295                 300

Asp Gln Leu Pro Ser Arg Ala Leu Gly Pro Ala Ala Ala Pro Thr
                305                 310                 315

Leu Ser Pro Glu Ser Pro Ala Gly Ser Pro Ala Met Met Leu Gln
                320                 325                 330

Pro Gly Pro Gln Leu Tyr Asp Val Met Asp Ala Val Pro Ala Arg
                335                 340                 345

Arg Trp Lys Glu Phe Val Arg Thr Leu Gly Leu Arg Glu Ala Glu
                350                 355                 360

Ile Glu Ala Val Glu Val Glu Ile Gly Arg Phe Arg Asp Gln Gln
                365                 370                 375

Tyr Glu Met Leu Lys Arg Trp Arg Gln Gln Gln Pro Ala Gly Leu
                380                 385                 390

Gly Ala Val Tyr Ala Ala Leu Glu Arg Met Gly Leu Asp Gly Cys
                395                 400                 405

Val Glu Asp Leu Arg Ser Arg Leu Gln Arg Gly Pro
                410                 415     417

(2) INFORMATION FOR SEQ ID NO:11:

(i) SEQUENCE CHARACTERISTICS:
        (A) LENGTH: 1634 base pairs
        (B) TYPE: Nucleic Acid
        (C) STRANDEDNESS: Single
```

(D) TOPOLOGY: Linear (xi) SEQUENCE DESCRIPTION: SEQ ID NO:11:

```
CGGGCCCTGC GGGCGCGGGG CTGAAGGCGG AACCACGACG GGCAGAGAGC           50

ACGGAGCCGG GAAGCCCCTG GGCGCCCGTC GGAGGGCT ATG GAG               94
                                         Met Glu
                                           1

CAG CGG CCG CGG GGC TGC GCG GCG GTG GCG GCG GCG CTC            133
Gln Arg Pro Arg Gly Cys Ala Ala Val Ala Ala Ala Leu
          5                  10                  15

CTC CTG GTG CTG CTG GGG GCC CGG GCC CAG GGC GGC ACT            172
Leu Leu Val Leu Leu Gly Ala Arg Ala Gln Gly Gly Thr
                 20                  25

CGT AGC CCC AGG TGT GAC TGT GCC GGT GAC TTC CAC AAG            211
Arg Ser Pro Arg Cys Asp Cys Ala Gly Asp Phe His Lys
         30                  35                  40

AAG ATT GGT CTG TTT TGT TGC AGA GGC TGC CCA GCG GGG            250
Lys Ile Gly Leu Phe Cys Cys Arg Gly Cys Pro Ala Gly
             45                  50

CAC TAC CTG AAG GCC CCT TGC ACG GAG CCC TGC GGC AAC            289
His Tyr Leu Lys Ala Pro Cys Thr Glu Pro Cys Gly Asn
 55                  60                  65

TCC ACC TGC CTT GTG TGT CCC CAA GAC ACC TTC TTG GCC            328
Ser Thr Cys Leu Val Cys Pro Gln Asp Thr Phe Leu Ala
             70                  75                  80

TGG GAG AAC CAC CAT AAT TCT GAA TGT GCC CGC TGC CAG            367
Trp Glu Asn His His Asn Ser Glu Cys Ala Arg Cys Gln
                 85                  90

GCC TGT GAT GAG CAG GCC TCC CAG GTG GCG CTG GAG AAC            406
Ala Cys Asp Glu Gln Ala Ser Gln Val Ala Leu Glu Asn
         95                 100                 105

TGT TCA GCA GTG GCC GAC ACC CGC TGT GGC TGT AAG CCA            445
Cys Ser Ala Val Ala Asp Thr Arg Cys Gly Cys Lys Pro
             110                 115

GGC TGG TTT GTG GAG TGC CAG GTC AGC CAA TGT GTC AGC            484
Gly Trp Phe Val Glu Cys Gln Val Ser Gln Cys Val Ser
120                 125                 130

AGT TCA CCC TTC TAC TGC CAA CCA TGC CTA GAC TGC GGG            523
Ser Ser Pro Phe Tyr Cys Gln Pro Cys Leu Asp Cys Gly
         135                 140                 145

GCC CTG CAC CGC CAC ACA CGG CTA CTC TGT TCC CGC AGA            562
Ala Leu His Arg His Thr Arg Leu Leu Cys Ser Arg Arg
                 150                 155

GAT ACT GAC TGT GGG ACC TGC CTG CCT GGC TTC TAT GAA            601
Asp Thr Asp Cys Gly Thr Cys Leu Pro Gly Phe Tyr Glu
         160                 165                 170

CAT GGC GAT GGC TGC GTG TCC TGC CCC ACG AGC ACC CTG            640
His Gly Asp Gly Cys Val Ser Cys Pro Thr Ser Thr Leu
             175                 180

GGG AGC TGT CCA GAG CGC TGT GCC GCT GTC TGT GGC TGG            679
Gly Ser Cys Pro Glu Arg Cys Ala Ala Val Cys Gly Trp
185                 190                 195

AGG CAG ATG TTC TGG GTC CAG GTG CTC CTG GCT GGC CTT            718
Arg Gln Met Phe Trp Val Gln Val Leu Leu Ala Gly Leu
     200                 205                 210

GTG GTC CCC CTC CTG CTT GGG GCC ACC CTG ACC TAC ACA            757
Val Val Pro Leu Leu Leu Gly Ala Thr Leu Thr Tyr Thr
                 215                 220

TAC CGC CAC TGC TGG CCT CAC AAG CCC CTG GTT ACT GCA            796
```

-continued

```
Tyr Arg His Cys Trp Pro His Lys Pro Leu Val Thr Ala
    225                 230                 235

GAT GAA GCT GGG ATG GAG GCT CTG ACC CCA CCA CCG GCC                   835
Asp Glu Ala Gly Met Glu Ala Leu Thr Pro Pro Pro Ala
            240                 245

ACC CAT CTG TCA CCC TTG GAC AGC GCC CAC ACC CTT CTA                   874
Thr His Leu Ser Pro Leu Asp Ser Ala His Thr Leu Leu
250                 255                 260

GCA CCT CCT GAC AGC AGT GAG AAG ATC TGC ACC GTC CAG                   913
Ala Pro Pro Asp Ser Ser Glu Lys Ile Cys Thr Val Gln
        265                 270                 275

TTG GTG GGT AAC AGC TGG ACC CCT GGC TAC CCC GAG ACC                   952
Leu Val Gly Asn Ser Trp Thr Pro Gly Tyr Pro Glu Thr
                280                 285

CAG GAG GCG CTC TGC CCG CAG GTG ACA TGG TCC TGG GAC                   991
Gln Glu Ala Leu Cys Pro Gln Val Thr Trp Ser Trp Asp
    290                 295                 300

CAG TTG CCC AGC AGA GCT CTT GGC CCC GCT GCT GCG CCC                  1030
Gln Leu Pro Ser Arg Ala Leu Gly Pro Ala Ala Ala Pro
                305                 310

ACA CTC TCG CCA GAG TCC CCA GCC GGC TCG CCA GCC ATG                  1069
Thr Leu Ser Pro Glu Ser Pro Ala Gly Ser Pro Ala Met
315                 320                 325

ATG CTG CAG CCG GGC CCG CAG CTC TAC GAC GTG ATG GAC                  1108
Met Leu Gln Pro Gly Pro Gln Leu Tyr Asp Val Met Asp
        330                 335                 340

GCG GTC CCA GCG CGG CGC TGG AAG GAG TTC GTG CGC ACG                  1147
Ala Val Pro Ala Arg Arg Trp Lys Glu Phe Val Arg Thr
                345                 350

CTG GGG CTG CGC GAG GCA GAG ATC GAA GCC GTG GAG GTG                  1186
Leu Gly Leu Arg Glu Ala Glu Ile Glu Ala Val Glu Val
    355                 360                 365

GAG ATC GGC CGC TTC CGA GAC CAG CAG TAC GAG ATG CTC                  1225
Glu Ile Gly Arg Phe Arg Asp Gln Gln Tyr Glu Met Leu
                370                 375

AAG CGC TGG CGC CAG CAG CAG CCC GCG GGC CTC GGA GCC                  1264
Lys Arg Trp Arg Gln Gln Gln Pro Ala Gly Leu Gly Ala
380                 385                 390

GTT TAC GCG GCC CTG GAG CGC ATG GGG CTG GAC GGC TGC                  1303
Val Tyr Ala Ala Leu Glu Arg Met Gly Leu Asp Gly Cys
        395                 400                 405

GTG GAA GAC TTG CGC AGC CGC CTG CAG CGC GGC CCG T                    1340
Val Glu Asp Leu Arg Ser Arg Leu Gln Arg Gly Pro
                410                 415     417

GACACGGCGC CCACTTGCCA CCTAGGCGCT CTGGTGGCCC TTGCAGAAGC                1390

CCTAAGTACG GTTACTTATG CGTGTAGACA TTTTATGTCA CTTATTAAGC                1440

CGCTGGCACG GCCCTGCGTA GCAGCACCAG CCGGCCCCAC CCCTGCTCGC                1490

CCCTATCGCT CCAGCCAAGG CGAAGAAGCA CGAACGAATG TCGAGAGGGG                1540

GTGAAGACAT TTCTCAACTT CTCGGCCGGA GTTTGGCTGA GATCGCGGTA                1590

TTAAATCTGT GAAAGAAAAC AAAAAAAAAA AAAAAAAAAA AAAA                     1634
```

(2) INFORMATION FOR SEQ ID NO:12:

(i) SEQUENCE CHARACTERISTICS:
        (A) LENGTH: 27 base pairs
        (B) TYPE: Nucleic Acid
        (C) STRANDEDNESS: Single
        (D) TOPOLOGY: Linear (xi) SEQUENCE DESCRIPTION: SEQ ID NO:12:

GGCGCTCTGG TGGCCCTTGC AGAAGCC                                    27

(2) INFORMATION FOR SEQ ID NO:13:

(i) SEQUENCE CHARACTERISTICS:
        (A) LENGTH: 25 base pairs
        (B) TYPE: Nucleic Acid
        (C) STRANDEDNESS: Single
        (D) TOPOLOGY: Linear (xi) SEQUENCE DESCRIPTION: SEQ ID NO:13:

TTCGGCCGAG AAGTTGAGAA ATGTC                                      25

(2) INFORMATION FOR SEQ ID NO:14:

(i) SEQUENCE CHARACTERISTICS:
        (A) LENGTH: 29 base pairs
        (B) TYPE: Nucleic Acid
        (C) STRANDEDNESS: Single
        (D) TOPOLOGY: Linear (xi) SEQUENCE DESCRIPTION: SEQ ID NO:14:

ATCAGGGACT TTCCGCTGGG GACTTTCCG                                  29

(2) INFORMATION FOR SEQ ID NO:15:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (xi) SEQUENCE DESCRIPTION: SEQ ID NO:15:

AGGATGGGAA GTGTGTGATA TATCCTTGAT                                 30

APO-3 POLYPEPTIDE

RELATED APPLICATIONS

This application is a non-provisional application claiming priority under 35 USC Section 119(e) to provisional application number 60/026,943 filed Sep. 23, 1996, the contents of which are incorporated herein by reference.

FIELD OF THE INVENTION

The present invention relates generally to the identification, isolation, and recombinant production of novel polypeptides, designated herein as "Apo-3".

BACKGROUND OF THE INVENTION

Control of cell numbers in mammals is believed to be determined, in part, by a balance between cell proliferation and cell death. One form of cell death, sometimes referred to as necrotic cell death, is typically characterized as a pathologic form of cell death resulting from some trauma or cellular injury. In contrast, there is another, "physiologic" form of cell death which usually proceeds in an orderly or controlled manner. This orderly or controlled form of cell death is often referred to as "apoptosis" [see, e.g., Barr et al., Bio/Technology, 12:487–493 (1994)]. Apoptotic cell death naturally occurs in many physiological processes, including embryonic development and clonal selection in the immune system [Itoh et al., Cell, 66:233–243 (1991)]. Decreased levels of apoptotic cell death have been associated with a variety of pathological conditions, including cancer, lupus, and herpes virus infection [Thompson, Science, 267:1456–1462 (1995)]. Increased levels of apoptotic cell death may be associated with a variety of other pathological conditions, including AIDS, Alzheimer's disease, Parkinson's disease, amyotrophic lateral sclerosis, multiple sclerosis, retinitis pigmentosa, cerebellar degeneration, aplastic anemia, myocardial infarction, stroke, reperfusion injury, and toxin-induced liver disease [see, Thompson, supra].

Apoptotic cell death is typically accompanied by one or more characteristic morphological and biochemical changes in cells, such as condensation of cytoplasm, loss of plasma membrane microvilli, segmentation of the nucleus, degradation of chromosomal DNA or loss of mitochondrial function. A variety of extrinsic and intrinsic signals are believed to trigger or induce such morphological and biochemical cellular changes [Raff, Nature, 356:397–400 (1992); Steller, Science, 267:1445–1449 (1995); Sachs et al., Blood, 82:15 (1993)]. For instance, they can be triggered by hormonal stimuli, such as glucocorticoid hormones for immature thymocytes, as well as withdrawal of certain growth factors [Watanabe-Fukunaga et al., Nature, 356:314–317 (1992)]. Also, some identified oncogenes such as myc, rel, and E1A, and tumor suppressors, like p53, have been reported to have a role in inducing apoptosis. Certain chemotherapy drugs and some forms of radiation have likewise been observed to have apoptosis-inducing activity [Thompson, supra].

Various molecules, such as tumor necrosis factor-α ("TNF-α"), tumor necrosis factor-β ("TNF-β" or "lymphotoxin"), CD30 ligand, CD27 ligand, CD40 ligand, OX-40 ligand, 4-1BB ligand, Apo-1 ligand (also referred to as Fas ligand or CD95 ligand), TRAIL, and Apo-2 ligand have been identified as members of the tumor necrosis factor ("TNF") family of cytokines [See, e.g., Gruss and Dower, Blood, 85:3378–3404 (1995); Wiley et al., Immunity, 3:673–682 (1995); Pitti et al., J. Biol. Chem., 271:12687–12690 (1996)]. Among these molecules, TNF-α, TNF-β, CD30 ligand, 4-1BB ligand, Apo-1 ligand, TRAIL, and Apo-2 ligand have been reported to be involved in apoptotic cell death. Both TNF-α and TNF-β have been reported to induce apoptotic death in susceptible tumor cells [Schmid et al., Proc. Natl. Acad. Sci., 83:1881 (1986); Dealtry et al., Eur. J. Immunol., 17:689 (1987)]. Zheng et al. have reported that TNF-α is involved in post-stimulation apoptosis of CD8-positive T cells [Zheng et al., Nature, 377:348–351 (1995)]. Other investigators have reported that CD30 ligand may be involved in deletion of self-reactive T cells in the thymus [Amakawa et al., Cold Spring Harbor Laboratory Symposium on Programmed Cell Death, Abstr. No. 10, (1995)].

Mutations in the mouse Fas/Apo-1 receptor or ligand genes (called lpr and gld, respectively) have been associated with some autoimmune disorders, indicating that Apo-1 ligand may play a role in regulating the clonal deletion of self-reactive lymphocytes in the periphery [Krammer et al., Curr. Op. Immunol., 6:279–289 (1994); Nagata et al., Science, 267:1449–1456 (1995)]. Apo-1 ligand is also reported to induce post-stimulation apoptosis in CD4-positive T lymphocytes and in B lymphocytes, and may be involved in the elimination of activated lymphocytes when their function is no longer needed [Krammer et al., supra; Nagata et al., supra]. Agonist mouse monoclonal antibodies specifically binding to the Apo-1 receptor have been reported to exhibit cell killing activity that is comparable to or similar to that of TNF-α [Yonehara et al., J. Exp. Med., 169:1747–1756 (1989)].

Induction of various cellular responses mediated by such TNF family cytokines is believed to be initiated by their binding to specific cell receptors. Two distinct TNF receptors of approximately 55-kDa (TNFR1) and 75-kDa (TNFR2) have been identified [Hohman et al., J. Biol. Chem., 264:14927–14934 (1989); Brockhaus et al., Proc. Natl. Acad. Sci., 87:3127–3131 (1990); EP 417,563, published Mar. 20, 1991] and human and mouse cDNAs corresponding to both receptor types have been isolated and characterized [Loetscher et al., Cell, 61:351 (1990); Schall et al., Cell, 61:361 (1990); Smith et al., Science, 248:1019–1023 (1990); Lewis et al., Proc. Natl. Acad. Sci., 88:2830–2834 (1991); Goodwin et al., Mol. Cell. Biol., 11:3020–3026 (1991)]. Extensive polymorphisms have been associated with both TNF receptor genes [see, e.g., Takao et al., Immunogenetics, 37:199–203 (1993)]. Both TNFRs share the typical structure of cell surface receptors including extracellular, transmembrane and intracellular regions. The extracellular portions of both receptors are found naturally also as soluble TNF-binding proteins [Nophar, Y. et al., EMBO J., 9:3269 (1990); and Kohno, T. et al., Proc. Natl. Acad. Sci. U.S.A., 87:8331 (1990)]. More recently, the cloning of recombinant soluble TNF receptors was reported by Hale et al. [J. Cell. Biochem. Supplement 15F, 1991, p. 113 (P424)].

The extracellular portion of type 1 and type 2 TNFRs (TNFR1 and TNFR2) contains a repetitive amino acid sequence pattern of four cysteine-rich domains (CRDs) designated 1 through 4, starting from the NH$_2$-terminus. Each CRD is about 40 amino acids long and contains 4 to 6 cysteine residues at positions which are well conserved [Schall et al., supra; Loetscher et al., supra; Smith et al., supra; Nophar et al., supra; Kohno et al., supra] In TNFR1, the approximate boundaries of the four CRDs are as follows: CRD1—amino acids 14 to about 53; CRD2—amino acids from about 54 to about 97; CRD3—amino acids from about 98 to about 138; CRD4—amino acids from about 139 to about 167. In TNFR2, CRD1 includes amino acids 17 to about 54; CRD2—amino acids from about 55 to about 97; CRD3—amino acids from about 98 to about 140; and CRD4—amino acids from about 141 to about 179 [Banner et al., *Cell*, 73:431–435 (1993)]. The potential role of the CRDs in ligand binding is also described by Banner et al., supra.

A similar repetitive pattern of CRDs exists in several other cell-surface proteins, including the p75 nerve growth factor receptor (NGFR) [Johnson et al., *Cell*, 47:545 (1986); Radeke et al., *Nature*, 325:593 (1987)], the B cell antigen CD40 [Stamenkovic et al., *EMBO J.*, 8:1403 (1989)], the T cell antigen OX40 [Mallet et al., *EMBO J.*, 9:1063 (1990)] and the Fas antigen [Yonehara et al., supra and Itoh et al., supra]. CRDs are also found in the soluble TNFR (sTNFR)-like T2 proteins of the Shope and myxoma poxviruses [Upton et al., *Virology*, 160:20–29 (1987); Smith et al., *Biochem. Biophys. Res. Commun.*, 176:335 (1991); Upton et al., *Virology*, 184:370 (1991)]. Optimal alignment of these sequences indicates that the positions of the cysteine residues are well conserved. These receptors are sometimes collectively referred to as members of the TNF/NGF receptor superfamily. Recent studies on p75NGFR showed that the deletion of CRD1 [Welcher, A. A. et al., *Proc. Natl. Acad. Sci. USA*, 88:159–163 (1991)] or a 5-amino acid insertion in this domain [Yan, H. and Chao, M. V., *J. Biol. Chem.*, 266:12099–12104 (1991)] had little or no effect on NGF binding [Yan, H. and Chao, M. V., supra]. p75 NGFR contains a proline-rich stretch of about 60 amino acids, between its CRD4 and transmembrane region, which is not involved in NGF binding [Peetre, C. et al., *Eur. J. Hematol.*, 41:414–419 (1988); Seckinger, P. et al., *J. Biol. Chem.*, 264:11966–11973 (1989); Yan, H. and Chao, M. V., supra]. A similar proline-rich region is found in TNFR2 but not in TNFR1.

Itoh et al. disclose that the Apo-1 receptor can signal an apoptotic cell death similar to that signaled by the 55-kDa TNFR1 [Itoh et al., supra]. Expression of the Apo-1 antigen has also been reported to be down-regulated along with that of TNFR1 when cells are treated with either TNF-α or anti-Apo-1 mouse monoclonal antibody [Krammer et al., supra; Nagata et al., supra]. Accordingly, some investigators have hypothesized that cell lines that co-express both Apo-1 and TNFR1 receptors may mediate cell killing through common signaling pathways [Id.].

The TNF family ligands identified to date, with the exception of lymphotoxin-α, are type II transmembrane proteins, whose C-terminus is extracellular. In contrast, the receptors in the TNF receptor (TNFR) family identified to date are type I transmembrane proteins. In both the TNF ligand and receptor families, however, homology identified between family members has been found mainly in the extracellular domain ("ECD"). Several of the TNF family cytokines, including TNF-α, Apo-1 ligand and CD40 ligand, are cleaved proteolytically at the cell surface; the resulting protein in each case typically forms a homotrimeric molecule that functions as a soluble cytokine. TNF receptor family proteins are also usually cleaved proteolytically to release soluble receptor ECDs that can function as inhibitors of the cognate cytokines.

Two of the TNFR family members, TNFR1 and Fas/Apo1 (CD95), can activate apoptotic cell death [Chinnaiyan and Dixit, *Current Biology*, 6:555–562 (1996); Fraser and Evan, *Cell*; 85:781–784 (1996)]. TNFR1 is also known to mediate activation of the transcription factor, NF-κB [Tartaglia et al., *Cell*, 74:845–853 (1993); Hsu et al., *Cell*, 84:299–308 (1996)]. In addition to some ECD homology, these two receptors share homology in their intracellular domain (ICD) in an oligomerization interface known as the death domain [Tartaglia et al., supra]. Death domains are also found in several metazoan proteins that regulate apoptosis, namely, the Drosophila protein, Reaper, and the mammalian proteins referred to as FADD/MORT1, TRADD, and RIP [Cleaveland and Ihle, *Cell*, 81:479–482 (1995)]. Using the yeast-two hybrid system, Raven et al. report the identification of protein, wsl-1, which binds to the TNFR1 death domain [Raven et al., Programmed Cell Death Meeting, Sep. 20–24, 1995, Abstract at page 127; Raven et al., *European Cytokine Network*, 7:Abstr. 82 at page 210 (April–June 1996)]. The wsl-1 protein is described as being homologous to TNFR1 (48% identity) and having a restricted tissue distribution. According to Raven et al., the tissue distribution of wsl-1 is significantly different from the TNFR1 binding protein, TRADD.

Upon ligand binding and receptor clustering, TNFR1 and CD95 are believed to recruit FADD into a death-inducing signalling complex. CD95 purportedly binds FADD directly, while TNFR1 binds FADD indirectly via TRADD [Chinnaiyan et al., *Cell*, 81:505–512 (1995); Boldin et al., *J. Biol. Chem.*, 270:387–391 (1995); Hsu et al., supra; Chinnaiyan et al., *J. Biol. Chem.*, 271:4961–4965 (1996)]. It has been reported that FADD serves as an adaptor protein which recruits the thiol protease MACHα/FLICE into the death signalling complex [Boldin et al., *Cell*, 85:803–815 (1996); Muzio et al., *Cell*, 85:817–827 (1996)]. MACHα/FLICE appears to be the trigger that sets off a cascade of apoptotic proteases, including the interleukin-1β converting enzyme (ICE) and CPP32/Yama, which may execute some critical aspects of the cell death programme [Fraser and Evan, supra].

It was recently disclosed that programmed cell death involves the activity of members of a family of cysteine proteases related to the *C. elegans* cell death gene, ced-3, and to the mammalian IL-1-converting enzyme, ICE [Martin, cite (1995)]. The activity of the ICE and CPP32/Yama proteases can be inhibited by the product of the cowpox virus gene, crmA [Ray et al., *Cell*, 69:597–604 (1992); Tewari et al., *Cell*, 81:801–809 (1995)]. Recent studies show that CrmA can inhibit TNFR1- and CD95-induced cell death [Enari et al., *Nature*, 375:78–81 (1995); Tewari et al., *J. Biol. Chem.*, 270:3255–3260 (1995)].

For a review of the TNF family of cytokines and their receptors, see Gruss and Dower, supra.

SUMMARY OF THE INVENTION

Applicants have identified cDNA clones that encode novel polypeptides, designated in the present application as "Apo-3." The Apo-3 polypeptide has surprisingly been found to stimulate or induce apoptotic activity in mammalian cells. It is believed that Apo-3 is a member of the TNFR family; full-length native sequence human Apo-3 polypeptide exhibits some similarities to some known TNFRs, including TNFR1 and CD95. In particular, full-length native sequence human Apo-3 exhibits similarity to the TNFR family in its extracellular cysteine-rich repeats and resembles TNFR1 and CD95 in that it contains a cytoplasmic death domain sequence.

In one embodiment, the invention provides isolated Apo-3 polypeptide. In particular, the invention provides isolated native sequence Apo-3 polypeptide, which in one embodiment, includes an amino acid sequence comprising residues 1 to 417 of FIG. 8 (SEQ ID NO:10). In other embodiments, the isolated Apo-3 polypeptide comprises at least about 80% identity with native sequence Apo-3 polypeptide comprising residues 1 to 417 of FIG. 8 (SEQ ID NO:10).

In another embodiment, the invention provides an isolated extracellular domain sequence found in native sequence Apo-3 polypeptide. The isolated extracellular domain sequence preferably comprises residues 1 to 198 of FIG. 8 (SEQ ID NO:10).

In another embodiment, the invention provides an isolated death domain sequence found in native sequence Apo-3 polypeptide. The isolated death domain sequence preferably comprises residues 338 to 417 of FIG. 8 (SEQ ID NO:10).

In another embodiment, the invention provides chimeric molecules comprising Apo-3 polypeptide fused to a heterologous polypeptide or amino acid sequence. An example of such a chimeric molecule comprises an Apo-3 fused to an immunoglobulin sequence. Another example comprises an extracellular domain sequence of Apo-3 fused to a heterologous polypeptide or amino acid sequence, such as an immunoglobulin sequence.

In another embodiment, the invention provides an isolated nucleic acid molecule encoding Apo-3 polypeptide. In one aspect, the nucleic acid molecule is RNA or DNA that encodes an Apo-3 polypeptide or a particular domain of Apo-3, or is complementary to such encoding nucleic acid sequence, and remains stably bound to it under stringent conditions. In one embodiment, the nucleic acid sequence is selected from:

(a) the coding region of the nucleic acid sequence of FIG. 8 (SEQ ID NO:11) that codes for residue 1 to residue 417 (i.e., nucleotides 89–91 through 1337–1339), inclusive; or (b) the coding region of the nucleic acid sequence of FIG. 8 (SEQ ID NO:11) that codes for residue 1 to residue 198 (i.e., nucleotides 89–91 through 680–682), inclusive;

(c) the coding region of the nucleic acid sequence of FIG. 8 (SEQ ID NO:11) that codes for residue 338 to residue 417 (i.e., nucleotides 1100–1102 through 1337–1339), inclusive; or (d) a sequence corresponding to the sequence of (a), (b) or (c) within the scope of degeneracy of the genetic code.

In a further embodiment, the invention provides a vector comprising the nucleic acid molecule encoding the Apo-3 polypeptide or particular domain of Apo-3. A host cell comprising the vector or the nucleic acid molecule is also provided. A method of producing Apo-3 is further provided.

In another embodiment, the invention provides an antibody which specifically binds to Apo-3. The antibody may be an agonistic, antagonistic or neutralizing antibody.

In another embodiment, the invention provides non-human, transgenic or knock-out animals.

A further embodiment of the invention provides articles of manufacture and kits that include Apo-3 or Apo-3 antibodies.

Another embodiment of the invention provides a novel polypeptide, designated "Apo-2 ligand inhibitor." In one embodiment, the polypeptide sequence comprises amino acid residues 1 to 181 of FIG. 1 (SEQ ID NO:1).

BRIEF DESCRIPTION OF THE DRAWINGS

FIG. 1 shows the nucleotide sequence of human Apo-2 ligand inhibitor cDNA and its derived amino acid sequence.

FIG. 2 (shown as FIGS. 2A–2B) shows an alignment of the amino acid sequence encoded by clone 18.1 of Apo-2 ligand inhibitor with extracellular regions of other members of the human TNF receptor family.

FIG. 4 shows the nucleotide sequence of human Apo-2 ligand cDNA and its derived amino acid sequence.

FIGS. 6A–6E show the induction of apoptosis in B and T lymphocyte cell lines by Apo-2 ligand. Apoptotic cells were identified by characteristic morphological changes (A); by positive fluorescence staining with propidium iodide ("PI") and FITC-conjugated annexin V, measured by flow cytometry (B–D); and by analysis of internucleosomal DNA fragmentation (E).

FIG. 8 (shown as FIGS. 8A–8C) shows the nucleotide sequence of native sequence human Apo-3 cDNA and its derived amino acid sequence. The putative signal sequence and transmembrane domain are underlined, the death domain sequence is boxed, and the potential N-linked glycosylation sites are marked with an asterisk. Also boxed is the alanine residue which was present in the fetal lung but not in the fetal heart cDNA clone (discussed in Example 9 below).

FIG. 9 shows an alignment and comparison of the ECD sequences of native sequence human Apo-3, TNFR1 and CD95.

FIG. 10 shows an alignment and comparison of the death domain sequences of native sequence human Apo-3, TNFR1, CD95, FADD, TRADD, RIP and Drosophila Reaper.

DETAILED DESCRIPTION OF THE PREFERRED EMBODIMENTS

I. Definitions

Figure 3:
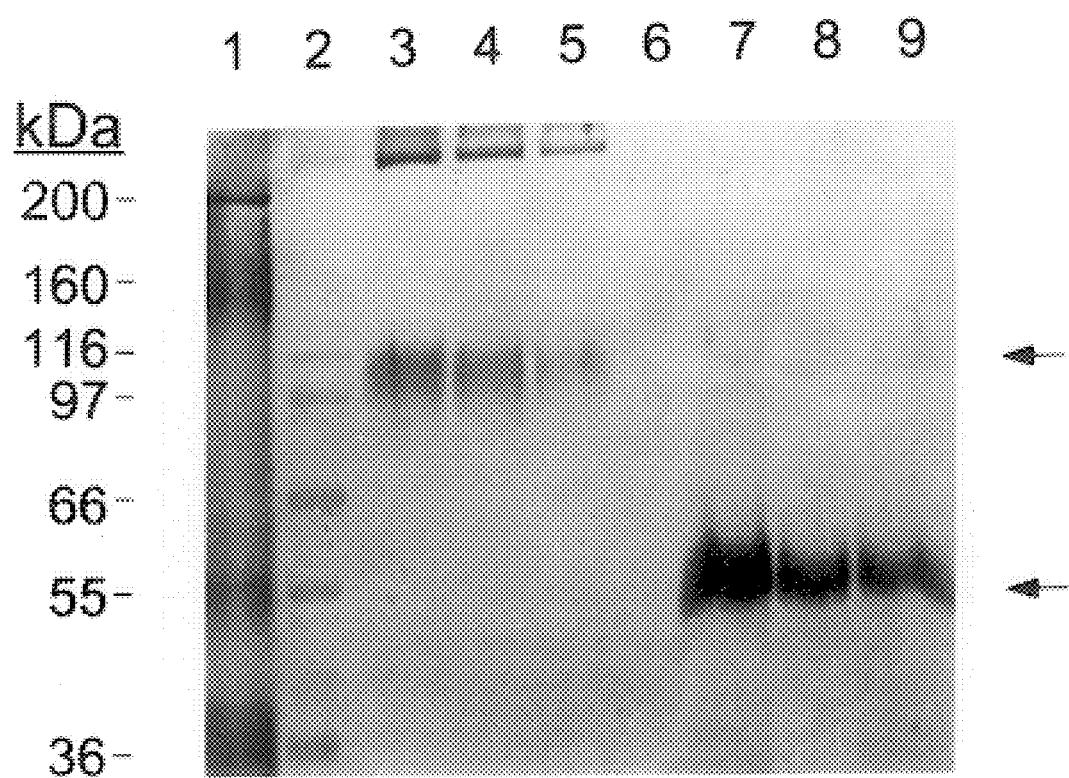
FIG. 3 shows a silver-stained gel of a protein A purified Apo-2 ligand inhibitor immunoadhesin analyzed under non-reducing (lanes 3–5) or reducing (lanes 7–9) conditions.

The terms "Apo-3 polypeptide" and "Apo-3" when used herein encompass native sequence Apo-3 and Apo-3 variants (each of which is defined herein). These terms encompass Apo-3 from a variety of mammals, including humans. The Apo-3 may be isolated from a variety of sources, such as from human tissue types or from another source, or prepared by recombinant or synthetic methods.

A "native sequence Apo-3" comprises a polypeptide having the same amino acid sequence as an Apo-3 derived from nature. Thus, a native sequence Apo-3 can have the amino acid sequence of naturally-occurring Apo-3 from any mammal. Such native sequence Apo-3 can be isolated from nature or can be produced by recombinant or synthetic means. The term "native sequence Apo-3" specifically encompasses naturally-occurring truncated or secreted forms of the Apo-3 (e.g., an extracellular domain sequence), naturally-occurring variant forms (e.g., alternatively spliced forms) and naturally-occurring allelic variants of the Apo-3. A naturally-occurring variant form of the Apo-3 includes an Apo-3 having an amino acid deletion at residue 236 in the amino acid sequence shown in FIG. 8 (SEQ ID NO:10). In one embodiment of the invention, the native sequence Apo-3 is a mature or full-length native sequence Apo-3 comprising the amino acid sequence of SEQ ID NO:10. The present definition of native sequence Apo-3 excludes known EST sequences, such as GenBank W71984.

"Apo-3 variant" means a biologically active Apo-3 as defined below having less than 100% sequence identity with Apo-3 having the deduced amino acid sequence shown in FIG. 8 (SEQ ID NO:10) for a full-length native sequence human Apo-3. Such Apo-3 variants include, for instance, Apo-3 polypeptides wherein one or more amino acid residues are added at the N- or C-terminus of, or within, the sequence of SEQ ID NO:10; from about one to 24 amino acid residues are deleted (including a single amino acid deletion at residue 236 in the amino acid sequence shown in FIG. 8 (SEQ ID NO:10), or optionally substituted by one or more amino acid residues; and derivatives thereof, wherein an amino acid residue has been covalently modified so that the resulting product has a non-naturally occurring amino acid. Ordinarily, an Apo-3 variant will have at least about 80% sequence identity, more preferably at least about 90% sequence identity, and even more preferably at least about 95% sequence identity with the sequence of FIG. 8 (SEQ ID NO:10). The present definition of Apo-3 variant excludes known EST sequences, such as GenBank W71984.

The terms "Apo-2 ligand inhibitor" and "Apo-2LI" are used herein to refer to a polypeptide sequence which includes amino acid residues 34 to 71, inclusive, residues 1 to 71, inclusive, residues 72 to 115, inclusive, residues 116 to 163, inclusive, residues 164 to 181, inclusive, or residues 1 to 181, inclusive, of the amino acid sequence shown in FIG. 1, as well as deletional, insertional, or substitutional variants of the above sequences. In a preferred embodiment, the polypeptide sequence comprises residues 1 to 181 of FIG. 1 (SEQ ID NO:1). In another preferred embodiment, the variants have at least about 80% sequence identity, more preferably at least about 90% sequence identity, and even more preferably, at least about 95% sequence identity with any one of the above Apo-2LI sequences. Optionally, the Apo-2 ligand inhibitor includes one or more cysteine-rich domains, and preferably includes one or more cysteine-rich domains comprising amino acids 34 to 71, amino acids 72 to 115, amino acids 116 to 163, or amino acids 164 to 181 of FIG. 1. The definition encompasses Apo-2 ligand inhibitor isolated from an Apo-2 ligand inhibitor source, such as from human tissue types (including blood or urine) or from another source, or prepared by recombinant or synthetic methods. The present definition of Apo-2 ligand inhibitor excludes known EST sequences, such as GenBank H41522, H46424, H46211, H46374, H46662, H41851, H49675, H22502, H46378 and H19739.

The terms "Apo-2 ligand" and "Apo-2L" are used herein to refer to a polypeptide sequence which includes amino acid residues 114 to 281, inclusive, residues 41 to 281, inclusive, residues 15 to 281, inclusive, or residues 1 to 281, inclusive, of the amino acid sequence shown in FIG. 4, as well as deletional, insertional, or substitutional variants of the above sequences. In a preferred embodiment, the polypeptide sequence comprises residues 114 to 281 of FIG. 4. In another preferred embodiment, the variants have at least about 80% sequence identity, more preferably at least about 90% sequence identity, and even more preferably, at least about 95% sequence identity with any one of the above Apo-2L sequences. The definition encompasses Apo-2 ligand isolated from an Apo-2 ligand source, such as from human tissue types or from another source, or prepared by recombinant or synthetic methods. The present definition of Apo-2 ligand excludes known EST sequences, such as GenBank HHEA47M, T90422, R31020, H43566, H44565, H44567, H54628, H44772, H54629, T82085, and T10524.

The term "epitope tagged" when used herein refers to a chimeric polypeptide comprising Apo-3, or a portion thereof, fused to a "tag polypeptide". The tag polypeptide has enough residues to provide an epitope against which an antibody can be made, yet is short enough such that it does not interfere with activity of the Apo-3. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the Apo-3 natural environment will not be present. Ordinarily, however, isolated polypeptide will be prepared by at least one purification step.

An "isolated" Apo-3 nucleic acid molecule is a nucleic acid molecule that is identified and separated from at least one contaminant nucleic acid molecule with which it is ordinarily associated in the natural source of the Apo-3 nucleic acid. An isolated Apo-3 nucleic acid molecule is other than in the form or setting in which it is found in nature. Isolated Apo-3 nucleic acid molecules therefore are distinguished from the Apo-3 nucleic acid molecule as it exists in natural cells. However, an isolated Apo-3 nucleic acid molecule includes Apo-3 nucleic acid molecules contained in cells that ordinarily express Apo-3 where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-Apo-3 monoclonal antibodies (including agonist, antagonist, and neutralizing antibodies) and anti-Apo-3 antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-Apo-3 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. See, e.g. U.S. Pat. No. 4,816,567 and Mage et al., in *Monoclonal Antibody Production Techniques and Applications*, pp. 79–97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256:495 (1975), or may be made by recombinant DNA methods such as described in U.S. Pat. No. 4,816,567. The "monoclonal antibodies" may also be isolated from phage libraries generated using the techniques described in McCafferty et al., *Nature*, 348:552–554 (1990), for example.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

"Biologically active" and "desired biological activity" for the purposes herein mean having the ability to induce or stimulate apoptosis in at least one type of mammalian cell in vivo or ex vivo.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis or DNA electrophoresis, all of which are known in the art.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

II. Compositions and Methods of the Invention

The present invention provides newly identified and isolated Apo-3 polypeptides. In particular, Applicants have identified and isolated various human Apo-3 polypeptides. The properties and characteristics of some of these Apo-3 polypeptides are described in further detail in the Examples below. Based upon the properties and characteristics of the Apo-3 polypeptides disclosed herein, it is Applicants' present belief that Apo-3 is a member of the TNFR family.

Another novel polypeptide, the polypeptide identified herein as "Apo-2 ligand inhibitor," is also provided in the present application. The properties and characteristics of human Apo-2 ligand inhibitor are described in further detail in the Examples below. Although not being bound to any particular theory, it is presently believed that Apo-2LI comprising residues 1 to 181 of FIG. 1 (SEQ ID NO:1) may be a soluble, truncated or secreted form of Apo-3.

A description follows as to how Apo-3, as well as Apo-3 chimeric molecules and anti-Apo-3 antibodies, may be prepared. It is contemplated that the methods and materials described below (and in the Examples herein) may also be employed to prepare Apo-2LI, Apo-2LI chimeric molecules and anti-Apo-2LI antibodies.

A. Preparation of Apo-3

The description below relates primarily to production of Apo-3 by culturing cells transformed or transfected with a vector containing Apo-3 nucleic acid. It is of course, contemplated that alternative methods, which are well known in the art, may be employed to prepare Apo-3.

1. Isolation of DNA Encoding Apo-3

The DNA encoding Apo-3 may be obtained from any cDNA library prepared from tissue believed to possess the Apo-3 mRNA and to express it at a detectable level. Accordingly, human Apo-3 DNA can be conveniently obtained from a cDNA library prepared from human tissues, such as the bacteriophage libraries of human fetal heart and lung cDNA described in Example 9. The Apo-3-encoding gene may also be obtained from a genomic library or by oligonucleotide synthesis.

Libraries can be screened with probes (such as antibodies to the Apo-3 or oligonucleotides of at least about 20–80 bases) designed to identify the gene of interest or the protein encoded by it. Examples of oligonucleotide probes are provided in Example 9. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding Apo-3 is to use PCR methodology [Sambrook et al., supra; Dieffenbach et al., *PCR Primer: A Laboratory Manual* (Cold Spring Harbor Laboratory Press, 1995)].

A preferred method of screening employs selected oligonucleotide sequences to screen cDNA libraries from various human tissues. Example 9 below describes techniques for screening a cDNA library with different oligonucleotide probes. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling.

Nucleic acid having all the protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

Apo-3 variants can be prepared by introducing appropriate nucleotide changes into the Apo-3 DNA, or by synthesis of the desired Apo-3 polypeptide. Those skilled in the art will appreciate that amino acid changes may alter post-translational processes of the Apo-3, such as changing the number or position of glycosylation sites or altering the membrane anchoring characteristics.

Variations in the native sequence Apo-3 as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis. 2. Insertion of Nucleic Acid into A Replicable Vector The nucleic acid (e.g., cDNA or genomic DNA) encoding Apo-3 may be inserted into a replicable vector for further cloning (amplification of the DNA) or for expression. Various vectors are publicly available. The vector components generally include, but are not limited to, one or more of the following: a signal sequence, an origin of replication, one or more marker genes, an enhancer element, a promoter, and a transcription termination sequence, each of which is described below.

(i) Signal Sequence Component

The Apo-3 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the Apo-3 DNA that is inserted into the vector. The heterologous signal sequence selected preferably is one that is recognized and processed (i.e., cleaved by a signal peptidase) by the host cell. The signal sequence may be a prokaryotic signal sequence selected, for example, from the group of the alkaline phosphatase, penicillinase, 1pp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression the native Apo-3 presequence that normally directs insertion of Apo-3 in the cell membrane of human cells in vivo is satisfactory, although other mammalian signal sequences may be used to direct secretion of the protein, such as signal sequences from secreted polypeptides of the same or related species, as well as viral secretory leaders, for example, the herpes simplex glycoprotein D signal.

The DNA for such precursor region is preferably ligated in reading frame to DNA encoding Apo-3.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of Apo-3 DNA. However, the recovery of genomic DNA encoding Apo-3 is more complex than that of an exogenously replicated vector because restriction enzyme digestion is required to excise the Apo-3 DNA.

(iii) Selection Gene Component

Expression and cloning vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin [Southern et al., *J. Molec. Appl. Genet.*, 1:327 (1982)], mycophenolic acid (Mulligan et al., *Science*, 209:1422 (1980)] or hygromycin [Sugden et al., *Mol. Cell. Biol.*, 5:410–413 (1985)]. The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the Apo-3 nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes Apo-3. Amplification is the process by which genes in greater demand for the production of a protein critical for growth are reiterated in tandem within the chromosomes of successive generations of recombinant cells. Increased quantities of Apo-3 are synthesized from the amplified DNA. Other examples of amplifiable genes include metallothionein-I and -II, adenosine deaminase, and ornithine decarboxylase.

Cells transformed with the DHFR selection gene may first be identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA*, 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding Apo-3. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding Apo-3, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)]. The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts [Bianchi et al., *Curr. Genet.*, 12:185 (1987)]. More recently, an expression system for large-scale production of recombinant calf chymosin was reported for *K. lactis* [Van den Berg, Bio/Technology, 8:135 (1990)]. Stable multicopy expression vectors for secretion of mature recombinant human serum albumin by industrial strains of Kluyveromyces have also been disclosed [Fleer et al., *Bio/Technology*, 9:968–975 (1991)].

(iv) Promoter Component

Expression and cloning vectors usually contain a promoter that is recognized by the host organism and is operably linked to the Apo-3 nucleic acid sequence. Promoters are untranslated sequences located upstream (5') to the start codon of a structural gene (generally within about 100 to 1000 bp) that control the transcription and translation of particular nucleic acid sequence, such as the Apo-3 nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to Apo-3 encoding DNA by removing the promoter from the source DNA by restriction enzyme digestion and inserting the isolated promoter sequence into the vector. Both the native Apo-3 promoter sequence and many heterologous promoters may be used to direct amplification and/or expression of the Apo-3 DNA.

Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21–25 (1983)]. However, other known bacterial promoters are suitable. Their nucleotide sequences have been published, thereby enabling a skilled worker operably to ligate them to DNA encoding Apo-3 [Siebenlist et al., *Cell*, 20:269 (1980)] using linkers or adaptors to supply any required restriction sites. Promoters for use in bacterial systems also will contain a Shine-Dalgarno (S.D.) sequence operably linked to the DNA encoding Apo-3.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Apo-3 transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the Apo-3 sequence, provided such promoters are compatible with the host cell systems.

The early and late promoters of the SV40 virus are conveniently obtained as an SV40 restriction fragment that also contains the SV40 viral origin of replication [Fiers et al., *Nature*, 273:113 (1978); Mulligan and Berg, *Science*, 209:1422–1427 (1980); Pavlakis et al., *Proc. Natl. Acad. Sci. USA*, 78:7398–7402 (1981)]. The immediate early promoter of the human cytomegalovirus is conveniently obtained as a HindIII E restriction fragment [Greenaway et al., *Gene*, 18:355–360 (1982)]. A system for expressing DNA in mammalian hosts using the bovine papilloma virus as a vector is disclosed in U.S. Pat. No. 4,419,446. A modification of this system is described in U.S. Pat. No. 4,601,978 [See also Gray et al., *Nature*, 295:503–508 (1982) on expressing cDNA encoding immune interferon in monkey cells; Reyes et al., *Nature*, 297:598–601 (1982) on expression of human β-interferon cDNA in mouse cells under the control of a thymidine kinase promoter from herpes simplex virus; Canaani and Berg, *Proc. Natl. Acad. Sci. USA* 79:5166–5170 (1982) on expression of the human interferon β1 gene in cultured mouse and rabbit cells; and Gorman et al., *Proc. Natl. Acad. Sci. USA*, 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter].

(v) Enhancer Element Component

Transcription of a DNA encoding the Apo-3 of this invention by higher eukaryotes may be increased by inserting an enhancer sequence into the vector. Enhancers are cis-acting elements of DNA, usually about from 10 to 300 bp, that act on a promoter to increase its transcription. Enhancers are relatively orientation and position independent, having been found 5' [Laimins et al., *Proc. Natl. Acad. Sci. USA*, 78:993 (19811) and 3' [Lusky et al., *Mol. Cell Bio.*, 3:1108 (1983]) to the transcription unit, within an intron [Banerji et al., *Cell*, 33:729 (1983)], as well as within the coding sequence itself [Osborne et al., *Mol. Cell Bio.*, 4:1293 (1984)]. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297:17–18 (1982) on enhancing elements for activation of eukaryotic promoters. The enhancer may be spliced into the vector at a position 5' or 3' to the Apo-3 coding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Apo-3.

(vii) Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures can be used to transform E. coli K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9:309 (1981) or by the method of Maxam et al., *Methods in Enzymology*, 65:499 (1980).

(viii) Transient Expression Vectors

Expression vectors that provide for the transient expression in mammalian cells of DNA encoding Apo-3 may be employed. In general, transient expression involves the use of an expression vector that is able to replicate efficiently in a host cell, such that the host cell accumulates many copies of the expression vector and, in turn, synthesizes high levels of a desired polypeptide encoded by the expression vector [Sambrook et al., supra]. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying Apo-3 variants.

(ix) Suitable Exemplary Vertebrate Cell Vectors

Other methods, vectors, and host cells suitable for adaptation to the synthesis of Apo-3 in recombinant vertebrate cell culture are described in Gething et al., *Nature*, 293:620–625 (1981); Mantei et al., *Nature*, 281:40–46 (1979); EP 117,060; and EP 117,058.

3. Selection and Transformation of Host Cells

Suitable host cells for cloning or expressing the DNA in the vectors herein are the prokaryote, yeast, or higher eukaryote cells described above. Suitable prokaryotes for this purpose include but are not limited to eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. Preferably, the host cell should secrete minimal amounts of proteolytic enzymes.

In addition to prokaryotes, eukaryotic microbes such as filamentous fungi or yeast are suitable cloning or expression hosts for Apo-3-encoding vectors. *Saccharomyces cerevisiae*, or common baker's yeast, is the most commonly used among lower eukaryotic host microorganisms. However, a number of other genera, species, and strains are commonly available and useful herein.

Suitable host cells for the expression of glycosylated Apo-3 are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified [See, e.g., Luckow et al., *Bio/Technology*, 6:47–55 (1988); Miller et al., in *Genetic Engineering, Setlow et al., eds., Vol. 8* (Plenum Publishing, 1986), pp. 277–279; and Maeda et al., *Nature*, 315:592–594 (1985)]. A variety of viral strains for transfection are publicly available, e.g., the L-1 variant of *Autographa californica* NPV and the Bm-5 strain of *Bombyx mori* NPV.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*. During incubation of the plant cell culture with *A. tumefaciens*, the DNA encoding the Apo-3 can be transferred to the plant cell host such that it is transfected, and will, under appropriate conditions, express the Apo-3-encoding DNA. In addition, regulatory and signal sequences compatible with plant cells are available, such as the nopaline synthase promoter and polyadenylation signal sequences [Depicker et al., *J. Mol. Appl. Gen.*, 1:561 (1982)]. In addition, DNA segments isolated from the upstream region of the T-DNA 780 gene are capable of activating or increasing transcription levels of plant-expressible genes in recombinant DNA-containing plant tissue [EP 321,196 published Jun. 21, 1989].

Propagation of vertebrate cells in culture (tissue culture) is also well known in the art [See, e.g., *Tissue Culture*, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44–68 (1982)); MRC 5 cells; and FS4 cells.

Host cells are transfected and preferably transformed with the above-described expression or cloning vectors for Apo-3 production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. In addition, plants may be transfected using ultrasound treatment as described in WO 91/00358 published January 10, 1991.

For mammalian cells without such cell walls, the calcium phosphate precipitation method of Graham and van der Eb,

*Virology*, 52:456–457 (1978) is preferred. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

4. Culturing the Host Cells

Prokaryotic cells used to produce Apo-3 may be cultured in suitable media as described generally in Sambrook et al., supra.

The mammalian host cells used to produce Apo-3 may be cultured in a variety of media. Examples of commercially available media include Ham's F10 (Sigma), Minimal Essential Medium ("MEM", Sigma), RPMI-1640 (Sigma), and Dulbecco's Modified Eagle's Medium ("DMEM", Sigma). Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are within a host animal.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Various labels may be employed, most commonly radioisotopes, and particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorescers or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, or luminescent labels.

Antibodies useful for immunohistochemical staining and/or assay of sample fluids may be either monoclonal or polyclonal, and may be prepared in any mammal. Conveniently, the antibodies may be prepared against a native sequence Apo-3 polypeptide or against a synthetic peptide based on the DNA sequences provided herein or against exogenous sequence fused to Apo-3 DNA and encoding a specific antibody epitope.

6. Purification of Apo-3 Polypeptide

Forms of Apo-3 may be recovered from culture medium or from host cell lysates. If the Apo-3 is membrane-bound, it can be released from the membrane using a suitable detergent solution (e.g. Triton-X 100) or its extracellular region may be released by enzymatic cleavage.

When Apo-3 is produced in a recombinant cell other than one of human origin, the Apo-3 is free of proteins or polypeptides of human origin. However, it may be desired to purify Apo-3 from recombinant cell proteins or polypeptides to obtain preparations that are substantially homogeneous as to Apo-3. As a first step, the culture medium or lysate may be centrifuged to remove particulate cell debris. Apo-3 thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG.

Apo-3 variants in which residues have been deleted, inserted, or substituted can be recovered in the same fashion as native sequence Apo-3, taking account of any substantial changes in properties occasioned by the variation. For example, preparation of an Apo-3 fusion with another protein or polypeptide, e.g., a bacterial or viral antigen, immunoglobulin sequence, or receptor sequence, may facilitate purification; an immunoaffinity column containing antibody to the sequence can be used to adsorb the fusion polypeptide. Other types of affinity matrices also can be used.

A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native sequence Apo-3 may require modification to account for changes in the character of Apo-3 or its variants upon expression in recombinant cell culture.

7. Covalent Modifications of Apo-3 Polypeptides

Covalent modifications of Apo-3 are included within the scope of this invention. One type of covalent modification of the Apo-3 is introduced into the molecule by reacting targeted amino acid residues of the Apo-3 with an organic derivatizing agent that is capable of reacting with selected side chains or the N- or C-terminal residues of the Apo-3.

Derivatization with bifunctional agents is useful for crosslinking Apo-3 to a water-insoluble support matrix or surface for use in the method for purifying anti-Apo-3 antibodies, and vice-versa. Derivatization with one or more bifunctional agents will also be useful for crosslinking Apo-3 molecules to generate Apo-3 dimers. Such dimers may increase binding avidity and extend half-life of the molecule in vivo. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)-dithio] propioimidate yield photoactivatable intermediates that are capable of forming crosslinks in the presence of light.

Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group. The modified forms of the residues fall within the scope of the present invention.

Another type of covalent modification of the Apo-3 polypeptide included within the scope of this invention comprises altering the native glycosylation pattern of the polypeptide. "Altering the native glycosylation pattern" is intended for purposes herein to mean deleting one or more carbohydrate moieties found in native sequence Apo-3, and/or adding one or more glycosylation sites that are not present in the native sequence Apo-3.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxylamino acid, most commonly serine or threonine, although 5-hydroxyproline or 5-hydroxylysine may also be used.

Addition of glycosylation sites to the Apo-3 polypeptide may be accomplished by altering the amino acid sequence such that it contains one or more of the above-described tripeptide sequences (for N-linked glycosylation sites). The alteration may also be made by the addition of, or substitution by, one or more serine or threonine residues to the native sequence Apo-3 (for O-linked glycosylation sites). The Apo-3 amino acid sequence may optionally be altered through changes at the DNA level, particularly by mutating the DNA encoding the Apo-3 polypeptide at preselected bases such that codons are generated that will translate into the desired amino acids. The DNA mutation(s) may be made using methods described above and in U.S. Pat. No. 5,364,934, supra.

Another means of increasing the number of carbohydrate moieties on the Apo-3 polypeptide is by chemical or enzymatic coupling of glycosides to the polypeptide. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, *CRC Crit. Rev. Biochem.*, pp. 259–306 (1981).

Removal of carbohydrate moieties present on the Apo-3 polypeptide may be accomplished chemically or enzymatically or by mutational substitution of codons encoding for amino acid residues that serve as targets for glycosylation. For instance, chemical deglycosylation by exposing the polypeptide to the compound trifluoromethanesulfonic acid, or an equivalent compound can result in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Glycosylation at potential glycosylation sites may be prevented by the use of the compound tunicamycin as described by Duskin et al., *J. Biol. Chem.*, 257:3105 (1982). Tunicamycin blocks the formation of protein-N-glycoside linkages.

Another type of covalent modification of Apo-3 comprises linking the Apo-3 polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

8. Apo-3 Chimeras

The present invention also provides chimeric molecules comprising Apo-3 fused to another, heterologous polypeptide or amino acid sequence.

In one embodiment, the chimeric molecule comprises a fusion of the Apo-3 with a tag polypeptide which provides an epitope to which an anti-tag antibody can selectively bind. The epitope tag is generally placed at the amino- or carboxyl-terminus of the Apo-3. The presence of such epitope-tagged forms of the Apo-3 can be detected using an antibody against the tag polypeptide. Also, provision of the epitope tag enables the Apo-3 to be readily purified by affinity purification using an anti-tag antibody or another type of affinity matrix that binds to the epitope tag.

Various tag polypeptides and their respective antibodies are well known in the art. Examples include the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6) :547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)]. Once the tag polypeptide has been selected, an antibody thereto can be generated using the techniques disclosed herein.

Generally, epitope-tagged Apo-3 may be constructed and produced according to the methods described above. Apo-3-tag polypeptide fusions are preferably constructed by fusing the cDNA sequence encoding the Apo-3 portion in-frame to the tag polypeptide DNA sequence and expressing the resultant DNA fusion construct in appropriate host cells. Ordinarily, when preparing the Apo-3-tag polypeptide chimeras of the present invention, nucleic acid encoding the Apo-3 will be fused at. its 3' end to nucleic acid encoding the N-terminus of the tag polypeptide, however 5' fusions are also possible. For example, a polyhistidine sequence of about 5 to about 10 histidine residues may be fused at the N-terminus or the C-terminus and used as a purification handle in affinity chromatography.

Epitope-tagged Apo-3 can be purified by affinity chromatography using the anti-tag antibody. The matrix to which the affinity antibody is attached may include, for instance, agarose, controlled pore glass or poly(styrenedivinyl) benzene. The epitope-tagged Apo-3 can then be eluted from the affinity column using techniques known in the art.

In another embodiment, the chimeric molecule comprises an Apo-3 polypeptide fused to an immunoglobulin sequence. The chimeric molecule may also comprise a particular domain sequence of Apo-3, such as the extracellular domain sequence of native Apo-3 (see FIG. 8) fused to an immunoglobulin sequence. This includes chimeras in monomeric, homo- or heteromultimeric, and particularly homo- or heterodimeric, or -tetrameric forms; optionally, the chimeras may be in dimeric forms or homodimeric heavy chain forms. Generally, these assembled immunoglobulins will have known unit structures as represented by the following diagrams.

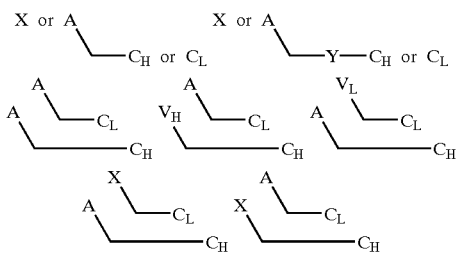

A basic four chain structural unit is the form in which IgG, IgD, and IgE exist. A four chain unit is repeated. in the higher molecular weight immunoglobulins; IgM generally exists as a pentamer of basic four-chain units held together by disulfide bonds. IgA globulin, and occasionally IgG globulin, may also exist in a multimeric form in serum. In the case of multimers, each four chain unit may be the same or different.

The following diagrams depict some exemplary monomer, homo- and heterodimer and homo- and heteromultimer structures. These diagrams are merely illustrative, and the chains of the multimers are believed to be disulfide bonded in the same fashion as native immunoglobulins.

monomer: 

homodimer: 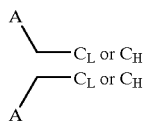

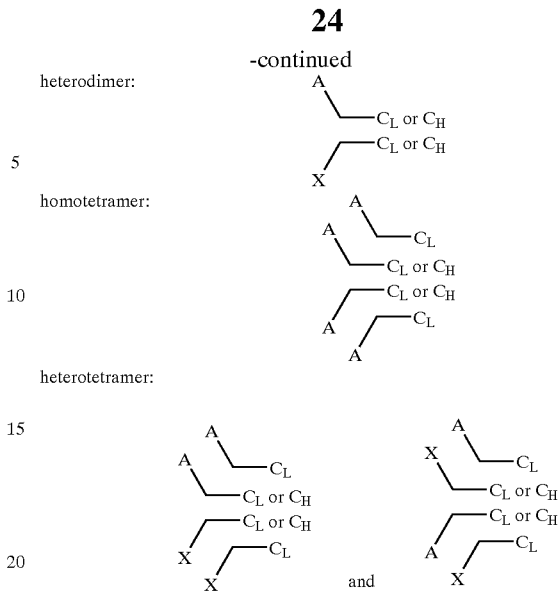

In the foregoing diagrams, "A" means an Apo-3 sequence or an Apo-3 sequence fused to a heterologous sequence; X is an additional agent, which may be the same as A or different, a portion of an immunoglobulin superfamily member such as a variable region or a variable region-like domain, including a native or chimeric immunoglobulin variable region, a toxin such a pseudomonas exotoxin or ricin, or a sequence functionally binding to another protein, such as other cytokines (i.e., IL-1, interferon-γ) or cell surface molecules (i.e., NGFR, CD40, OX40, Fas antigen, T2 proteins of Shope and myxoma poxviruses), or a polypeptide therapeutic agent not otherwise normally associated with a constant domain; Y is a linker or another receptor sequence; and $V_L$, $V_H$, $C_L$ and $C_H$ represent light or heavy chain variable or constant domains of an immunoglobulin. Structures comprising at least one CRD of an Apo-3 sequence as "A" and another cell-surface protein having a repetitive pattern of CRDs (such as TNFR) as "X" are specifically included.

It will be understood that the above diagrams are merely exemplary of the possible structures of the chimeras of the present invention, and do not encompass all possibilities. For example, there might desirably be several different "A's, "X's, or "Y"s in any of these constructs. Also, the heavy or light chain constant domains may be originated from the same or different immunoglobulins. All possible permutations of the illustrated and similar structures are all within the scope of the invention herein.

In general, the chimeric molecules can be constructed in a fashion similar to chimeric antibodies in which a variable domain from an antibody of one species is substituted for the variable domain of another species. See, for example, EP 0 125 023; EP 173,494; Munro, *Nature*, 312:597 (Dec. 13, 1984); Neuberger et al., *Nature*, 312:604–608 (Dec. 13, 1984); Sharon et al., *Nature*, 309:364–367 (May 24, 1984); Morrison et al., *Proc. Nat'l. Acad. Sci. USA*, 81:6851–6855 (1984); Morrison et al., *Science*, 229:1202–1207 (1985); Boulianne et al., *Nature*, 312:643–646 (Dec. 13, 1984); Capon et al., *Nature*, 337:525–531 (1989); Traunecker et al., *Nature*, 339:68–70 (1989).

Alternatively, the chimeric molecules may be constructed as follows. The DNA including a region encoding the desired sequence, such as an Apo-3 and/or TNFR sequence, is cleaved by a restriction enzyme at or proximal to the 3' end of the DNA encoding the immunoglobulin-like domain (s) and at a point at or near the DNA encoding the N-terminal end of the Apo-3 or TNFR polypeptide (where use of a different leader is contemplated) or at or proximal to the N-terminal coding region for TNFR (where the native signal is employed). This DNA fragment then is readily inserted proximal, to DNA encoding an immunoglobulin light or heavy chain constant region and, if necessary, the resulting construct tailored by deletional mutagenesis. Preferably, the Ig is a human immunoglobulin when the chimeric molecule is intended for in vivo therapy for humans. DNA encoding immunoglobulin light or heavy chain constant regions is known or readily available from cDNA libraries or is synthesized. See for example, Adams et al., *Biochemistry*, 19:2711–2719 (1980); Gough et al., *Biochemistry*, 19:2702–2710 (1980); Dolby et al., *Proc. Natl. Acad. Sci. . USA*, 77:6027–6031 (1980); Rice et al., *Proc. Natl. Acad. Sci.*, 79:7862–7865 (1982); Falkner et al., *Nature*, 298:286–288 (1982); and Morrison et al., *Ann. Rev. Immunol.*, 2:239–256 (1984).

Further details of how to prepare such fusions are found in publications concerning the preparation of immunoadhesins. Immunoadhesins in general, and CD4-Ig fusion molecules specifically are disclosed in WO 89/02922, published Apr. 6, 1989). Molecules comprising the extracellular portion of CD4, the receptor for human immunodeficiency virus (HIV), linked to IgG heavy chain constant region are known in the art and have been found to have a markedly longer half-life and lower clearance than the soluble extracellular portion of CD4 [Capon et al., supra; Byrn et al., *Nature*, 344:667 (1990)]. The construction of specific chimeric TNFR-IgG molecules is also described in Ashkenazi et al. *Proc. Natl. Acad. Sci.*, 88:10535–10539 (1991); Lesslauer et al. [*J. Cell. Biochem. Supplement* 15F, 1991, p. 115 (P 432)]; and Peppel and Beutler, *J. Cell. Biochem. Supplement* 15F, 1991, p. 118 (P 439)].

B. Therapeutic and Non-therapeutic Uses for Apo-3

Apo-3, as disclosed in the present specification, can be employed therapeutically to induce apoptosis in mammalian cells. This therapy can be accomplished for instance, using in vivo or ex vivo gene therapy techniques and includes the use of the death domain sequences disclosed herein. The Apo-3 chimeric molecules (including the chimeric molecules containing the extracellular domain sequence of Apo-3) comprising immunoglobulin sequences can also be employed therapeutically to inhibit apoptosis or NF-κB induction.

The Apo-3 of the invention also has utility in nontherapeutic applications. Nucleic acid sequences encoding the Apo-3 may be used as a diagnostic for tissue-specific typing. For example, procedures like in situ hybridization, Northern and Southern blotting, and PCR analysis may be used to determine whether DNA and/or RNA encoding Apo-3 is present in the cell type(s) being evaluated. Apo-3 nucleic acid will also be useful for the preparation of Apo-3 by the recombinant techniques described herein.

The isolated Apo-3 may be used in quantitative diagnostic assays as a control against which samples containing unknown quantities of Apo-3 may be prepared. Apo-3 preparations are also useful in generating antibodies, as standards in assays for Apo-3 (e.g., by labeling Apo-3 for use as a standard in a radioimmunoassay, radioreceptor assay, or enzyme-linked immunoassay), in affinity purification techniques, and in competitive-type receptor binding assays when labeled with, for instance, radioiodine, enzymes, or fluorophores.

Modified forms of the Apo-3, such as the Apo-3-IgG chimeric molecules (immunoadhesins) described above, can be used as immunogens in producing anti-Apo-3 antibodies.

Nucleic acids which encode Apo-3 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding Apo-3 or an appropriate sequence thereof can be used to clone genomic DNA encoding Apo-3 in accordance with established techniques and the genomic sequences used to generate transgenic animals that contain cells which express DNA encoding Apo-3. Methods for generating transgenic animals, particularly animals such as mice or rats, have become conventional in the art and are described, for example, in U.S. Pat. Nos. 4,736,866 and 4,870,009. Typically, particular cells would be targeted for Apo-3 transgene incorporation with tissue-specific enhancers. Transgenic animals that include a copy of a transgene encoding Apo-3 introduced into the germ line of the animal at an embryonic stage can be used to examine the effect of increased expression of DNA encoding Apo-3. Such animals can be used as tester animals for reagents thought to confer protection from, for example, pathological conditions associated with excessive apoptosis. In accordance with this facet of the invention, an animal is treated with the reagent and a reduced incidence of the pathological condition, compared to untreated animals bearing the transgene, would indicate a potential therapeutic intervention for the pathological condition. In another embodiment, transgenic animals that carry a soluble form of Apo-3 such as the Apo-3 ECD or an immunoglobulin chimera of such form could be constructed to test the effect of chronic neutralization of the ligand of Apo-3.

Alternatively, non-human homologues of Apo-3 can be used to construct a Apo-3 " knock out" animal which has a defective or altered gene encoding Apo-3 as a result of homologous recombination between the endogenous gene encoding Apo-3 and altered genomic DNA encoding Apo-3 introduced into an embryonic cell of the animal. For example, cDNA encoding Apo-3 can be used to clone genomic DNA encoding Apo-3 in accordance with established techniques. A portion of the genomic DNA encoding Apo-3 can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the Apo-3 polypeptide, including for example, development of tumors.

C. Anti-Apo-3 Antibody Preparation

The present invention further provides anti-Apo-3 antibodies. Antibodies against Apo-3 may be prepared as follows. Exemplary antibodies include polyclonal, monoclonal, humanized, bispecific, and heteroconjugate antibodies.

1. Polyclonal Antibodies

The Apo-3 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the Apo-3 polypeptide or a fusion protein thereof. An example of a suitable immunizing agent is a Apo-3-IgG fusion protein or chimeric molecule (including an Apo-3 ECD-IgG fusion protein). Cells expressing Apo-3 at their surface may also be employed. It may be useful to conjugate the immunizing agent to a protein known to be immunogenic in the mammal being immunized. Examples of such immunogenic proteins which may be employed include but are not limited to keyhole limpet hemocyanin, serum albumin, bovine thyroglobulin, and soybean trypsin inhibitor. An aggregating agent such as alum may also be employed to enhance the mammal's immune response. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for antibody titer. If desired, the mammal can be boosted until the antibody titer increases or plateaus.

2. Monoclonal Antibodies

The Apo-3 antibodies may, alternatively, be monoclonal antibodies. Monoclonal antibodies may be prepared using hybridoma methods, such as those described by Kohler and Milstein, supra. In a hybridoma method, a mouse, hamster, or other appropriate host animal, is typically immunized (such as described above) with an immunizing agent to elicit lymphocytes that produce or are capable of producing antibodies that will specifically bind to the immunizing agent. Alternatively, the lymphocytes may be immunized in vitro.

The immunizing agent will typically include the Apo-3 polypeptide or a fusion protein thereof. An example of a suitable immunizing agent is a Apo-3-IgG fusion protein or chimeric molecule. Cells expressing Apo-3 at their surface may also be employed. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassass Va. Human myeloma and mouse-human heteromyeloma cell lines also have been described for the production of human monoclonal antibodies [Kozbor, J. Immunol., 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against Apo-3. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an $F(ab')_2$ fragment that has two antigen combining sites and is still capable of cross-linking antigen.

The Fab fragments produced in the antibody digestion also contain the constant domains of the light chain and the first constant domain ($CH_1$) of the heavy chain. Fab' fragments differ from Fab fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

3. Humanized Antibodies

The Apo-3 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522–525 (1986); Reichmann et al., Nature, 332:323–329 (1988); and Presta, Curr. Op. Struct. Biol., 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522–525 (1986); Riechmann et al., Nature, 332:323–327 (1988); Verhoeyen et al., Science, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody [Sims et al., J. Immunol., 151:2296 (1993); Chothia and Lesk, J. Mol. Biol., 196:901 (1987)]. Another method uses a particular framework derived from the consensus sequence of all human antibodies of a particular subgroup of light or heavy chains. The same framework may be used for several different humanized antibodies [Carter et al., Proc. Natl. Acad. Sci. USA, 89:4285 (1992); Presta et al., J. Immunol., 151:2623 (1993)].

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding [see, WO 94/04679 published Mar. 3, 1994].

Transgenic animals (e.g., mice) that are capable, upon immunization, of producing. a full repertoire of human antibodies in the absence of endogenous immunoglobulin production can be employed. For example, it has been described that the homozygous deletion of the antibody heavy chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge [see, e.g., Jakobovits et al., Proc.

Natl. Acad. Sci. USA, 90:2551–255 (1993); Jakobovits et al., Nature, 362:255–258 (1993); Bruggermann et al., Year in Immuno., 7:33 (1993)]. Human antibodies can also be produced in phage display libraries [Hoogenboom and Winter, J. Mol. Biol., 227:381 (1991); Marks et al., J. Mol. Biol., 222:581 (1991)]. The techniques of Cote et al. and Boerner et al. are also available for the preparation of human monoclonal antibodies (Cote et al., Monoclonal Antibodies and Cancer Therapy, Alan R. Liss, p. 77 (1985) and Boerner et al., J. Immunol., 147(1):86–95 (1991)].

4. Bispecific Antibodies

Bispecific antibodies are monoclonal, preferably human or humanized, antibodies that have binding specificities for at least two different antigens. In the present case, one of the binding specificities is for the Apo-3, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Millstein and Cuello, Nature, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy-chain/light-chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., Methods in Enzymology, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

D. Therapeutic and Non-therapeutic Uses for Apo-3 Antibodies

The Apo-3 antibodies of the invention have therapeutic utility. Agonistic Apo-3 antibodies, for instance, may be employed to activate or stimulate apoptosis in cancer cells. Alternatively, antagonistic antibodies may be used to block excessive apoptosis (for instance in neurodegenerative disease) or to block potential autoimmune/inflammatory effects of Apo-3 resulting from NF-κB activation.

Apo-3 antibodies may further be used in diagnostic assays for Apo-3, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, Monoclonal Antibodies: A Manual of Techniques, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982).

Apo-3 antibodies also are useful for the affinity purification of Apo-3 from recombinant cell culture or natural sources. In this process, the antibodies against Apo-3 are immobilized on a suitable support, such a Sephadex resin or filter paper, using methods well known in the art. The immobilized antibody then is contacted with a sample containing the Apo-3 to be purified, and thereafter the support is washed with a suitable solvent that will remove substantially all the material in the sample except the Apo-3, which is bound to the immobilized antibody. Finally, the support is washed with another suitable solvent that will release the Apo-3 from the antibody.

E. Kits Containing Apo-3 or Apo-3 Antibodies

In a further embodiment of the invention, there are provided articles of manufacture and kits containing Apo-3 or Apo-3 antibodies which can be used, for instance, for the therapeutic or non-therapeutic applications described above. The article of manufacture comprises a container with a label. Suitable containers include, for example, bottles, vials, and test tubes. The containers may be formed from a variety of materials such as glass or plastic. The container holds a composition which includes an active agent that is effective for therapeutic or non-therapeutic applications, such as described above. The active agent in the composition is Apo-3 or an Apo-3 antibody. The label on the container indicates that the composition is used for a specific therapy or non-therapeutic application, and may also indicate directions for either in vivo or in vitro use, such as those described above.

The kit of the invention will typically comprise the container described above and one or more other containers comprising materials desirable from a commercial and user standpoint, including buffers, diluents, filters, needles, syringes, and package inserts with instructions for use.

The following examples are offered for illustrative purposes only, and are not intended to limit the scope of the present invention in any way.

All references cited in the present specification are hereby incorporated by reference in their entirety.

EXAMPLES

All restriction enzymes referred to in the examples were purchased from New England Biolabs and used according to manufacturer's instructions. All other commercially available reagents referred to in the examples were used according to manufacturer's instructions unless otherwise indicated. The source of those cells identified in the following examples, and throughout the specification, by ATCC accession numbers is the American Type Culture Collection, Manassass Va.

Example 1

Isolation of cDNA Clones Encoding Human Apo-2 Ligand Inhibitor

To isolate a cDNA for Apo-2 ligand inhibitor, a lambda gt10 bacteriophage library of human thymus cDNA (about $1 \times 10^6$ clones) (HL1074a, commercially available from Clontech) was screened by hybridization with synthetic oligonucleotide probes based on an EST sequence (GenBank locus H41522), which showed some degree of homology to human Fas/Apo-1. The EST sequence of H41522 is 433 bp and when translated in its +1 frame, shows 20 identities to a 78 amino acid region of human Fas/Apo-1. The sequence of H41522 is as follows:

CTGCTGGGGCCCGGGCCAGNGGCG-GCACTCGTAGCCCCAGGTGTGACTGTGC-CGGTGAC TTCCACAAGAAGATTGGTCT-GTTTTGTTGCAGAGGCTGCCCAGCGGGGCA ACTACCTGAA GGCCCCTTGCACGGAGCCCT-GCGCAACTCCACCTGCCTTGTGTGTC-CCCAAGACACCTTC TTGGCCTGGGAGAAC-CACCATAATTCTGAATGTGCCCGCTGCCAGG CCTGTG ATGAGCAG GCCTCCCAGGTGGCGCTG-GAGAACTGTTCAGCAGTGGCCGACAC-CCGCTGTGGCTGTAAG CAGGGCTGGTTTGTG-GAGTGCCAGGGTCAGCCAATGTGTCAGCAG TTTCAC CCTTCTAAT GCCAACCATGCCTAGACT-GCGGGGCCCTGCAACGCAACACACG-GCTAATNTGTTTCCCGC AGAGATNATTGTT (SEQ ID NO:2)

The oligonucleotide probes employed in the screening were 28 bp long, with the following respective sequences:

CCCGCTGCCAGGCCTGTGATGAGCAGGC (SEQ ID NO:3)

CAGGGCCCCGCAGTCTAGGCATGGTTGG (SEQ ID NO:4)

Hybridization was conducted with a 1:1 mixture of the two probes overnight at room temperature in buffer containing 20% formamide, 5×SSC, 10% dextran sulfate, 0.1 NaPiPO$_4$, 0.05M NaPO$_4$, 0.05 mg salmon sperm DNA, and 0.1% sodium dodecyl sulfate, followed consecutively by one wash at room temperature in 6×SSC, two washes at 37° C. in 1×SSC/0.1% SDS, two washes at 37° C. in 0.5×SSC/0.1% SDS, and two washes at 37° C. in 0.2×SSC/0.1% SDS. Four positive clones were identified in the cDNA library, and the positive clones were confirmed to be specific by PCR using the above hybridization probes as PCR primers. Single phage plaques containing each of the four positive clones were isolated by limiting dilution and the DNA was purified using a Wizard Lambda Prep DNA purification kit (commercially available from Promega).

The cDNA inserts from the four bacteriophage clones were excised from the vector arms by digestion with EcoRI, gel-purified, and subcloned into pRK7 [EP 278,776 published Aug. 17, 1988] that was predigested with EcoRI. Three of the clones (18.1, 24.1, and 28.1) contained an identical open reading frame; therefore further analysis was done with only one clone, 18.1. Clone 18.1 was approximately 1.4kb long.

The entire nucleotide sequence of Apo-2 ligand inhibitor is shown in FIG. 1 (SEQ ID NO:5). The cDNA contained one open reading frame with a translational initiation site assigned to the ATG codon at nucleotide positions 377–379. The surrounding sequence at this site is in reasonable agreement with the proposed consensus sequence for initiation sites [Kozak, *J. Cell. Biol.*, 115:887–903 (1991)]. The open reading frame ends at the termination codon TAA at nucleotide positions 919–921.

The predicted amino acid sequence of the Apo-2 ligand inhibitor encoded by clone 18.1 contains 181 amino acids, and has a calculated molecular weight of approximately 19.3 kDa and an isoelectric point of approximately 7.1. Hydropathy analysis indicated the presence of a hydrophobic signal sequence at the N-terminus of approximately 20 amino acids. Two potential N-linked glycosylation sites are located at residues 67 and 105 of the polypeptide precursor.

Figure 2A:
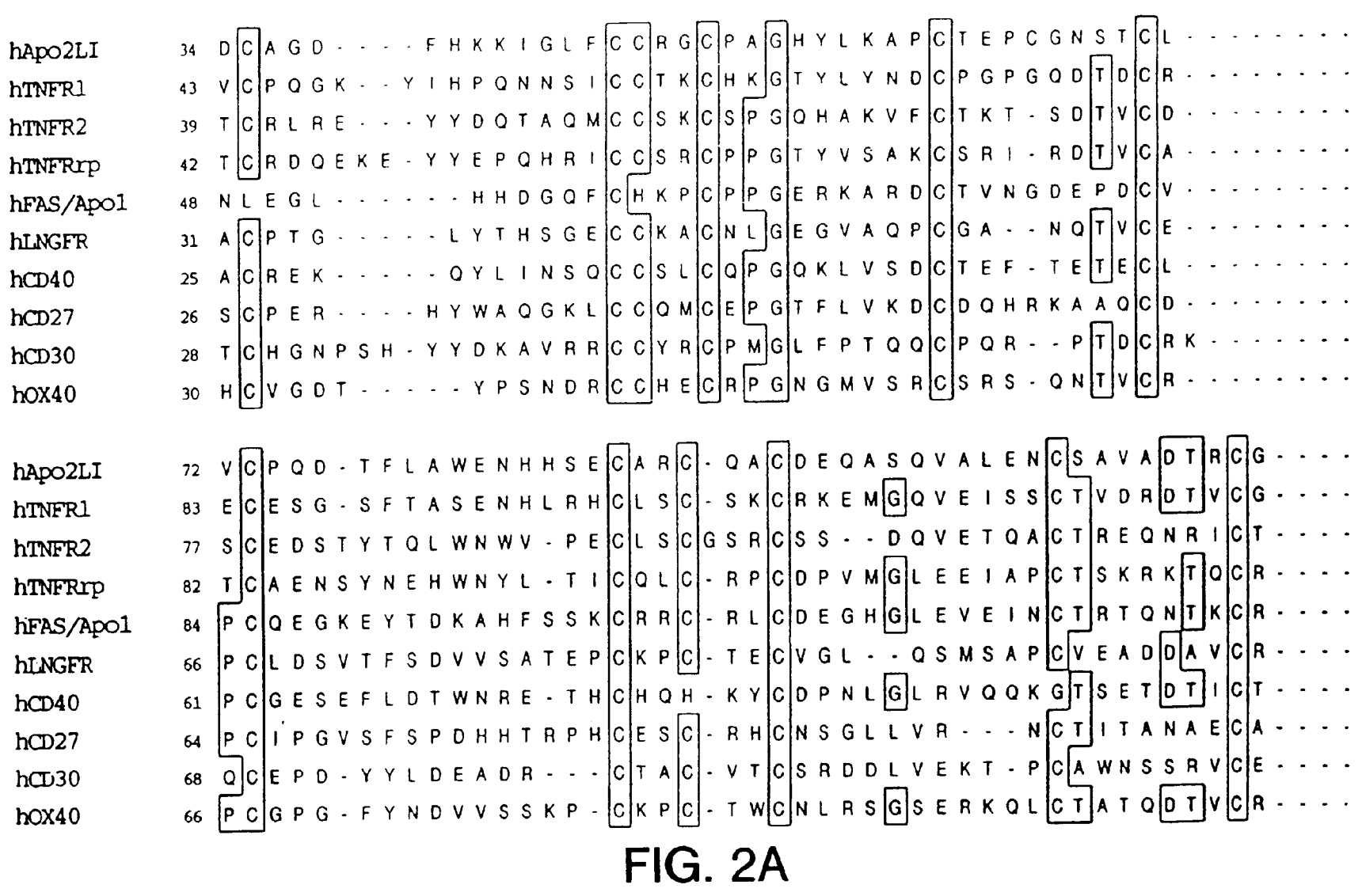
Figure 2B:
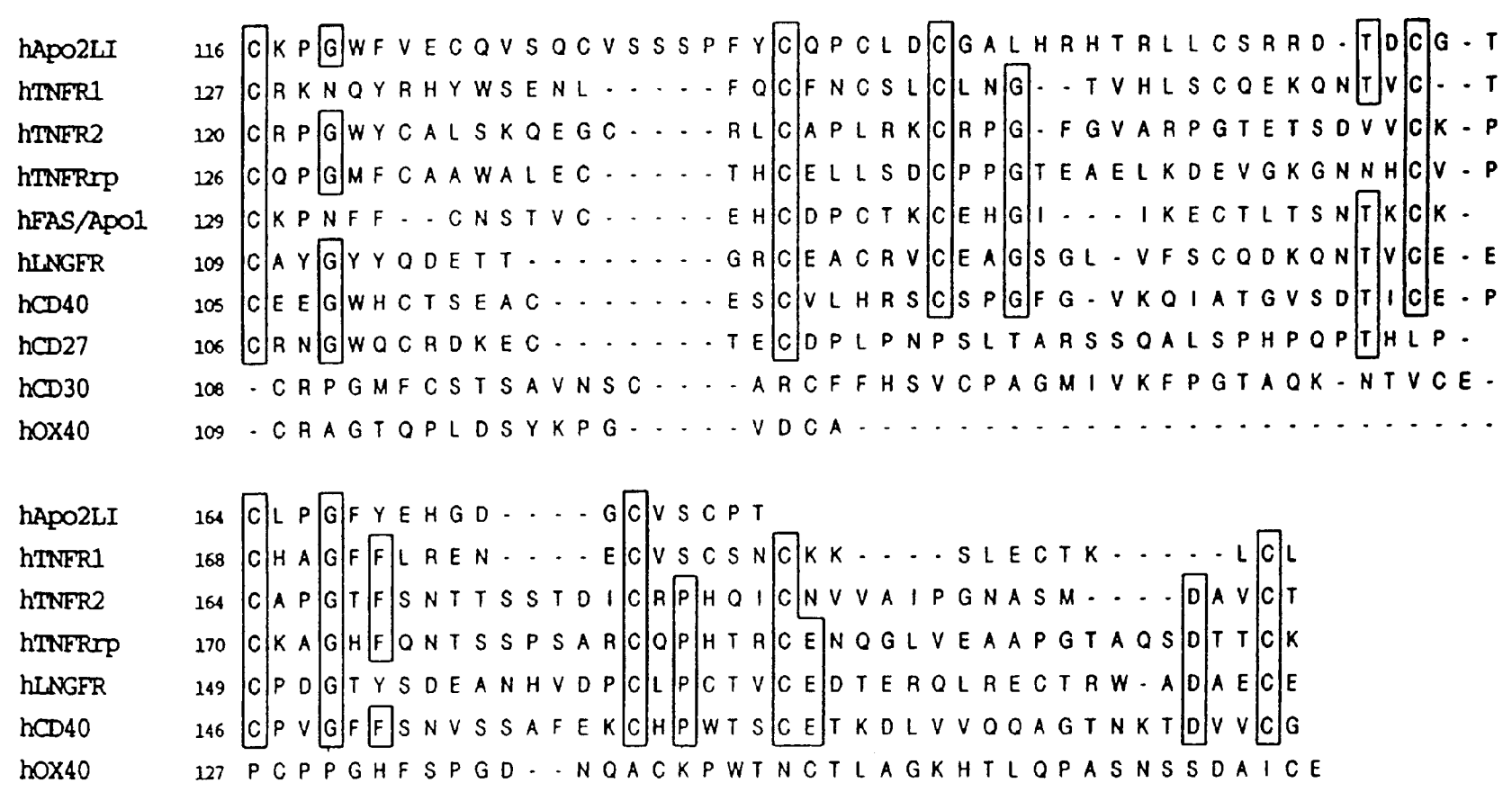

An alignment (using the Align™ computer program) of the amino acid sequence encoded by clone 18.1 with the extracellular regions of other known members of the human TNF receptor family showed the following percentages of identity: 30.2% identity to Fas/Apo-1; 28.7% to type 1 TNF receptor (TNFR1); 22.5% to the low affinity NGF receptor (LNGFR) and to CD40; 21.8% to CD30; 21.5% to CD27; 21.4% to OX40; 20.5% to type 2 TNF receptor (TNFR2) ; 20.1% to TNF receptor related protein (TNFRrp). (See also, FIG. 2)

TNF receptor family proteins are typically characterized by the presence of multiple (usually four) cysteine-rich domains in their extracellular regions—each cysteine-rich domain being approximately 45 amino acid long and contains approximately 6, regularly spaced, cysteine residues. Based on the crystal structure of the type 1 TNF receptor, the cysteines in each domain typically form three disulfide bonds in which usually cysteines 1 and 2, 3 and 5, and 4 and 6 are paired together. Applicants found that the polypeptide encoded by clone 18.1 contains three cysteine-rich domains and an apparently truncated fourth cysteine-rich domain that contains only three cysteines and stops 5 amino acids C-terminally to the third cysteine.

Amino acids 1 to 181 of the Apo-2LI clone 18.1 shown in FIG. 1 (SEQ ID NO:1) are identical to the amino acids 1 to 181 of the Apo-3 polypeptide, as described in Example 9 below, and shown in FIG. 8 (SEQ ID NO:10). Compared to Apo-3 polypeptide described in Example 9 below, the polypeptide encoded by clone 18.1 is truncated within the C-terminal region of the ECD and lacks some extracellular sequence as well as the transmembrane and cytoplasmic sequences of Apo-3. The truncation is believed to occur by alternative splicing of the mRNA which introduces a stop codon 5 amino acids downstream of the third cysteine of the fourth cysteine-rich domain. The 3' untranslated region is distinct from that of the Apo-3 clone FL8A.53 and contains a distinct polyadenylation site, suggesting that clone 18.1 represents a naturally-occurring mRNA.

Example 2

Expression of Apo-2 Ligand Inhibitor Clone 18.1

A pRK7 plasmid (described in Example 1) containing the Apo-2 ligand inhibitor cDNA (as described in Example 1) in the forward orientation, or a control pRK5 plasmid [Schall et al., Cell, 61:361–370 (1990); Suva, Science, 237:893–896 (1987)] containing the Apo-2 ligand inhibitor cDNA in the reverse orientation, were transfected transiently into human 293 cells (ATCC CRL 1573) by calcium phosphate precipitation. After 24 hours, the medium was replaced by serum free medium, and the cells were incubated for an additional 48 hours. The serum free conditioned media were then collected, cleared by centrifugation, and concentrated 5-fold by centrifugation in centricon tubes.

Example 3

Expression of Apo-2 Ligand Inhibitor Immunoadhesin

An immunoadhesin was constructed that consisted of the Apo-2 ligand inhibitor coding region (as described in Example 1), including its endogenous signal sequence, fused C-terminally to residues 183–211 of type 1 TNF receptor, which was fused in turn to the hinge and Fc regions of human IgG1 heavy chain, as described previously by Ashkenazi et al., supra.

The pRK5 plasmid encoding the chimeric Apo-2 ligand inhibitor immunoadhesin was transiently transfected into human 293 cells (described in Example 2) by calcium phosphate precipitation. After 24 hours, the medium was replaced by serum free medium, and the cells were incubated for an additional 6 days. The serum free conditioned media were then collected, cleared by centrifugation, and purified by protein A affinity chromatography, as described previously by Ashkenazi et al., supra. Gel electrophoresis showed that the purified protein exhibited a molecular weight of approximately 110 kDa under non-reducing conditions (FIG. 3, lanes 3–5) and approximately 55 kDa under reducing conditions (100 mM DTT, FIG. 3, lanes 7–9), thus indicating a disulfide-bonded homodimeric immunoadhesin structure. Higher molecular weight bands observed for non-reducing conditions are believed to be due to some aggregation of the immunoadhesin during sample preparation.

Example 4

Isolation of cDNA Clones Encoding Human Apo-2 Ligand

To isolate a full-length cDNA for Apo-2 ligand, a lambda gt11 bacteriophage library of human placental cDNA (about $1 \times 10^6$ clones) (HL10756, commercially available from Clontech) was screened by hybridization with synthetic oligonucleotide probes based on an EST sequence (GenBank locus HHEA47M), which showed some degree of homology to human Fas/Apo-1 ligand. The EST sequence of HHEA47M is 390 bp and when translated in its +3 frame, shows 16 identities to a 34 amino acid region of human Apo-1 ligand. The sequence of HHEA47M is as follows:

GGGACCCCAATGACGAAGAGAGTATGAA-CAGCCCCTGCTGGCAAGTCAAGTG-GCAACTCCGTCAG CTCGTTAGAAAGAT-GATTTTGAGAACCTCTGAGGAAACCATTTCT ACAGTTCAAGAAAAGCAACA AAATATTTCTC-CCCTAGTGAGAGAAAGAGGTCCTCA-GAGAGTAGCAGCTCACATAACTGGGACCA GAGGAAGAAGCAACACATTGTCTTCTC-CAAACTCCAAGAATGAAAAGG CTCTGGGCCGCAAAATA AACTCCTGGGAAT-CATCAAGGAGTGGGCATTCATTCCTGAG-CAACTTGCACTTGAGGAATGGTGA ACTGGT-CATCCATGAAAAGGGTTTTACTACATCTAT TCCCAAA
CATACTTTCGATTTCAGGAGG (SEQ ID NO:6)

A 60 bp oligonucleotide probe with the following sequence was employed in the screening:

TGACGAAGAGAGTATGAACAGCCCCT-GCTGGCAAGTCAAGTGGCAACTCCGT-CAGCTCGT (SEQ ID NO:7)

Hybridization was conducted overnight at room temperature in buffer containing 20% formamide, 5×SSC, 10% dextran sulfate, 0.1% NaPiPO$_4$, 0.05M NaPO$_4$, 0.05 mg salmon sperm DNA, and 0.1% sodium dodecyl sulfate, followed by several washes at 42° C. in 5×SSC, and then in 2×SSC. Twelve positive clones were identified in the cDNA library, and the positive clones were rescreened by hybridization to a second 60 bp oligonucleotide probe (not overlapping the first probe) having the following sequence:

GGTGAACTGGTCATCCAT-GAAAAGGGTTTTACTACATCTATTC-CCAAACATACTTTCGA (SEQ ID NO:8)

Hybridization was conducted as described above.

Four resulting positive clones were identified and amplified by polymerase chain reaction (PCR) using a primer based on the flanking 5' vector sequence and adding an external ClaI restriction site and a primer based on the 3' flanking vector sequence and. adding an external HindIII restriction site. PCR products were gel purified and subcloned into pGEM-T (commercially available from Promega) by T-A ligation. Three independent clones from different PCRs were then subjected to dideoxy DNA sequencing. DNA sequence analysis of these clones demonstrated that they were essentially identical, with some length variation at their 5' region.

The nucleotide sequence of the coding region of Apo-2 ligand is shown in FIG. 4. Sequencing of the downstream 3' end region of one of the clones revealed a characteristic polyadenylation site (data not shown). The cDNA contained one long open reading frame with an initiation site assigned to the ATG codon at nucleotide positions 91–93. The surrounding sequence at this site is in reasonable agreement with the proposed consensus sequence for initiation sites [Kozak, supra]. The open reading frame ends at the termination codon TAA at nucleotide positions 934–936.

The predicted mature amino acid sequence of human Apo-2 ligand contains 281 amino acids, and has a calculated molecular weight of approximately 32.5 kDa and an isoelectric point of approximately 7.63. There is no apparent signal sequence at the N-terminus, although hydropathy analysis (data not shown) indicated the presence of a hydrophobic region between residues 15 and 40. The absence of a signal sequence and the presence of an internal hydrophobic region suggests that Apo-2 ligand is a type II transmembrane protein. The putative cytoplasmic, transmembrane and extracellular regions are 14, 26 and 241 amino acids long, respectively. The putative transmembrane region is underlined in FIG. 4. A potential N-linked glycosylation site is located at residue 109 in the putative extracellular domain.

An alignment (using the Align computer program) of the amino acid sequence of the C-terminal region of Apo-2 ligand with other known members of the TNF cytokine family showed that, within the C-terminal region, Apo-2 ligand exhibits 23.2% identity to Apo-1 ligand. The alignment analysis showed a lesser degree of identity with other TNF family members: CD40L (20.8), LT-α (20.2%), LT-β (19.6%), TNF-α (19.0%), CD30L and CD27L (15.5%), OX-40L (14.3%), and 4-1BBL (13.7%). In the TNF cytokine family, residues within regions which are predicted to form β strands, based on the crystal structures of TNF-α and LT-α [Eck et al., *J. Bio. Chem.*, 264:17595–17605 (1989); Eck et al., *J. Bio. Chem.*, 267:2119–2122 (1992)], tend to be more highly conserved with other TNF family members than are residues in the predicted connecting loops. It was found that Apo-2 ligand exhibits greater homology to other TNF family members in its putative β strand regions, as compared to homology in the predicted connecting loops. Also, the loop connecting putative β strands, B and B', is markedly longer in Apo-2 ligand.

Example 5

Expression of Human Apo-2 Ligand (ECD)

A soluble Apo-2 ligand extracellular domain ("ECD") fusion construct was prepared, in which another sequence was fused upstream of the C-terminal region of Apo-2 ligand.

A Met Gly His$_{10}$ sequence (derived from the plasmid pET19B, Novagen), followed by a 12 amino acid enterokinase cleavage site Met Gly His His His His His His His His His His Ser Ser Gly His Ile Asp Asp Asp Asp Lys His Met (SEQ ID NO:9) was fused upstream to codons 114–281 of Apo-2 ligand within a baculovirus expression plasmid (pVL1392, Pharmingen). Briefly, the Apo-2 ligand codon 114–281 region was amplified by PCR from the parent pRK5 Apo-2 ligand plasmid with primers complementary to the 5' and 3' regions which incorporate flanking NdeI and BamHI restriction sites respectively. The product was subcloned into pGEM-T (Promega) by T-A ligation, and the DNA sequence was confirmed. The insert was then excised by digestion with NdeI and BamHI and subcloned into a modified baculovirus expression vector pVL1392 (commercially available from Pharmingen) containing an amino terminal Met Gly His$_{10}$ tag and enterokinase cleavage site.

Recombinant baculovirus was generated by co-transfecting the His$_{10}$-Apo-2 ECD plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses were harvested and used for further amplifications. Viral infection and protein expression was performed as described by O'Reilley et al., Baculovirus expression vectors: A laboratory Manual, Oxford:Oxford University Press (1994). The protein was purified by Ni$^{2+}$-chelate affinity chromatography, as described in Example 6 below.

Example 6

Purification of Recombinant Human Apo-2 Ligand (ECD)

Extracts were prepared from recombinant virus-infected and mock-infected Sf9 cells (see Example 5) as described by Rupert et al., *Nature*, 362:175–179 (1993). Briefly, Sf9 cells were washed, resuspended in sonication buffer (25 mL Hepes, pH 7.9; 12.5 mM MgCl$_2$; 0.1 mM EDTA; 10% Glycerol; 0.1% NP-40; .0.4 M KCl), and sonicated twice for 20 seconds on ice. The sonicates were cleared by centrifugation, and the supernatant was diluted 50-fold in loading buffer (50 mM phosphate, 300 mM NaCl, 10% Glycerol, pH 7.8) and filtered through a 0.45 μm filter. A Ni$^{2+}$-NTA agarose column (commercially available from Qiagen) was prepared with a bed volume of 5 mL, washed with 25 mL of water and equilibrated with 25 mL of loading buffer. The filtered cell extract was loaded onto the column at 0.5 mL per minute. The column was washed to baseline A$_{280}$ with loading buffer, at which point fraction collection was started. Next, the column was washed with a secondary wash buffer (50 mM phosphate; 300 mM NaCl, 10% Glycerol, pH 6.0), which eluted nonspecifically bound protein. After reaching A$_{280}$ baseline again, the column was developed with a 0 to 500 mM Imidazole gradient in the secondary wash buffer. One mL fractions were collected and analyzed by SDS-PAGE and silver staining or western blot with Ni$^{2+}$-NTA-conjugated to alkaline phosphatase (Qiagen). Fractions containing the eluted His$_{10}$-Apo-2 ligand protein were pooled and dialyzed against loading buffer.

An identical procedure was repeated with mock-infected Sf9 cells as the starting material, and the same fractions were pooled, dialyzed, and used as control for the purified human Apo-2 ligand.

Figure 5:
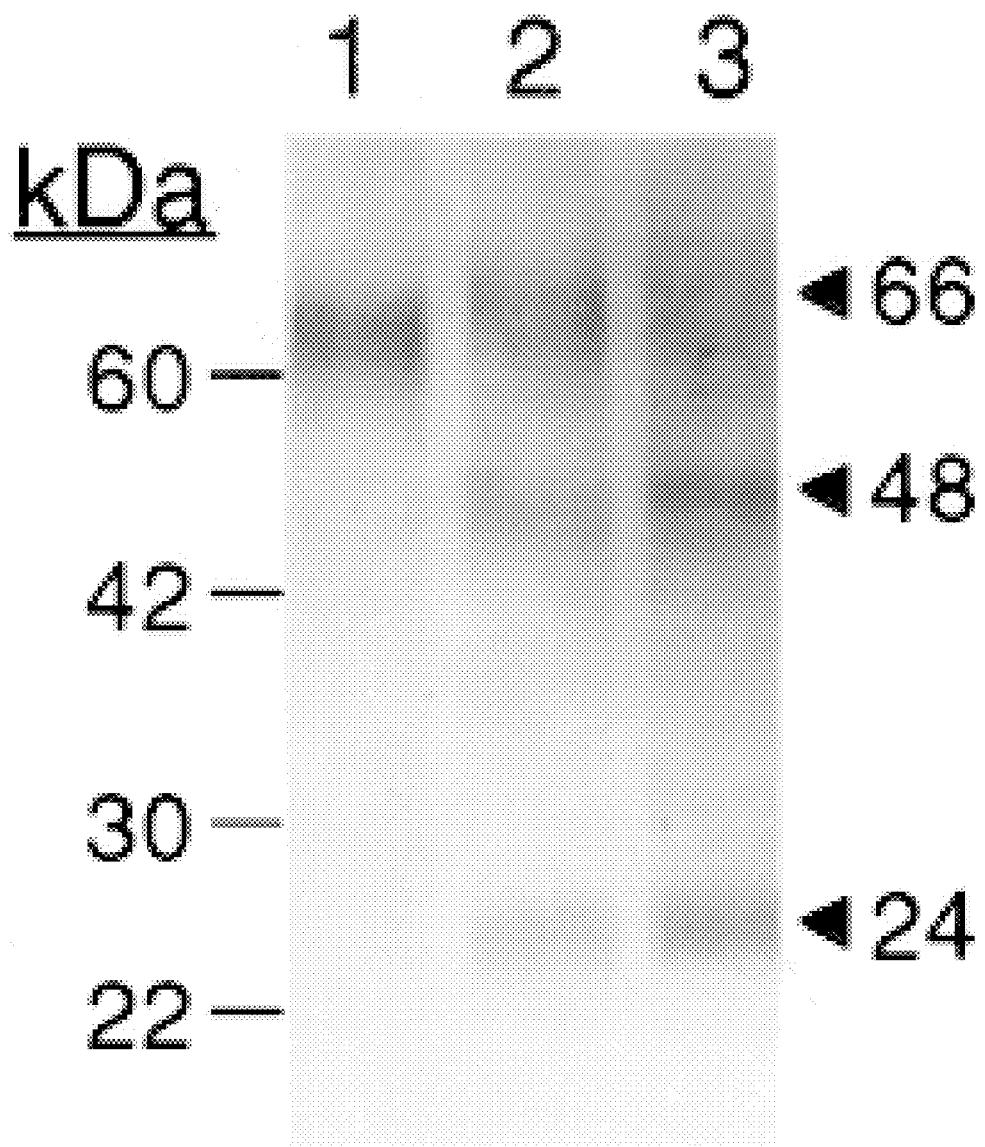
FIG. 5 shows the size and subunit structure of recombinant, $His_{10}$ epitope-tagged soluble Apo-2 ligand expressed in recombinant baculovirus-infected insect cells and purified by $Ni^{2+}$-chelate affinity chromatography, as determined with (lanes 1, 2) or without (lane 3) chemical crosslinking followed by SDS-PAGE and silver staining.

SDS-PAGE analysis of the purified protein revealed a predominant band of Mr 24 kDa, corresponding with the calculated molecular weight of 22.4 kDa for the His$_{10}$-Apo-2 ligand monomer (FIG. 5, lane 3); protein sequence microanalysis (data not shown) confirmed that the 24 kDa band represents the His$_{10}$-Apo-2 ligand polypeptide. Minor 48 kDa and 66 kDa bands were also observed, and probably represent soluble Apo-2 ligand homodimers and homotrimers. Chemical crosslinking of the purified His$_{10}$-Apo-2 ligand by incubation with sulfo-NHS (5 mM) (Pierce Chemical) and EDC (Pierce Chemical) at 25 mM and 50 mM (FIG. 5, lanes 1 and 2, respectively), shifted the protein into the 66 kDa band primarily. These results suggest that the predominant form of Apo-2 ligand in solution is homotrimeric and that these trimers dissociate into dimers and monomers in the presence of SDS.

Example 7

Apoptotic Activity of Apo-2 Ligand on Human Lymphoid Cell Lines

Apoptotic activity of purified, soluble Apo-2 ligand (described in Example 6) was examined using several human lymphoid cell lines. In a first study, the effect of Apo-2 ligand on 9D cells (Genentech, Inc.), derived from Epstein-Barr virus (EBV)-transformed human peripheral blood B cells, was examined. The 9D cells (5×10$^4$ cells/well in RPMI 1640 medium plus 10% fetal calf serum) were incubated for 24 hours with either a media control, Apo-2 ligand (3 μg/ml, prepared as described in Example 6 above), or anti-Apo-1 monoclonal antibody, CH11 (1 μg/ml) [described by Yonehara et al., supra; commercially available from Medical and Biological Laboratories Co.]. The CH11 anti-Apo-1 antibody is an agonistic antibody which mimicks Fas/Apo-1 ligand activity.

After the incubation, the cells were collected onto cytospin glass slides, and photographed under an inverted light microscope. Both Apo-2 ligand and the anti-Apo-1 monoclonal antibody induced a similar apoptotic effect, characterized by cytoplasmic condensation and reduction in cell numbers. (see FIG. 6A).

The effects of the Apo-2 ligand on the 9D cells, as well as on Raji cells (human Burkitt's lymphoma B cell line, ATCC CCL 86) and Jurkat cells (human acute T cell leukemia cell line, ATCC TIB 152) were further analyzed by FACS. The FACS analysis was conducted, using established criteria for apoptotic cell death, namely, the relation of fluorescence staining of the cells with two markers: (a) propidium iodide ("PI") dye, which stains apoptotic but not live cells, and (b) a fluorescent derivative of the protein, annexin V, which binds to the exposed phosphatidylserine found on the surface of apoptotic cells, but not on live cells [Darzynkiewicz et al., *Methods in Cell Biol.*, 41:15–38 (1994); Fadok et al., *J. Immunol.*, 148:2207–2214 (1992); Koopman et al., *Blood*, 84:1415–1420 (1994)].

The 9D cells (FIG. 6B), Raji cells (FIG. 6C), and Jurkat cells (FIG. 6D) were incubated ($1 \times 10^6$ cells/well) for 24 hours with a media control (left panels), Apo-2 ligand (3 µg/ml, prepared as described in Example 6) (center panels), or anti-Apo-1 ligand antibody, CH11 (1 µg/ml) (right panels). The cells were then washed, stained with PI and with fluorescein thiocyanate (FITC)-conjugated annexin V (purchased from Brand Applications) and analyzed by flow cytometry. Cells negative for both PI and annexin V staining (quadrant 3) represent live cells; PI-negative, annexin V-positive staining cells (quadrant 4) represent early apoptotic cells; PI-positive, annexin V-positive staining cells (quadrant 2) represent primarily cells in late stages of apoptosis.

The Apo-2 ligand treated 9D cells exhibited elevated extracellular annexin V binding, as well as a marked increase in uptake of PI (FIG. 6B), indicating that Apo-2 ligand induced apoptosis in the cells. Comparable results were obtained with anti-Apo-1 antibody, CH11 (FIG. 6B). The Apo-2 ligand induced a similar response in the Raji and Jurkat cells, as did the anti-Apo-1 antibody. (see FIGS. 6C and 6D). The induction of apoptosis (measured as the % apoptotic cells) in these cell lines by Apo-2 ligand, as compared to the control and to the anti-Apo-1 antibody, is also shown in Table 1 below.

TABLE 1

| Cell line | Control | % apoptotic cells Apo-2L | Anti-Apo-1 Ab |
|---|---|---|---|
| Lymphoid | | | |
| 9D | 22.5 | 92.4 | 90.8 |
| Raji | 35.9 | 73.4 | 83.7 |
| Jurkat | 5.9 | 77.0 | 18.1 |

The activation of internucleosomal DNA fragmentation by Apo-2 ligand was also analyzed. Jurkat cells (left lanes) and 9D cells (right lanes) were incubated ($2 \times 10^6$ cells/well) for 6 hours with a media control or Apo-2 ligand (3 µg/ml, prepared as described in Example 6), The DNA was then extracted from the cells and labeled with $^{32}$P-ddATP using terminal transferase. The labeled DNA samples were subjected to electrophoresis on 2% agarose gels and later analyzed by autoradiography [Moore et al., *Cytotechnology*, 17:1–11 (1995)]. The Apo-2 ligand induced internucleosomal DNA fragmentation in both the Jurkat cells and 9D cells (FIG. 6E). Such DNA fragmentation is characteristic of apoptosis [Cohen, *Advances in Immunol.*, 50:55–85 (1991)].

To examine the time-course of the Apo-2 ligand apoptotic activity, 9D cells were incubated in microtiter dishes ($5 \times 10^4$ cells/well) with a media control or Apo-2 ligand (3 µg/ml, prepared as described in Example 6) for a period of time ranging from 0 hours to 50 hours. Following the incubation, the numbers of dead and live cells were determined by microscopic examination using a hemocytometer.

Figure 7A:
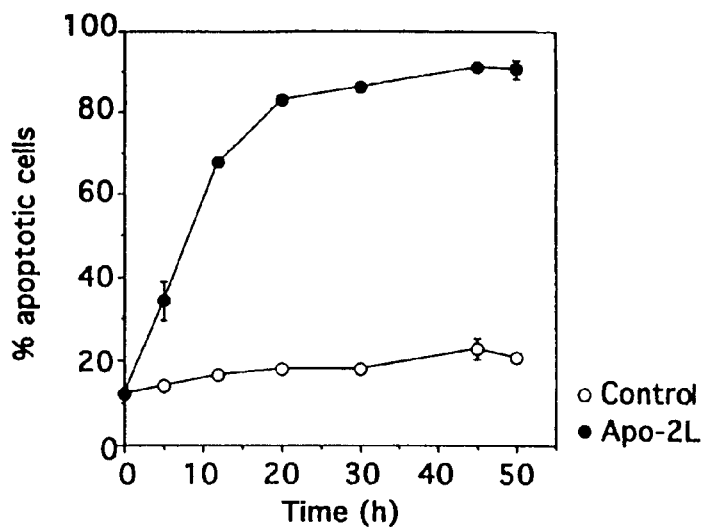
FIGS. 7A–7C show the time course and the dose-dependence of Apo-2 ligand-induced apoptosis and the lack of inhibition of Apo-2 ligand-induced apoptosis by soluble receptor-IgG-fusion proteins based on the Fas/Apo-1 receptor, TNFR1 receptor, or TNFR2 receptor.

As shown in FIG. 7A, maximal levels of cell death were induced in 9D cells within 24 hours.

Figure 7B:
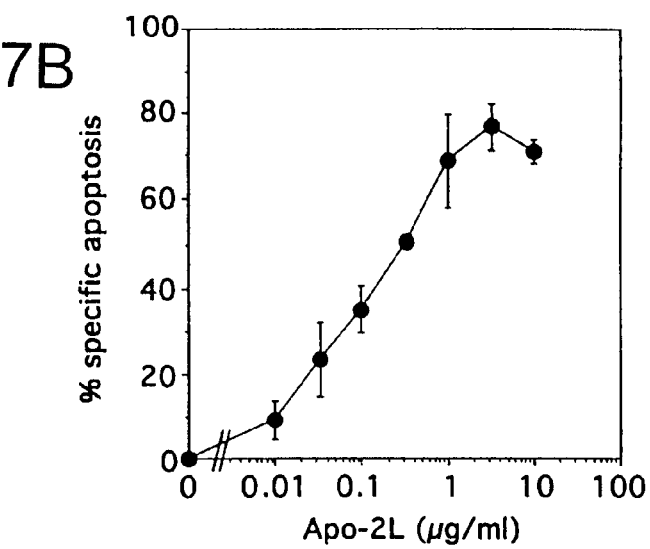

To determine dose-dependency of Apo-2 ligand-induced cell death, 9D cells were incubated ($5 \times 10^4$ cells/well) for 24 hours with serial dilutions of a media control or Apo-2 ligand (prepared as described in Example 6). The numbers of dead and live cells following the incubation were determined as described above. The results are illustrated in FIG. 7B. Specific apoptosis was determined by subtracting the % apoptosis in the control from % apoptosis in Apo-2 ligand treated cells. Half-maximal activation of apoptosis occurred at approximately 0.1 µg/ml (approximately 1 nM), and maximal induction occurred at about 1 to about 3 µg/ml (approximately 10 to 30 nM).

Example 8

Inhibition Assay Using Fas/Apo-1 and TNF Receptors

An assay was conducted to determine if the Fas/Apo-1 receptor, as well as the type 1 and type 2 TNF receptors (TNFR1 and TNFR2), are involved in mediating the apoptotic activity of Apo-2 ligand by testing if soluble forms of these receptors are capable of inhibiting the apoptotic activity of purified, soluble Apo-2 ligand (described in Example 6).

9D cells were incubated ($5 \times 10^4$ cells/well) for 24 hours with a media control or Apo-2 ligand (0.3 µg/ml, prepared as described in Example 6) in the presence of buffer control, CD4-IgG control (25 µg/ml), soluble Apo-1-IgG (25 µg/ml), soluble TNFR1-IgG (25 µg/ml) or soluble TNFR2-IgG fusion protein (25 µg/ml). Soluble derivatives of the Fas/Apo-1, TNFR1 and TNFR2 receptors were produced as IgG fusion proteins as described in Ashkenazi et al., *Methods*, 8:104–115 (1995). CD4-IgG was produced as an IgG fusion protein as described in Byrn et al., *Nature*, 344:667–670 (1990) and used as a control.

Figure 7C:
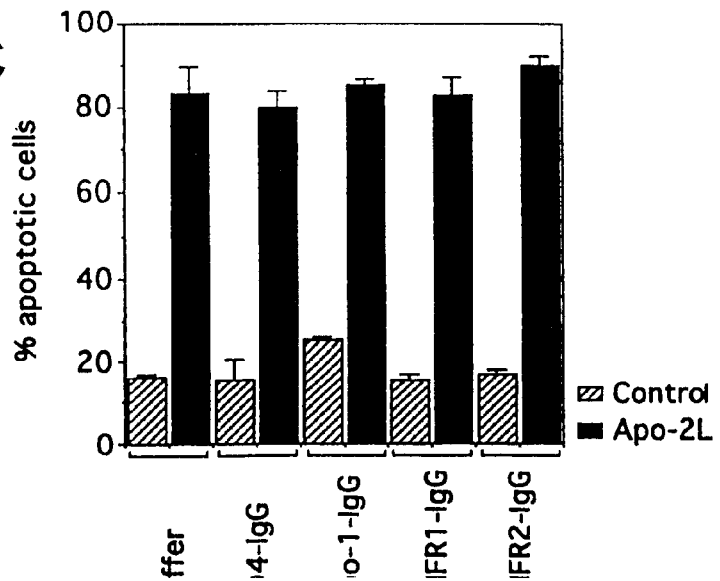

As shown in FIG. 7C, none of the receptor-fusion molecules inhibited Apo-2 ligand apoptotic activity on the 9D cells. These results indicate that Apo-2 ligand apoptotic activity is independent of Fas/Apo-1 and of TNFR1 and TNFR2.

Example 9

Isolation of cDNA Clones Encoding Human Apo-3

Human fetal heart and human fetal lung 1gt10 bacteriophage cDNA libraries (both purchased from Clontech) were screened by hybridization with synthetic oligonucleotide probes based on an EST (Genbank locus W71984), which showed some degree of homology to the intracellular domain (ICD) of human TNFR1 and CD95. W71984 is a 523 bp EST, which in its −1 reading frame has 27 identities to a 43 amino acid long sequence in the ICD of human TNFR1. The oligonucleotide probes used in the screening were 27 and 25 bp long, respectively, with the following sequences: GGCGCTCTGGTGGCCCTTGCAGAAGCC [SEQ ID NO:12] and TTCGGCCGAGAAGTTGAGAAAT-GTC [SEQ ID NO:13].

Hybridization was done with a 1:1 mixture of the two probes overnight at room temperature in buffer containing 20% formamide, 5×SSC, 10% dextran sulfate, 0.1% NaPiPO$_4$. 0.05 M NaPO$_4$, 0.05 mg salmon sperm DNA, and 0.1% sodium dodecyl sulfate (SDS), followed consecutively by one wash at room temperature in 6×SSC, two washes at 37° C. in 1×SSC/0.1% SDS, two washes at 37° C. in 0.5×SSC/0.1% SDS, and two washes at 37° C. in 0.2×SSC/0.1% SDS. One positive clone from each of the fetal heart (FH20A.57) and fetal lung (FL8A.53) libraries were confirmed to be specific by PCR using the respective above hybridization probes as primers. Single phage plaques containing each of the positive clones were isolated by limiting dilution and the DNA was purified using a Wizard lambda prep DNA purification kit (Promega).

The cDNA inserts were excised from the lambda vector arms by digestion with EcoRI, gel-purified, and subcloned into pRK5 that was predigested with EcoRI. The clones were then sequenced in entirety.

Clone FH20A.57 (also referred to as Apo 3 clone FH20.57 deposited as ATCC 55820, as indicated below) contains a single open reading frame with an apparent translational initiation site at nucleotide positions 89–91 and ending at the stop codon found at nucleotide positions 1340–1342 (FIG. 8; SEQ ID NO:11) [Kozak et al., supra]. The cDNA clone also contains a polyadenylation sequence at its 3' end. The predicted polypeptide precursor is 417 amino acids long and has a calculated molecular weight of approximately 45 kDa and a PI of about 6.4. Hydropathy analysis (not shown) suggested the presence of a signal sequence (residues 1–24), followed by an extracellular domain (residues 25–198), a transmembrane domain (residues 199–224), and an intracellular domain (residues 225–417) (FIG. 8; SEQ ID NO:10). There are two potential N-linked glycosylation sites at amino acid positions 67 and 106.

The ECD contains 4 cysteine-rich repeats which resemble the corresponding regions of human TNFR1 (4 repeats), of human CD95 (3 repeats) (FIG. 9) and of the other known TNFR family members (not shown). The ICD contains a death domain sequence that resembles the death domains found in the ICD of TNFR1 and CD95 and in cytoplasmic death signalling proteins such as human FADD/MORT1, TRADD, RIP, and Drosophila Reaper (FIG. 10). Both globally and in individual regions, Apo-3 is related more closely to TNFR1 than to CD95; the respective amino acid identities are 29.3% and 22.8% overall, 28.2% and 24.7% in the ECD, 31.6% and 18.3% in the ICD, and 47.5% and 20% in the death domain.

The fetal lung cDNA clone, clone 5L8A.53, was identical to the fetal heart clone, with the following two exceptions: (1) it is 172 bp shorter at the 5' region; and (2) it lacks the Ala residue at position 236, possibly due to differential mRNA splicing via two consecutive splice acceptor consensus sites (FIG. 10).

As mentioned in Example 1 above, amino acids 1 to 181 of the Apo-2LI clone 18.1 shown in FIG. 1 (SEQ ID NO:1) are identical to the amino acids 1 to 181 of the Apo-3 polypeptide, shown in FIG. 8 (SEQ ID NO:10).

Example 10

Expression of Apo-3

A pRK5 mammalian expression plasmid (described in Example 2) carrying clone FH20A.57 (referred to in Example 9) was transfected transiently into HEK293 cells (referred to in the Examples above) by calcium phosphate precipitation and into HeLa-S3 cells (ATCC No. CCL 2.2) by standard electroporation techniques.

Lysates of metabolically labeled transfected 293 cells were analyzed by immunoprecipitation with a mouse antiserum raised against an Apo-2LI-IgG fusion protein. Transfected cells (5×10$^5$ per lane) were labeled metabolically by addition of 50 µCi $^{35}$S-Met and $^{35}$S-Cys to the growth media 24 hours after transfection. After a 6 hour incubation, the cells were washed several times with PBS, lysed and subjected to immunoprecipitation by anti-Apo-3 antiserum as described in Marsters et al., Proc. Natl. Acad. Sci., 92:5401–5405 (1995). The anti-Apo-3 antiserum was raised in mice against a fusion protein containing the Apo-2LI ECD (as described in Example 3).

Figure 11:
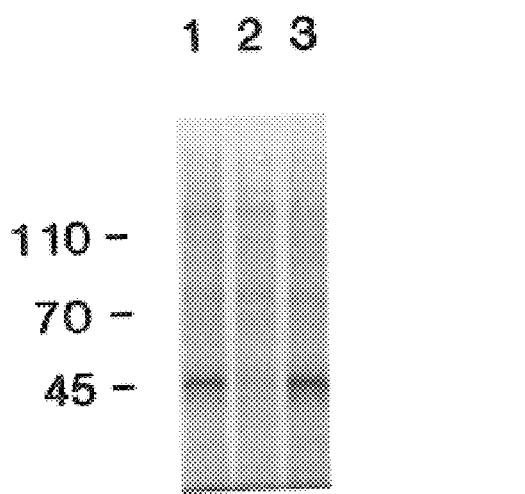
FIG. 11 shows ectopic expression of Apo-3 in HEK 293 cells. Cells were transfected with pRK5-Apo-3 plus pRK5 (5 µg each) (lane 1); pRK5 alone (10 µg) (lane 2); or pRK5-Apo-3 plus pRK5-CrmA (5 µg each) (lane 3). Cells were metabolically labeled with $^{35}$S-Met and $^{35}$S-Cys. Cell lysates were then analyzed by radioimmunoprecipitation using mouse anti-Apo-3 antiserum. The molecular weight standards are shown on the left in kDa.

A predominant radioactive band with a relative molecular weight of about 47 kDa was observed in the pRK5-Apo-3-transfected cells, but not in the cells transfected with pRK5 alone (control) (See FIG. 11, lanes 1, 2). Given the potential glycosylation sites of Apo-3, the observed size is consistent with the size of approximately 45 kDa predicted for the Apo-3 polypeptide precursor.

Example 11

Apoptotic Activity of Apo-3

The transiently transfected HEK293 and HeLa cells described in Example 10 were tested and analyzed for apoptotic activity 36 hours after transfection. Apoptosis was assessed morphologically or quantitated by FACS analysis of cells stained with fluoresceinisothiocyanate (FITC)-conjugated annexin V (Brand Applications) and propidium iodide (PI), as described in Example 7. The annexin V-positive/PI negative cells are in early stages of apoptosis and double-positive cells are in late apoptosis, while annexin V-negative/PI-positive cells are necrotic. Apoptosis was also assessed by DNA fragmentation testing.

Figure 12A:
FIGS. 12a–j illustrate the induction of apoptosis by ectopic expression of Apo-3 in HEK 293 cells. Apoptosis was examined 36 hours after transfection, by morphological analysis (FIGS. 12a–d); by FACS analysis (FIGS. 12e–i); and by DNA laddering (FIG. 12j). Cells were transfected with pRK5 alone (10 µg) (FIGS. 12a; e; j, lane 1); pRK5 plus pRK5-Apo-3 (5 µg each) (FIGS. 12b; f; j, lane 2); pRK5 plus pRK5-CrmA (5 µg each) (FIGS. 12c; g; j, lane 3); or pRK5-Apo-3 plus pRK5-CrmA (5 µg each) (FIGS. 12d; h; j, lane 4). Cells in FIGS. 12a–d were photographed at 400× magnification using Hoffmann optics-based light microscopy. As measured by the total number of annexin V-positive cells, the percent apoptosis in FIGS. 12e–h, respectively, was 37%, 66%, 36% and 26%. Cells in FIG. 12i were transfected with the indicated amount of pRK5-Apo-3 or pRK5-TNFR1 and the appropriate amount of pRK5 plasmid to bring the total amount of DNA to 20 µg.
Figure 12B:
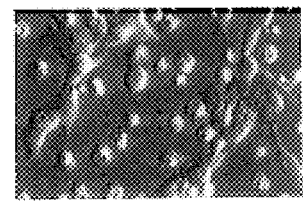

Microscopic examination of the HEK 293 cells transfected with the pRK5-Apo-3 expression plasmid (see Example 10) showed a substantial loss of cell viability as compared to control cells transfected with pRK5 alone; many of the Apo-3 transfected cells exhibited a characteristic apoptotic morphology of membrane blebbing and loss of cell volume (FIGS. 12a and b), suggesting cell death by apoptosis [Cohen, Advances in Immunology, 50:55–85 (1990)].

Figure 12C:
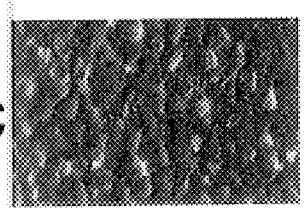
Figure 12D:
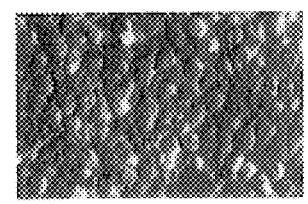
Figure 12E:
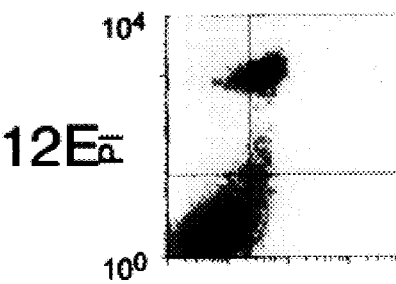
Figure 12F:
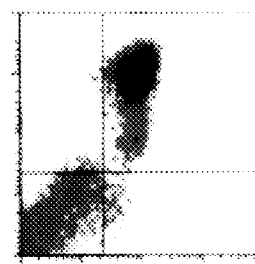
Figure 12G:
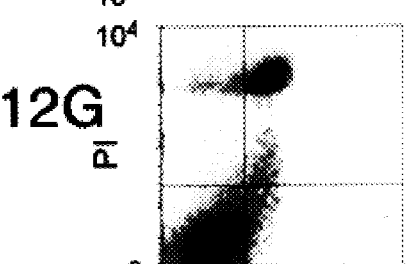
Figure 12H:
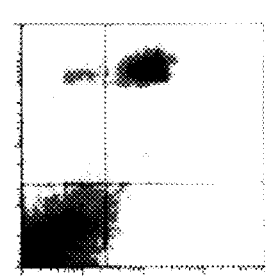

The FACS analysis also revealed that the Apo-3-transfected cells died by apoptosis, by virtue of the presence of exposed phosphatidylserine on their surface (FIGS. 12e–i). It was found that the transient transfection efficiency of the HEK 293 cells was 60–70%; therefore, to target FACS analysis to cells that had taken up the plasmid DNA, the 293 cells were co-transfected with a pRK5-CD4 expression vector (3 µg) as a marker and gated on CD4-positive cells (using phycoerythrin-conjugated anti-CD4 antibody) for analysis. For the co-transfection, the total amount of plasmid DNA was kept constant, but divided between different plasmids. The Apo-3-transfected cells showed a marked increase in PI and annexin V-FITC staining as compared to pRK5-transfected control cells indicating induction of apoptosis by Apo-3. (FIGS. 12e and f).

Figure 12I:
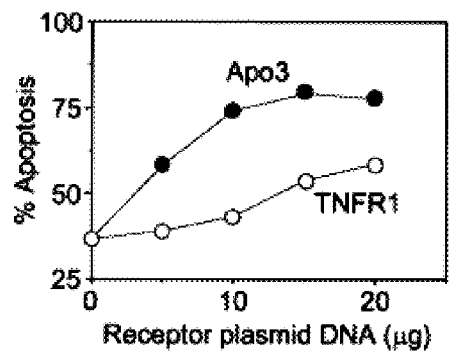

The effect of the dose of plasmid on apoptosis was also tested in the FACS assay. (FIG. 12i). Transfection of 293 cells with either Apo-3 or TNFR1 expression plasmids was associated with a dose-dependent increase in apoptosis; the effect of Apo-3 was more pronounced than that of TNFR1

(FIG. 12i). Similar results were obtained upon Apo-3 transfection of the HeLa cells (data not shown).

Figure 12J:
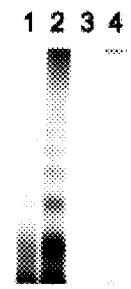

Apoptosis was also assayed by extraction of DNA from the cells, terminal transferase-mediated $^{32}$P-labelling of 3' ends of DNA and 1.5% agarose gel electrophoresis as described by Moore et al., *Cytotechnology*, 17:1–11 (1995). Analysis of the cellular DNA revealed that the Apo-3-transfected cells showed a marked increase in DNA fragmentation as compared to controls (FIG. 12j, lanes 1, 2). The fragmented DNA migrated on agarose gels as a ladder of bands, indicating internucleosomal DNA cleavage, an indication of programmed cell death [Cohen, supra].

Example 12

Inhibition Assay Using CrmA

To investigate whether proteases such as ICE and CPP32/Yama play a role in apoptosis-induction by Apo-3, an assay was conducted to determine if CrmA inhibits Apo-3 function.

Co-transfection of HEK293 cells by a pRK5-CrmA expression plasmid (CrmA sequence reported in Ray et al., supra) and pRK5-Apo-3 did not affect the apparent levels of Apo-3 expressed by the cells (FIG. 11, lane 3). CrmA, however, blocked Apo-3 associated apoptosis as analyzed by morphological examination (FIGS. 12c and d), FACS (FIGS. 12g and h) and DNA fragmentation (FIG. 12j, lanes 3, 4) methods described in Example 11. A similar inhibitory effect of CrmA was observed in Apo-3-transfected HeLa cells (data not shown).

CrmA, a poxvirus-derived inhibitor of the death proteases ICE and CPP32/Yama, blocks death signalling by TNFR1 and CD95. Accordingly, the assay results suggest that Apo-3, TNFR1 and CD95 engage a common signalling pathway to activate apoptotic cell death. In particular, the results suggest that proteases such as ICE and CPP32/Yama may be required for Apo-3 induced apoptosis.

Example 13

Activation of NF-κB by Apo-3

An assay was conducted to determine whether Apo-3 activates NF-κB.

HEK 293 cells were harvested 36 hours after transfection (see Example 10) and nuclear extracts were prepared and 1 μg of nuclear protein was reacted with a $^{32}$P-labelled NF-κB-specific synthetic oligonucleotide probe ATCAGG-GACTTTCCGCTGGGGACTTTCCG (SEQ ID NO:14) [see, also, MacKay et al., *J. Immunol.*, 153:5274–5284 (1994)], alone or together with a 50-fold excess of unlabelled probe, or with an irrelevant $^{32}$P-labelled synthetic oligonucleotide AGGATGGGAAGTGTGTGATATATCCT-TGAT (SEQ ID NO:15). DNA binding was analyzed by an electrophoretic mobility shift assay as described by Hsu et al., supra; Marsters et al., supra, and MacKay et al., supra.

Figure 13:
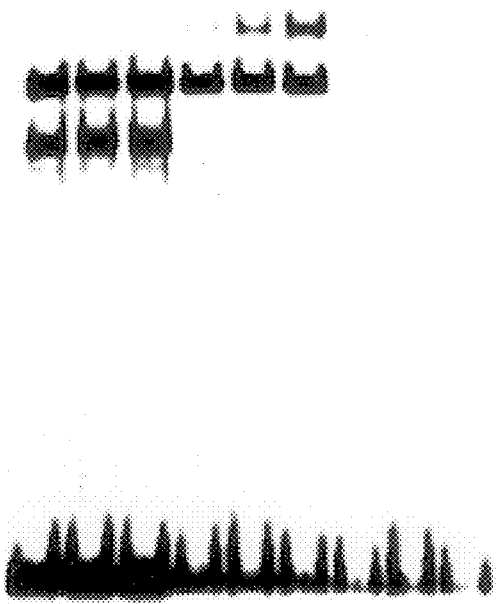
FIG. 13 shows activation of NF-κB by ectopic expression of Apo-3. HEK 293 cells were transfected with 10 μg pRK5 (lanes 1, 4, 7); pRK5-Apo-3 (lanes 2, 5, 7); or pRK5-TNFR1 (lanes 3, 6, 9). Nuclear extracts were prepared 36 hours later and reacted with an irrelevant $^{32}$P-labelled oligonucleotide probe (lanes 1–3); or with a $^{32}$P-labelled NF-κB-specific probe alone (lanes 4–6) or in the presence of 50-fold excess unlabelled oligonucleotide of the same sequence (lanes 7–9).

The results are shown in FIG. 13. The radioactive band at the bottom of the gel in all lanes is the free labelled probe, the two other radioactive bands seen in lanes 1–3 represent non-specific interaction, as does the band common to lanes 1–3 and lanes 4–6. The top radioactive band in lanes 4–6 represents the labelled NF-κB probe, whose migration is delayed by specific interaction with activated NF-κB protein in the nuclear extracts.

Apo-3 transfected cells showed a significant increase in NF-κB-specific DNA binding activity relative to pRK5-transfected controls. TNFR1-transfected cells showed NF-κB activation as well; this activation appeared to be enhanced as compared to the Apo-3-transfected cells. The data thus shows that Apo-3 is capable of regulating transcription of inflammatory response genes and in particular, may be linked to a NF-κB activation pathway.

Example 14

Northern Blot Analysis

Expression of Apo-3 mRNA in human tissues was examined by Northern blot analysis. Human RNA blots were hybridized to a 206 bp $^{32}$P-labelled DNA probe based on the 3' untranslated region of Apo-3; the probe was generated by PCR with the 27 and 25 bp probes (described in Example 9) as PCR primers. Human fetal RNA blot MTN (Clontech) and human adult RNA blot MTN-II (Clontech) were incubated with the DNA probes. Blots were incubated with the probes in hybridization buffer (5×SSPE; 2× Denhardt's solution; 100 mg/mL denatured sheared salmon sperm DNA; 50% formamide; 2% SDS) for 60 hours at 42° C. The blots were washed several times in 2×SSC; 0.05% SDS for 1 hour at room temperature, followed by a 30 minute wash in 0.1×SSC; 0.1% SDS at 50° C. The blots were developed after overnight exposure.

Figure 14:
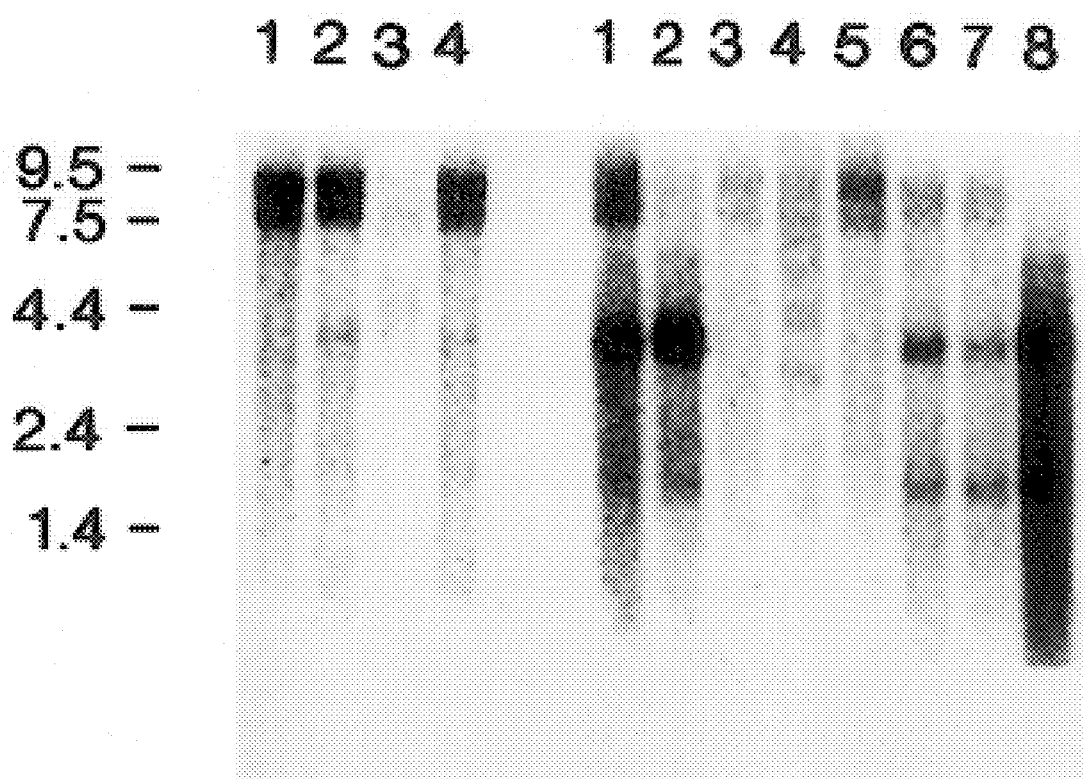
FIG. 14 illustrates expression of Apo-3 mRNA in human tissues as determined by Northern blot hybridization. In the left hand panel are shown fetal brain (1); lung (2); liver (3); kidney (4). In the right hand panel are shown adult spleen (1); thymus (2); prostate (3); testis (4); ovary (5); small intestine (6); colon (7); and peripheral blood lymphocytes (8). The sizes of the molecular weight standards are shown on the left in kb.

As shown in FIG. 14, a predominant mRNA transcript of approximately 4 kb was detected in adult spleen, thymus, and peripheral blood lymphocytes, and less abundantly in small intestine, colon, fetal lung, and fetal kidney. Additional transcripts of approximately 7 and 9 kb were seen mainly in fetal brain, lung and kidney, and in adult spleen and ovary. These results suggest that Apo-3 mRNA is expressed in several types of tissues, including both lymphoid and non-lymphoid tissues.

Example 15

Chromosomal Localization of the Apo-3 Gene

Chromosomal localization of the Apo-3 gene was examined by fluorescence in situ hybridization ("FISH") to normal human lymphocyte chromosomes.

Initial testing by direct hybridization with the Apo-2LI (clone 18.1) cDNA (see Example 1 and FIG. 1) as a probe gave a relatively poor signal to background ratio (data not shown) but suggested that the gene is located on chromosome 1p36. Further testing was conducted using the Apo-3 cDNA probe and FISH mapping [as described by Lichter et al., *Science*, 247:64–69 (1990)] of a human genomic p1-derived artificial chromosome (PAC) library (obtained from Dr. L. C. Tsui, University of Toronto, Toronto, Canada). The Apo-3 probes were biotinylated and detected with avidin-FITC. The normal human lymphocyte chromosomes were counterstained with PI and DAPI [Heng and Tsui, *Chromosome*, 102:325–332 (1993)]. In addition to the "direct" FISH using the Apo-3 cDNA as a probe, the probe was used to identify clones in the genomic PAC library that contain the Apo-3 gene, and the PACs were used as confirmatory probes in FISH. The regional assignment of the genomic probe was determined by the analysis of 20 well-spread metaphases.

A positive PAC clone was mapped by FISH to the short arm of chromosome 1, at position 1p36.3. A second Apo-3-positive genomic PAC was mapped to the same position (data not shown). Positive hybridization signals at 1p36.3 were noted at >95w of the cells. Signals were seen in both chromosome 1 homologues in >90% of the positive spreads.

Recent reports disclose that a genomic region which is deleted in certain human neuroblastomas maps within 1p36.2–1p36.3, indicating that a tumor suppressor gene may be present at this locus. Four additional TNFR gene family members, TNFR2, CD30, 4.1BB and OX40, reside in 1p36 [see Gruss and Dower, supra] but are outside the deleted region [White et al., *Proc. Natl. Acad. Sci.*, 92:5520–5524 (1995)].

Deposit of Material

The following materials have been deposited with the American Type Culture Collection, 10801 University Blvd., Manassass Va., USA (ATCC):

| Material | ATCC Dep. No. | Deposit Date |
|---|---|---|
| 2935-pRK5-hApo-2L-myc clone 2.1 | CRL-12014 | Jan. 3, 1996 |
| Apo-2LI clone 18.1 | 97493 | Mar. 27, 1996 |
| Apo-3 clone FH20.57 | 55820 | Sept. 5, 1996 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the. pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated Apo-3 polypeptide comprising the amino acid sequence of SEQ ID NO:10.

2. An isolated Apo-3 polypeptide having an extracellular domain sequence comprising amino acid residues 1 to 198 of SEQ ID NO:10.

3. An isolated Apo-3 polypeptide having a death domain sequence comprising amino acid residues 338 to 417 of SEQ ID NO:10.

4. A chimeric molecule comprising the extracellular domain sequence of claim 2 fused to a heterologous amino acid sequence.

5. The chimeric molecule of claim 4 wherein said heterologous amino acid sequence is an epitope tag sequence.

6. The chimeric molecule of claim 4 wherein said heterologous amino acid sequence is an immunoglobulin sequence.

7. The chimeric molecule of claim 6 wherein said immunoglobulin sequence is an IgG.

8. An isolated Apo-3 polypeptide selected from the group consisting of:
   a) a soluble, extracellular Apo-3 polypeptide comprising an extracellular domain sequence of a native sequence Apo-3 Polypeptide shown in SEO ID NO:10, and
   b) a fragment of the extracellular polypeptide of a), wherein said fragment is capable of inducing or stimulating apoptosis in at least one type of mammalian cell or is an immunizing agent capable of raising antibodies to said fragment.

9. The Apo-3 polypeptide of claims 1 or 7 wherein said Apo-3 polypeptide has an amino acid deletion at residue 236 in the amino acid sequence shown in SEQ ID NO:10.

* * * * *

UNITED STATES PATENT AND TRADEMARK OFFICE
CERTIFICATE OF CORRECTION

PATENT NO.     : 6,462,176 B1                                         Page 1 of 1
DATED          : October 8, 2002
INVENTOR(S)    : Ashkenazi et al.

It is certified that error appears in the above-identified patent and that said Letters Patent is hereby corrected as shown below:

<u>Column 60,</u>
Line 52, delete "claim 7" and insert therefor -- claim 3 --.

Signed and Sealed this

Fifteenth Day of April, 2003

JAMES E. ROGAN
*Director of the United States Patent and Trademark Office*